United States Patent [19]

Lee et al.

[11] Patent Number: 4,970,198

[45] Date of Patent: Nov. 13, 1990

[54] ANTITUMOR ANTIBIOTICS (LL-E33288 COMPLEX)

[75] Inventors: May D. Lee, Monsey; Michael Greenstein, Suffern, both of N.Y.; David P. Labeda, Peoria, Ill.; Amedeo A. Fantini, New City, N.Y.

[73] Assignee: American Cyanamid Company, Stamford, Conn.

[21] Appl. No.: 9,321

[22] Filed: Jan. 30, 1987

Related U.S. Application Data

[63] Continuation-in-part of Ser. No. 787,066, Oct. 17, 1985, abandoned, which is a continuation-in-part of Ser. No. 672,031, Nov. 16, 1984, abandoned.

[51] Int. Cl.$^5$ .................... A61K 31/71; C07H 15/00
[52] U.S. Cl. ........................................ 514/25; 514/53; 536/16.8; 536/17.5; 536/17.6; 536/18.1; 435/74; 435/867

[58] Field of Search .................... 536/17.5, 17.6, 18.1, 536/16.8; 514/25, 53; 435/867, 74

[56] References Cited

U.S. PATENT DOCUMENTS 4,552,867 11/1985 Martin et al. .................. 536/16.8

OTHER PUBLICATIONS

Johnson et al., Cancer Treatment Reviews, (1975), vol. 2, pp. 1–5.

*Primary Examiner*—Johnnie R. Brown
*Assistant Examiner*—Elli Peselev
*Attorney, Agent, or Firm*—H. G. Jackson

[57] ABSTRACT

Antibacterial and antitumor agents designated LL-E33288 complex and their production by new strains of *Micromonospora echinospora* ssp. *calichensis* NNRL-15839, NNRL-15975 and NNRL-18149, are disclosed.

16 Claims, 28 Drawing Sheets

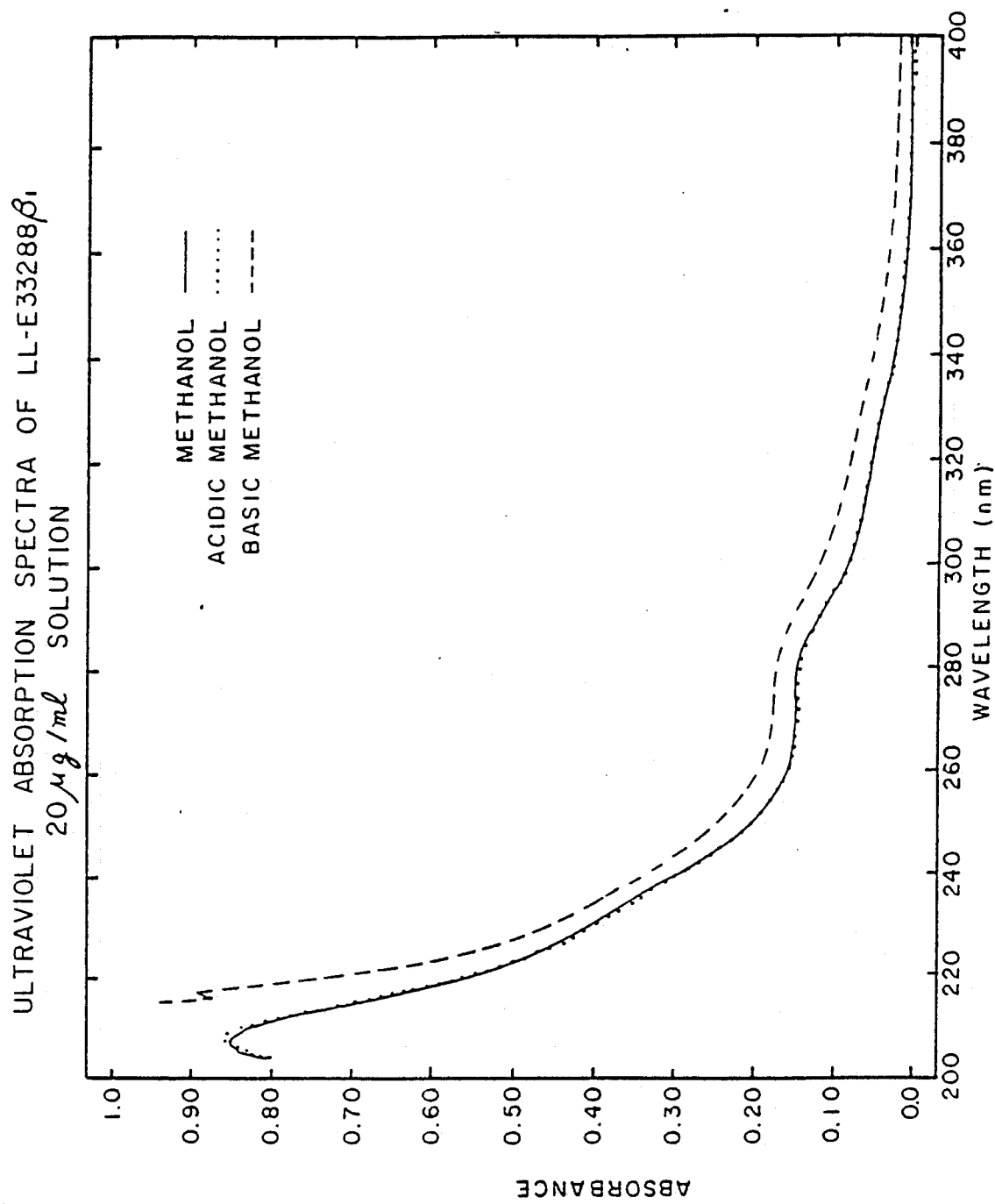

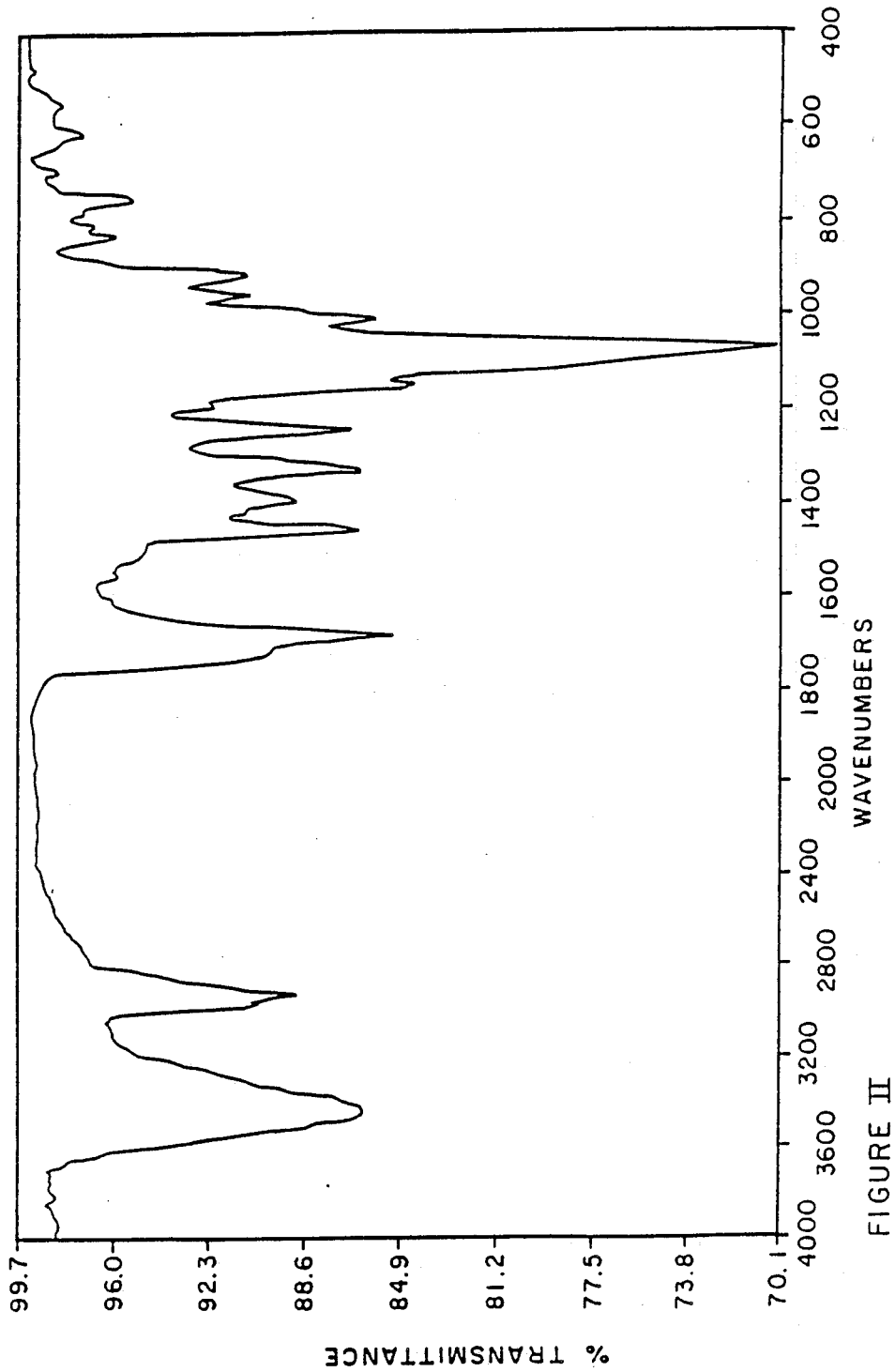
FIGURE II

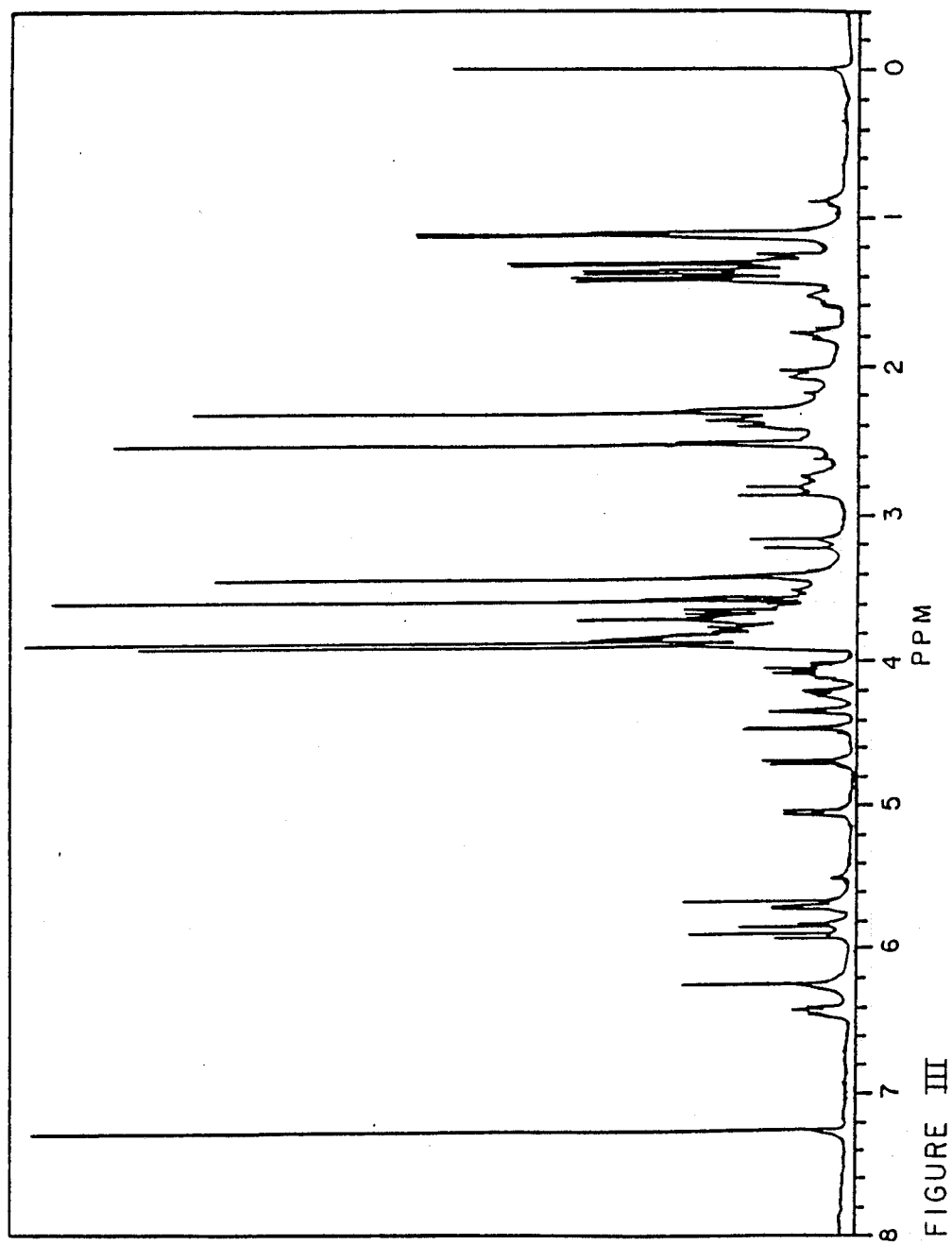

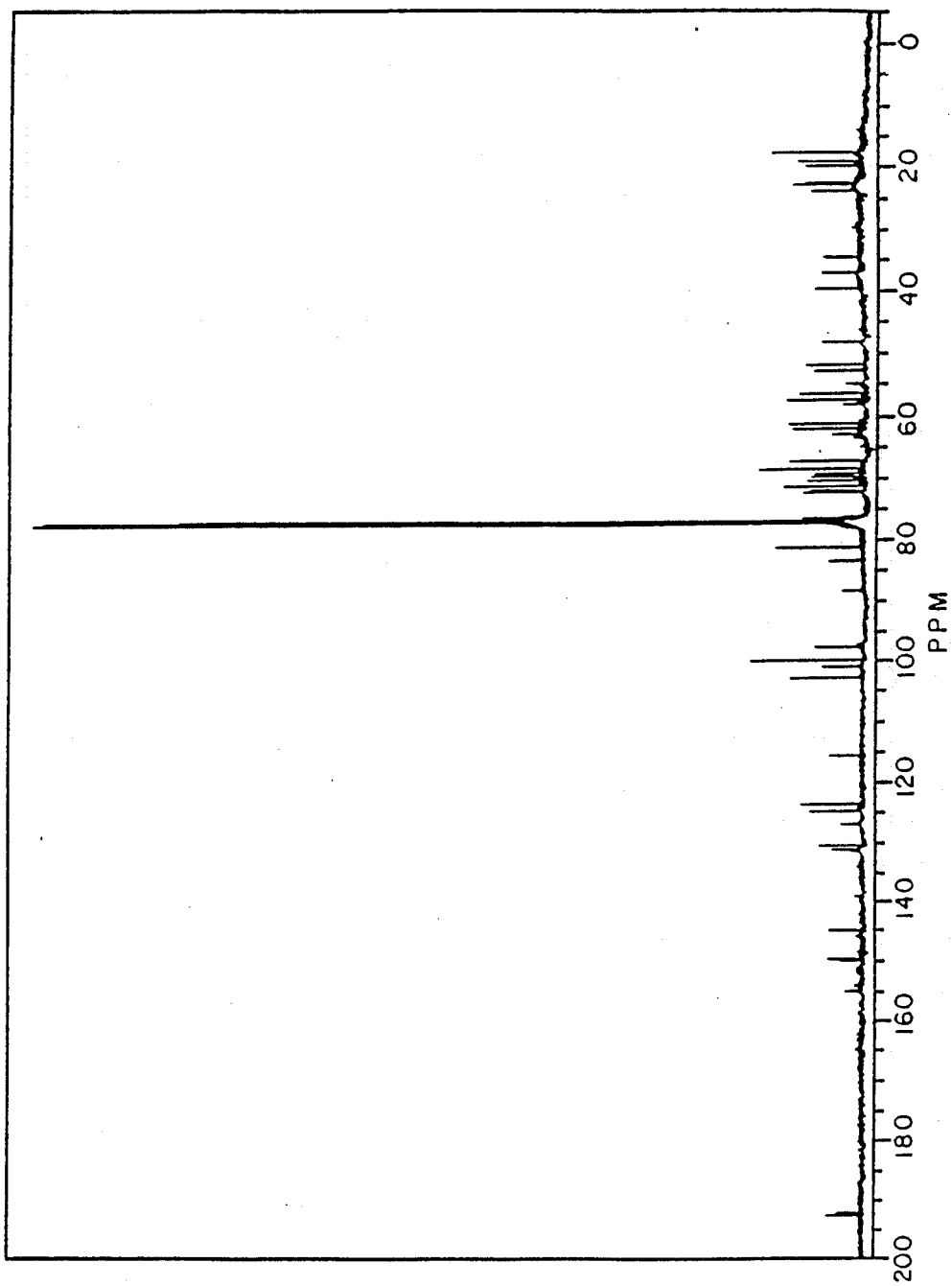
FIGURE IV

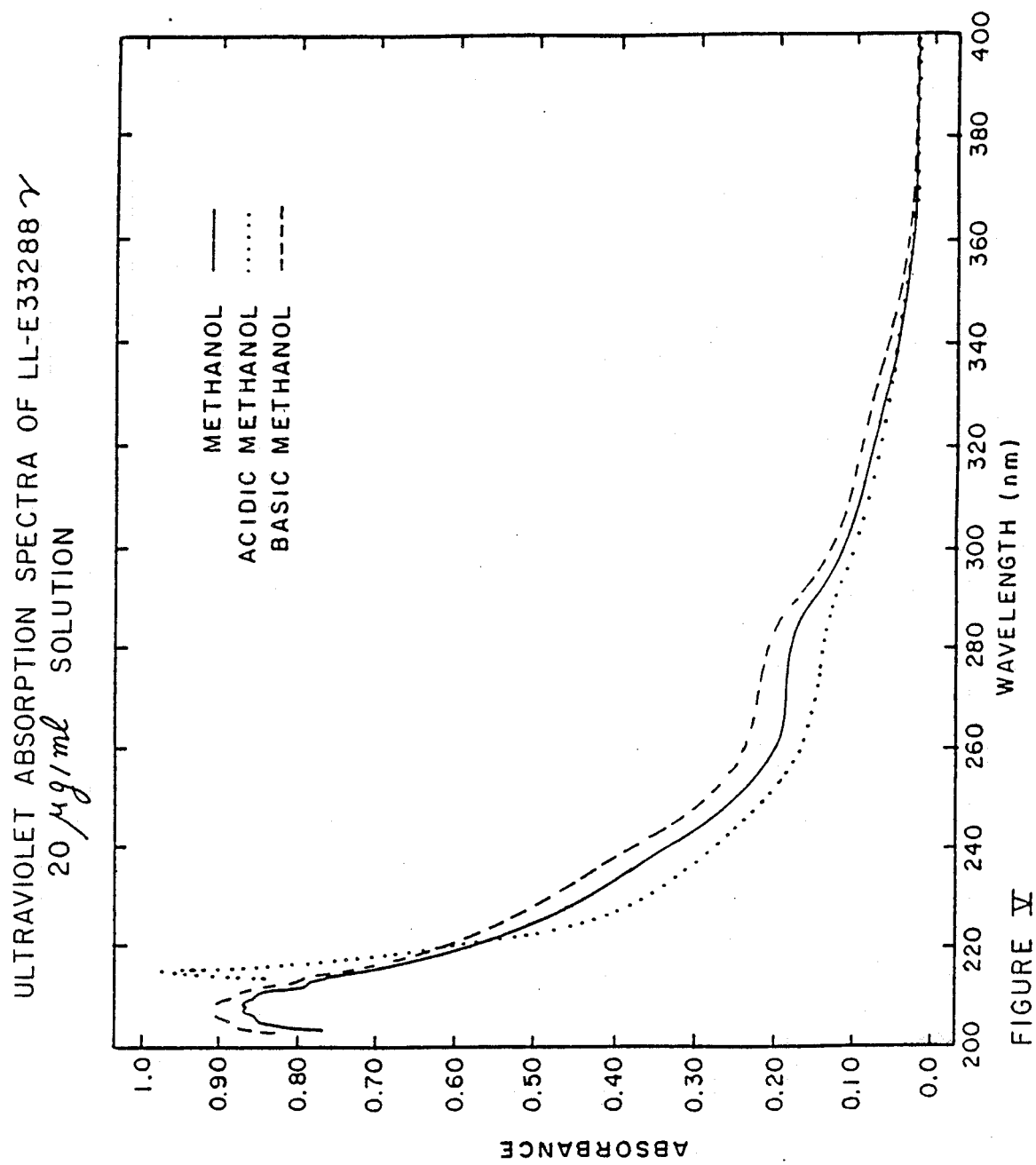
FIGURE V

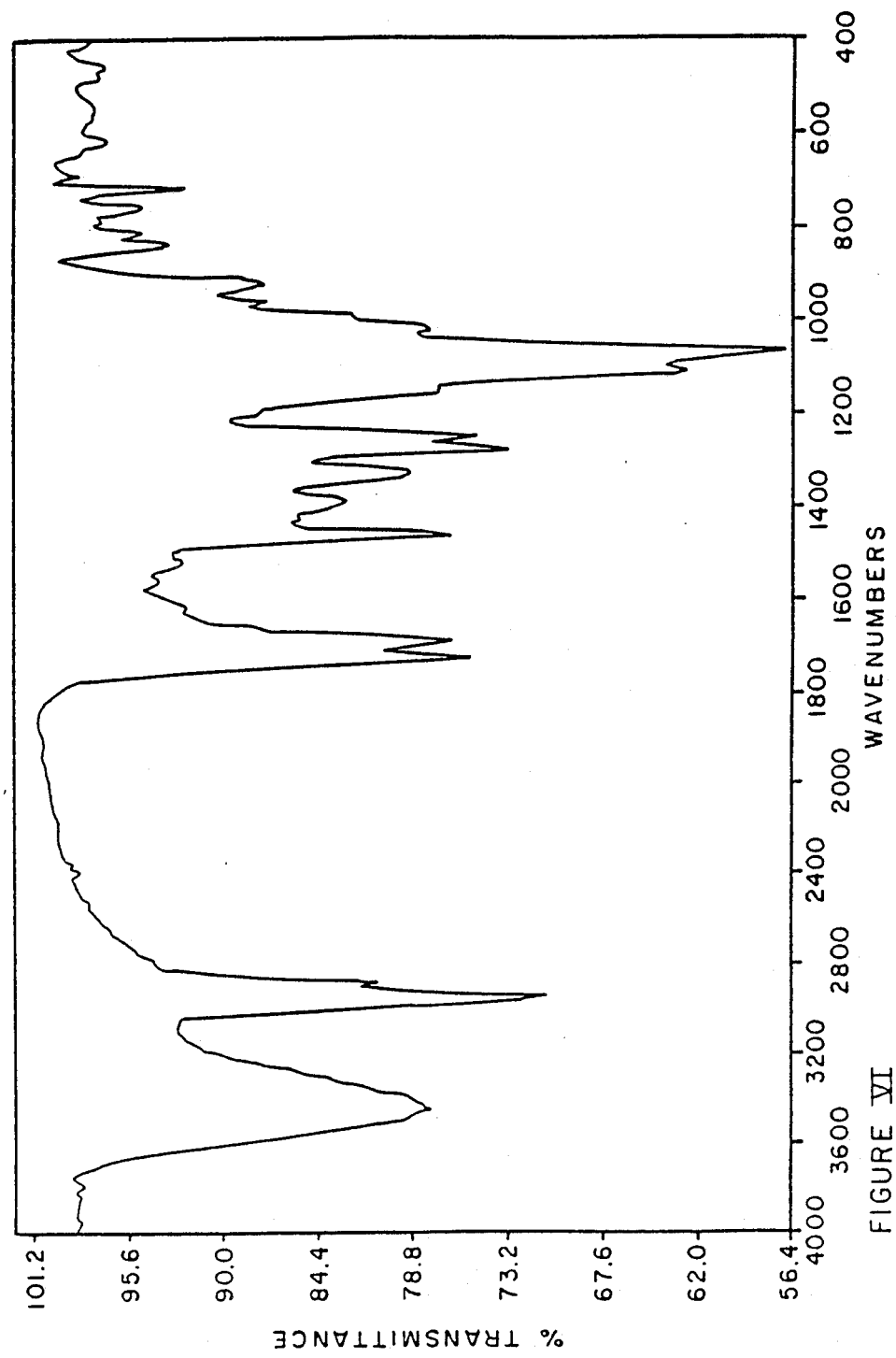
FIGURE VI

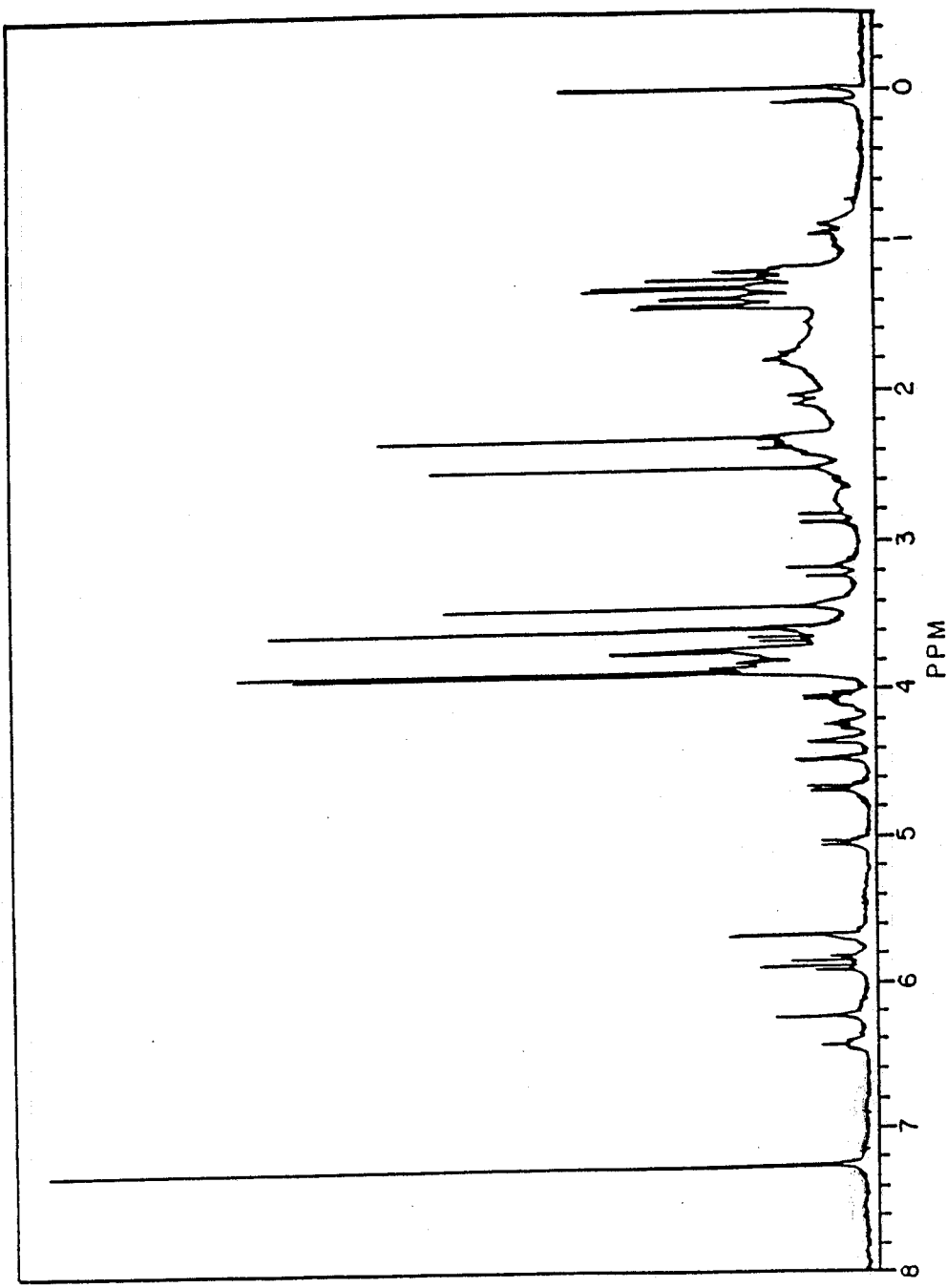
FIGURE VII

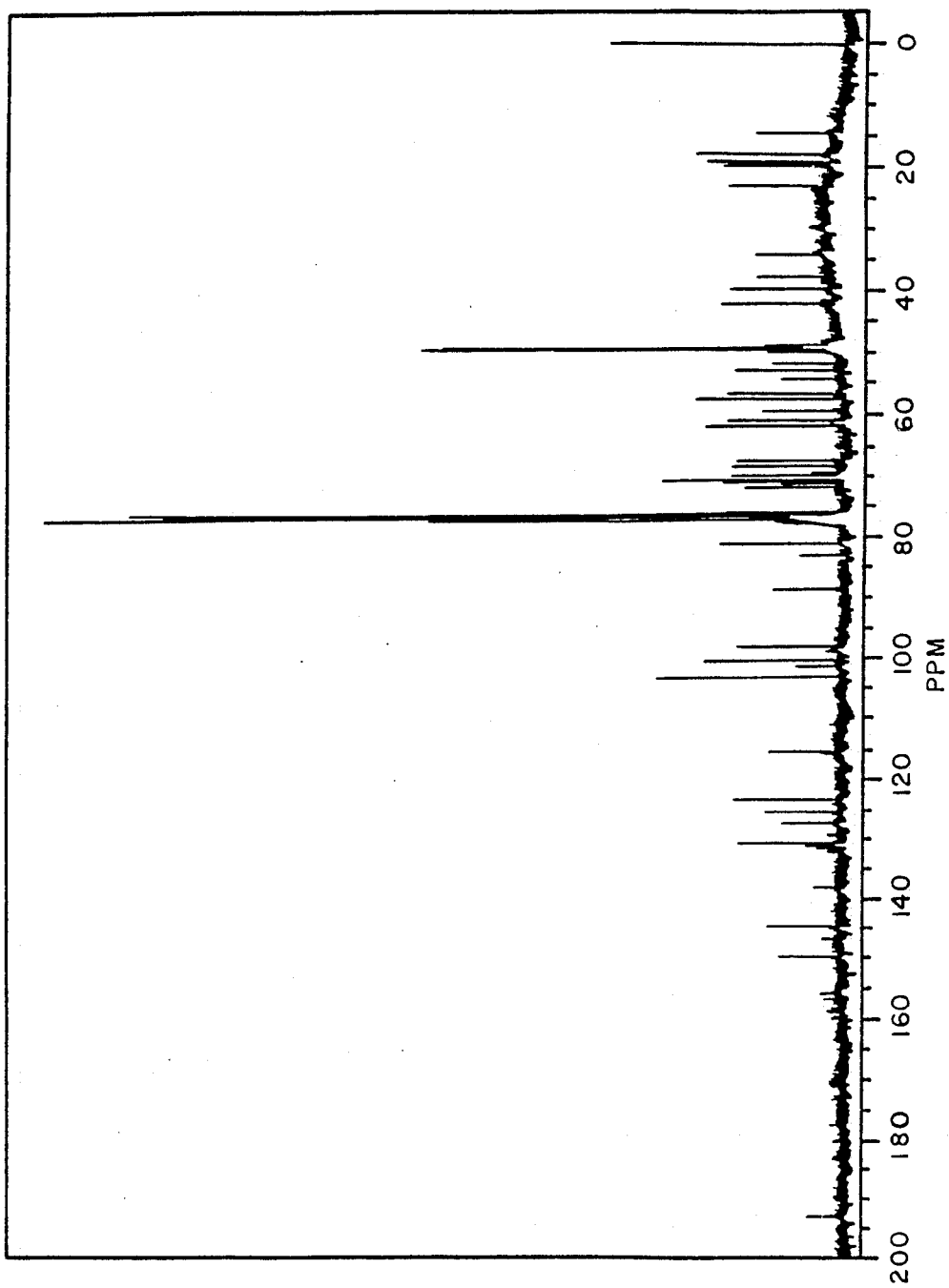
FIGURE VIII

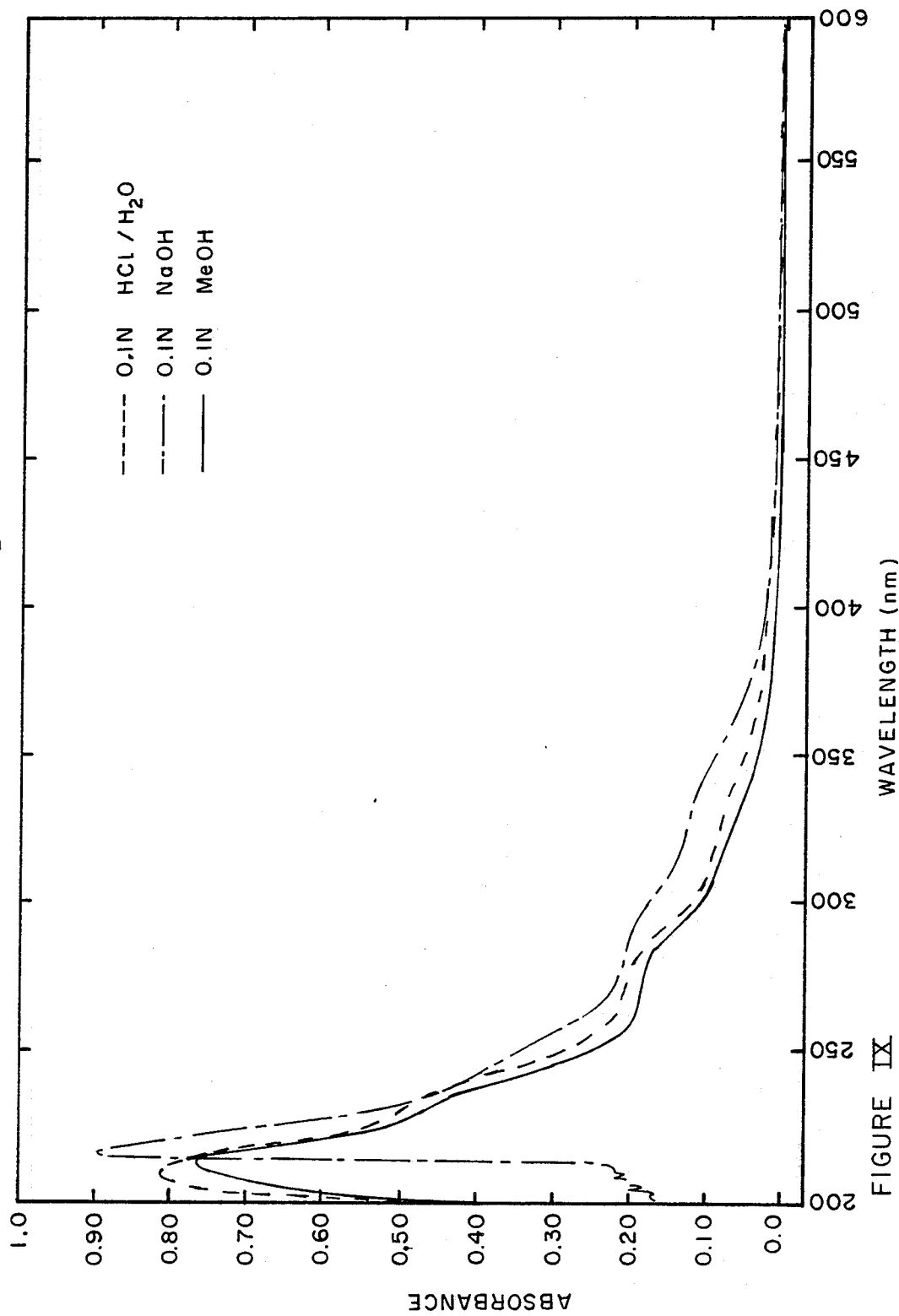

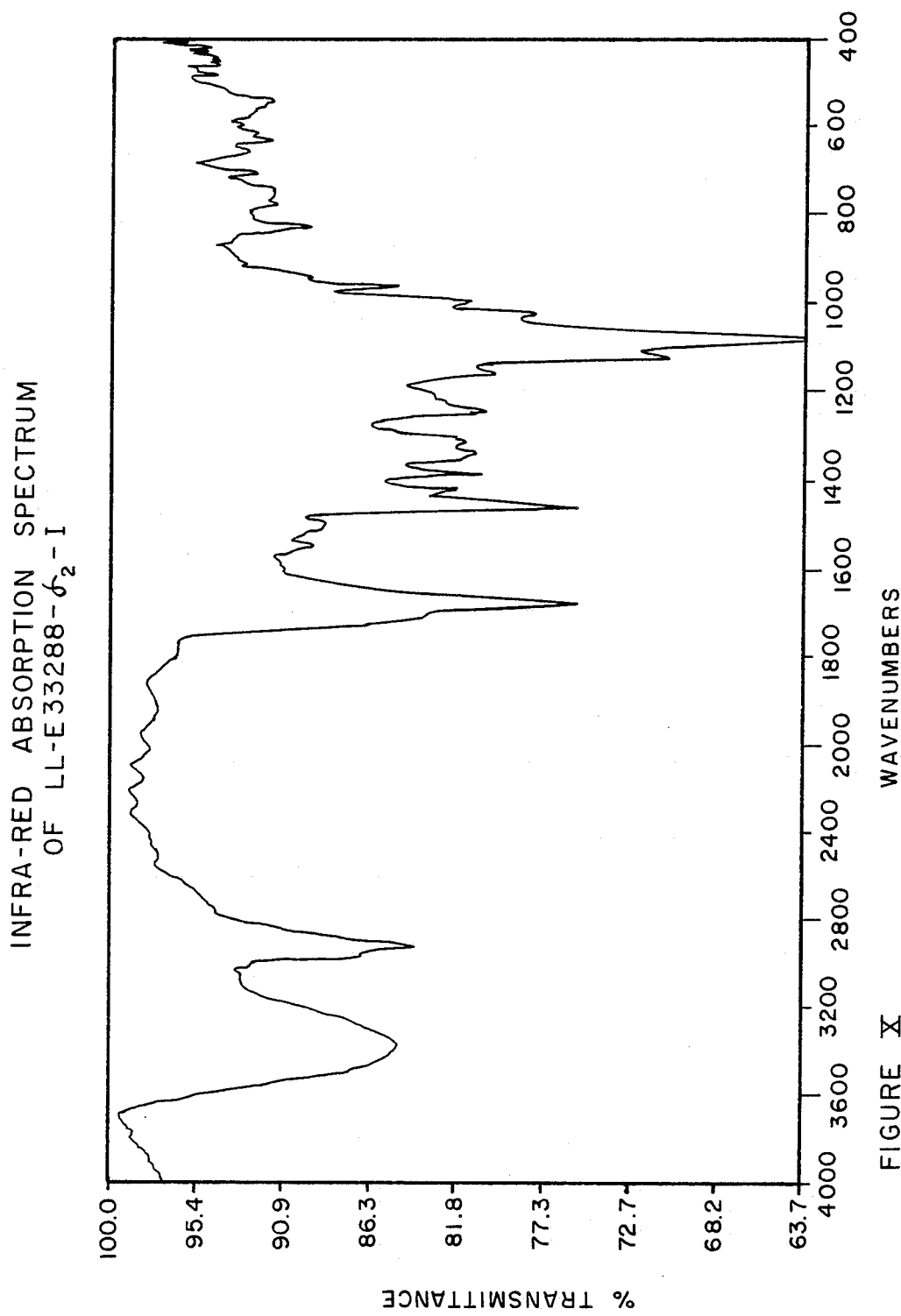

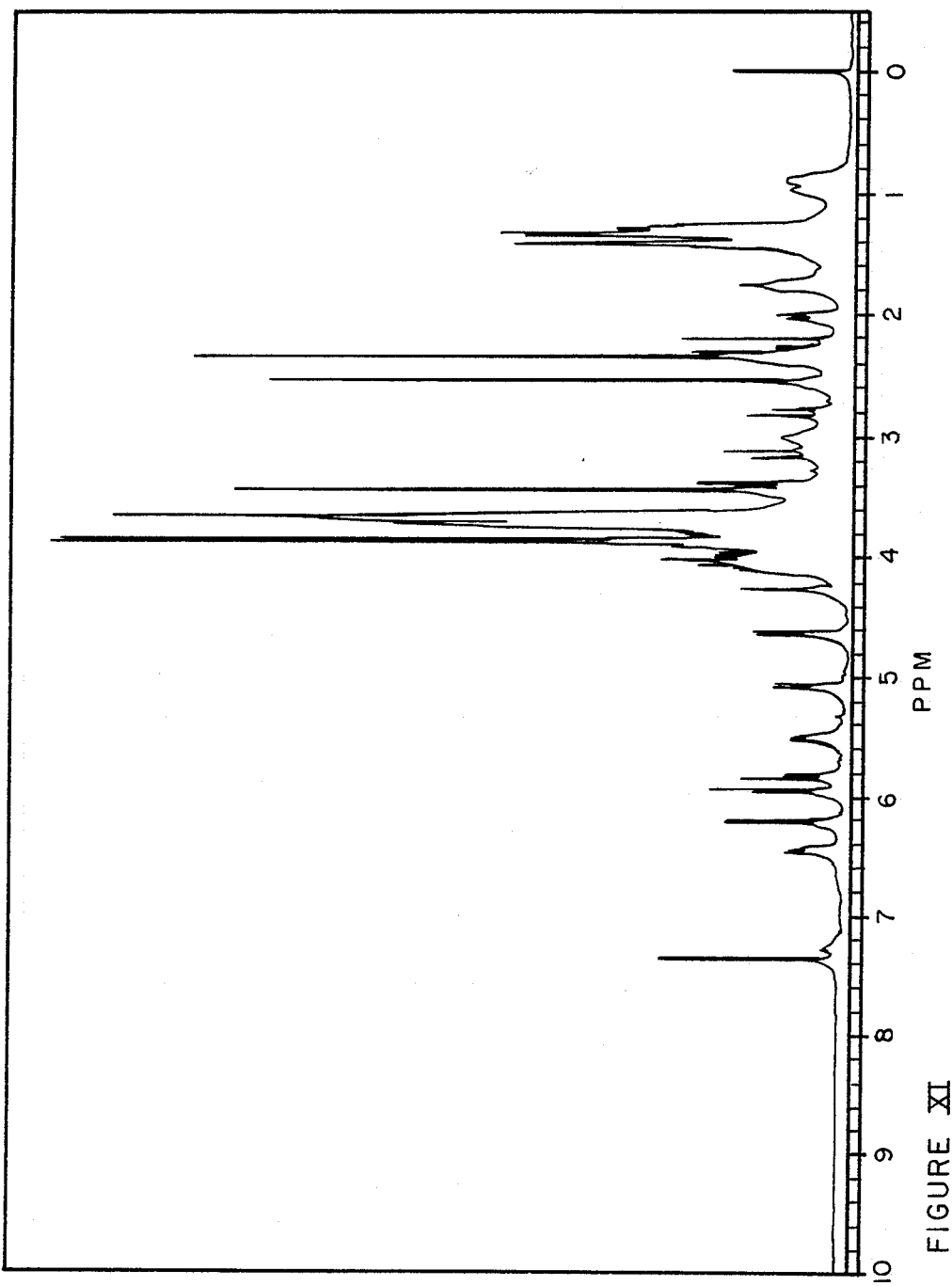
FIGURE XI

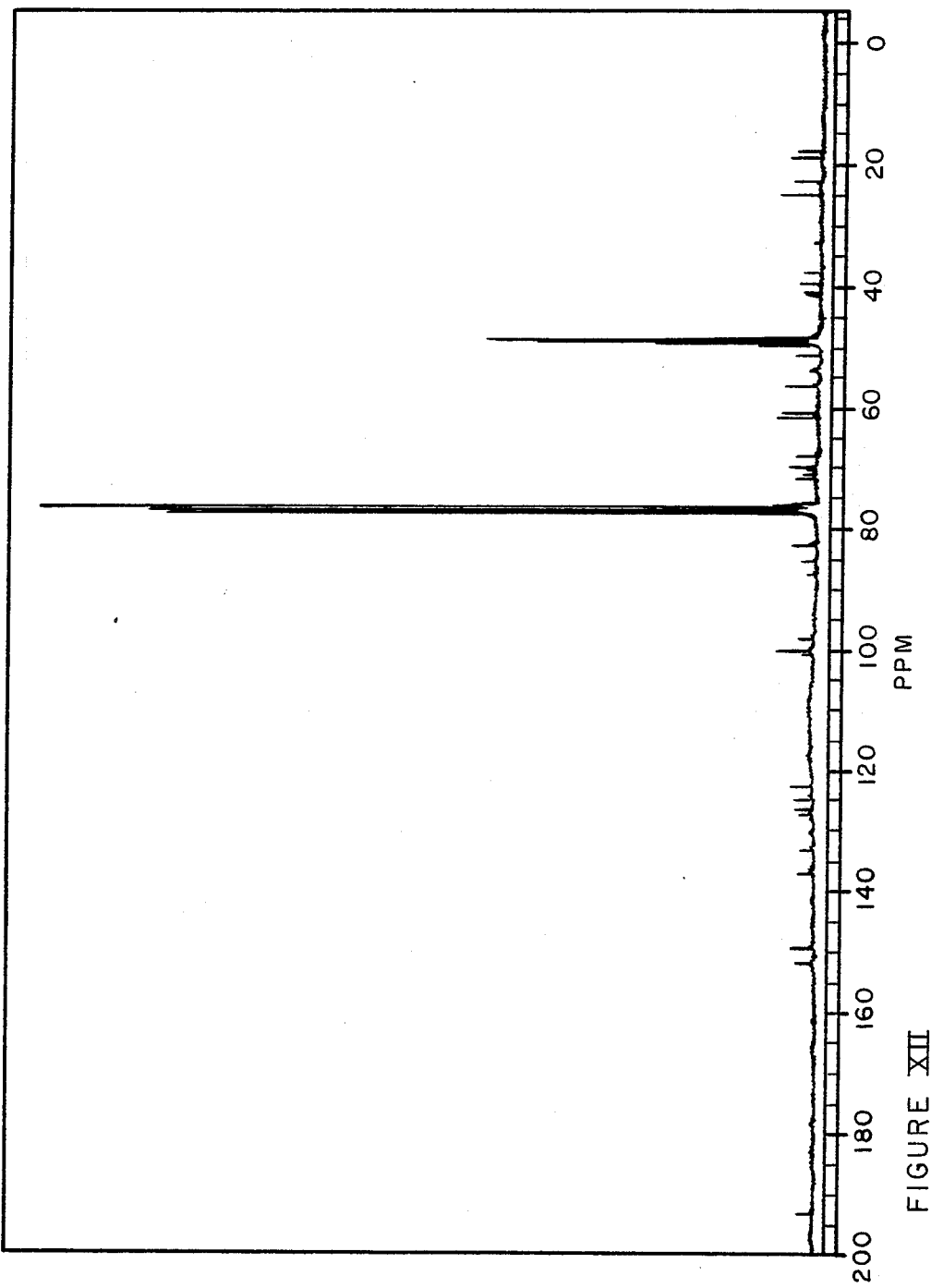
FIGURE XII

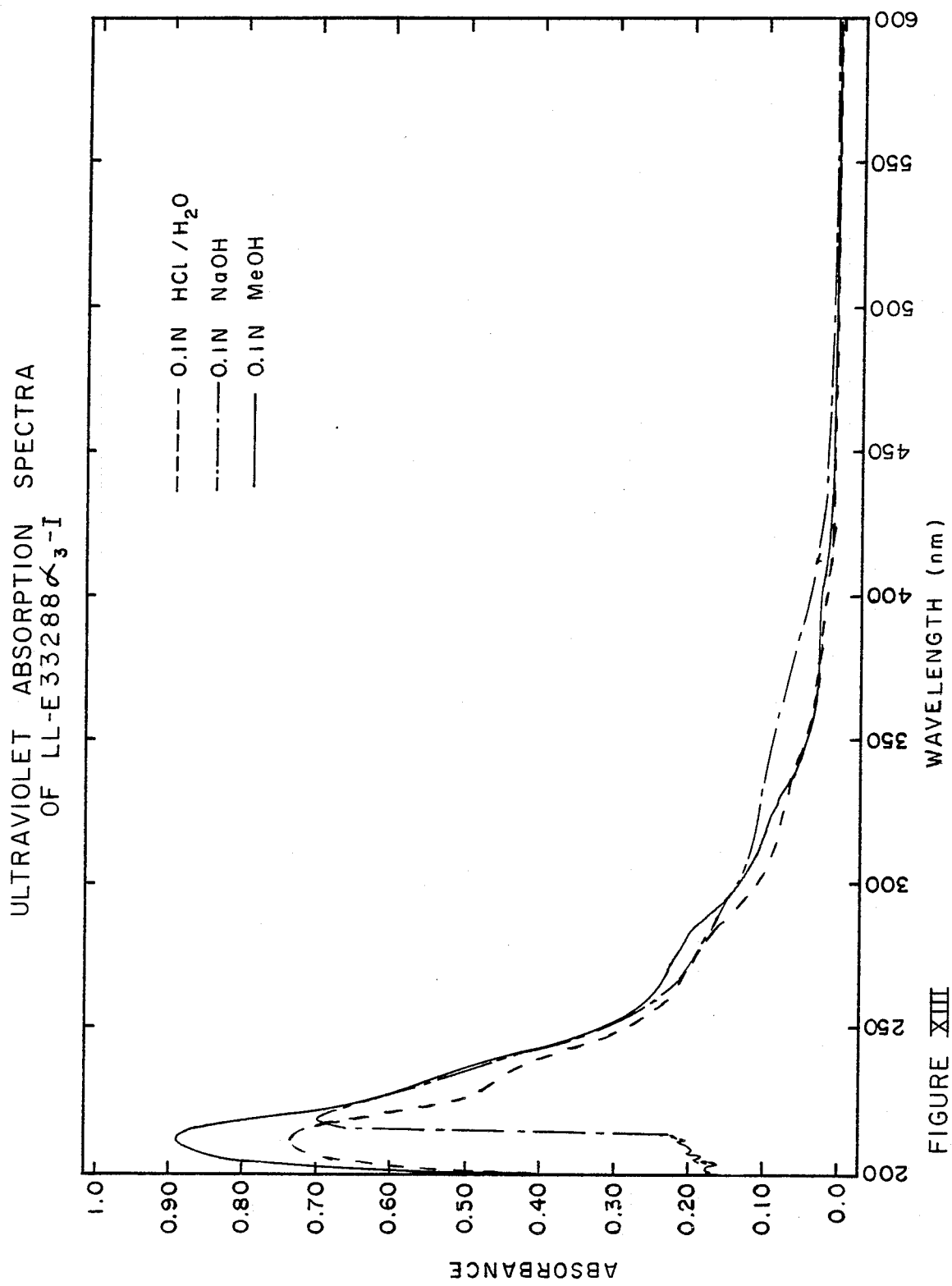

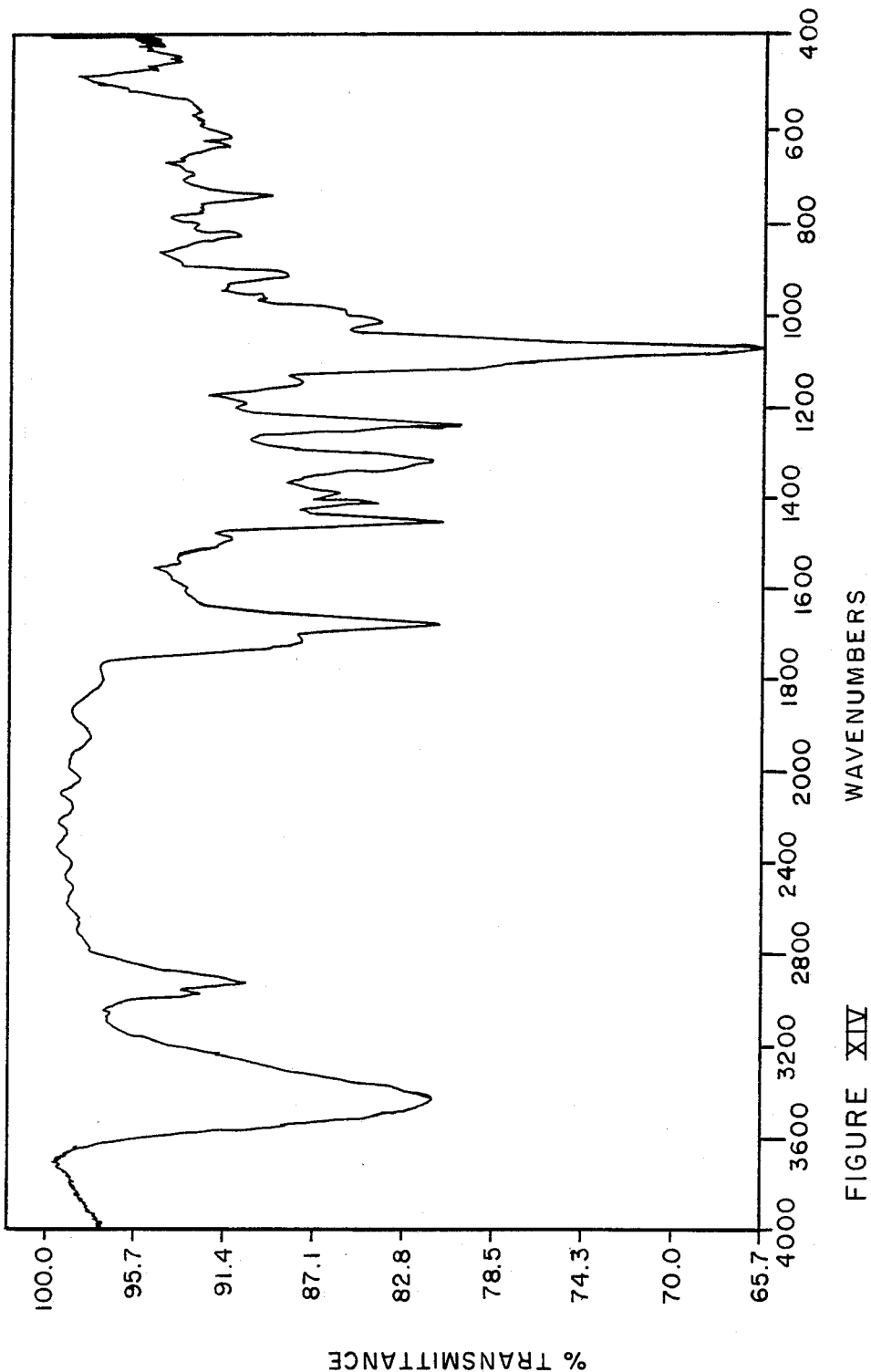
FIGURE XIV

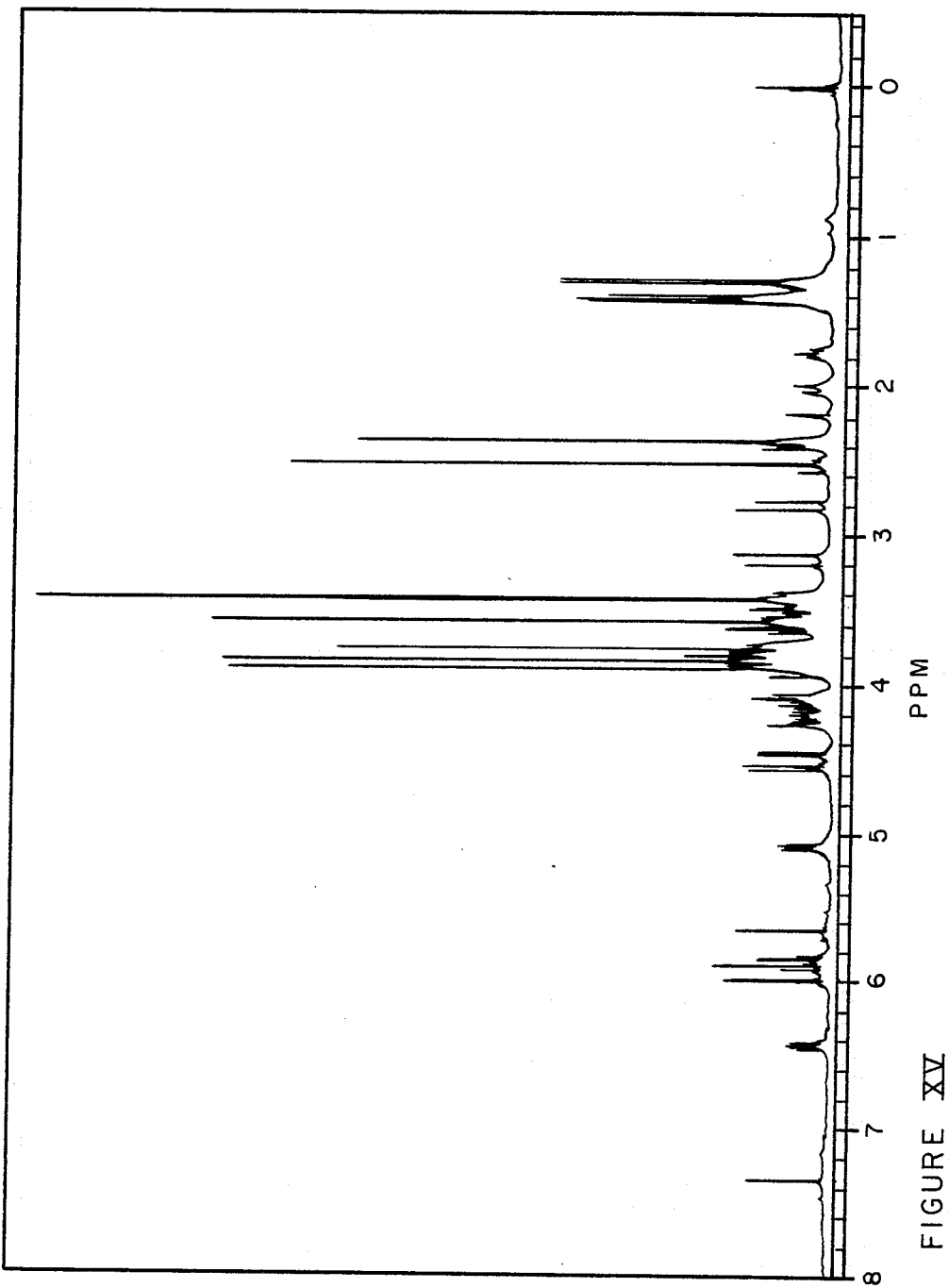
FIGURE XV

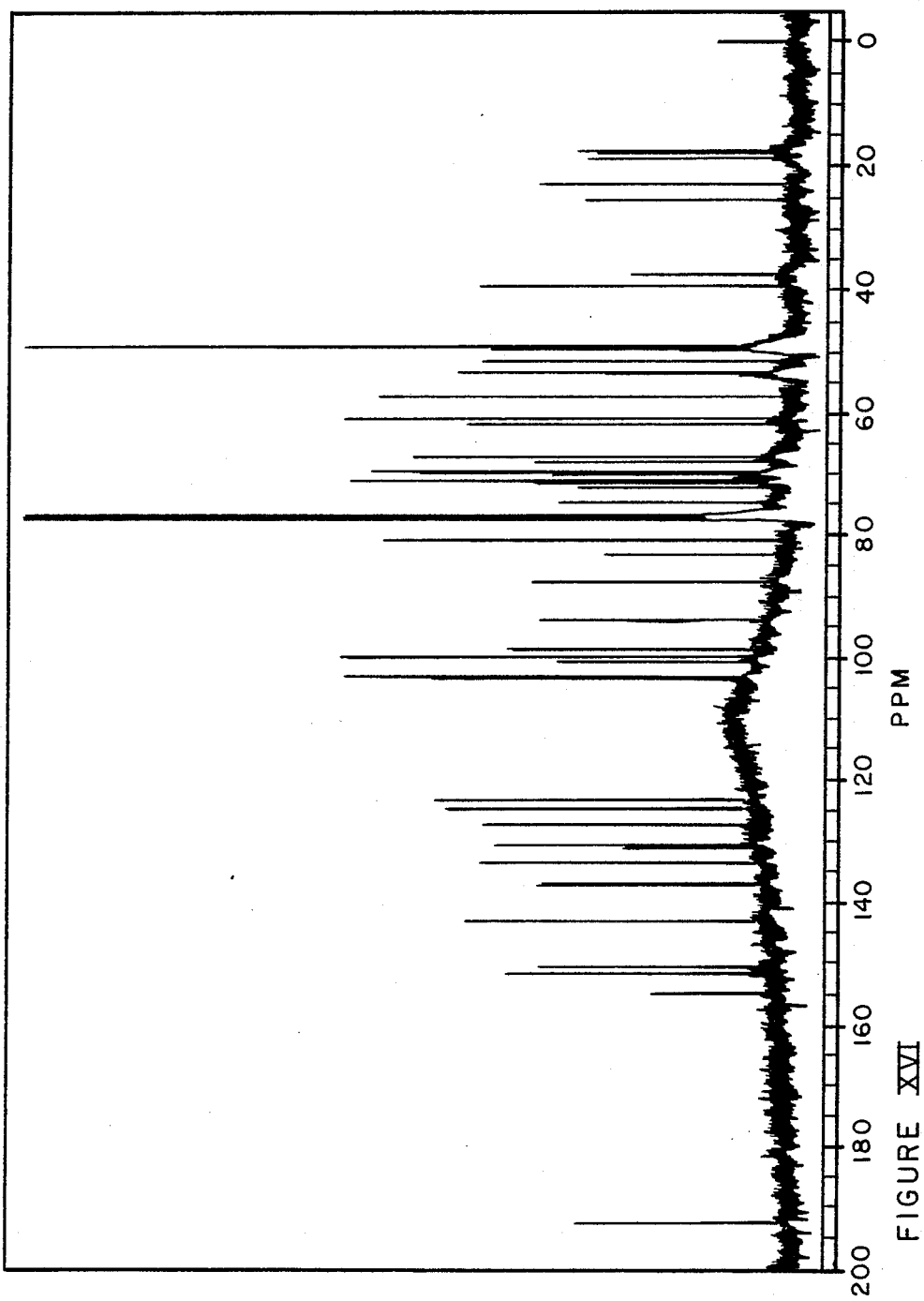

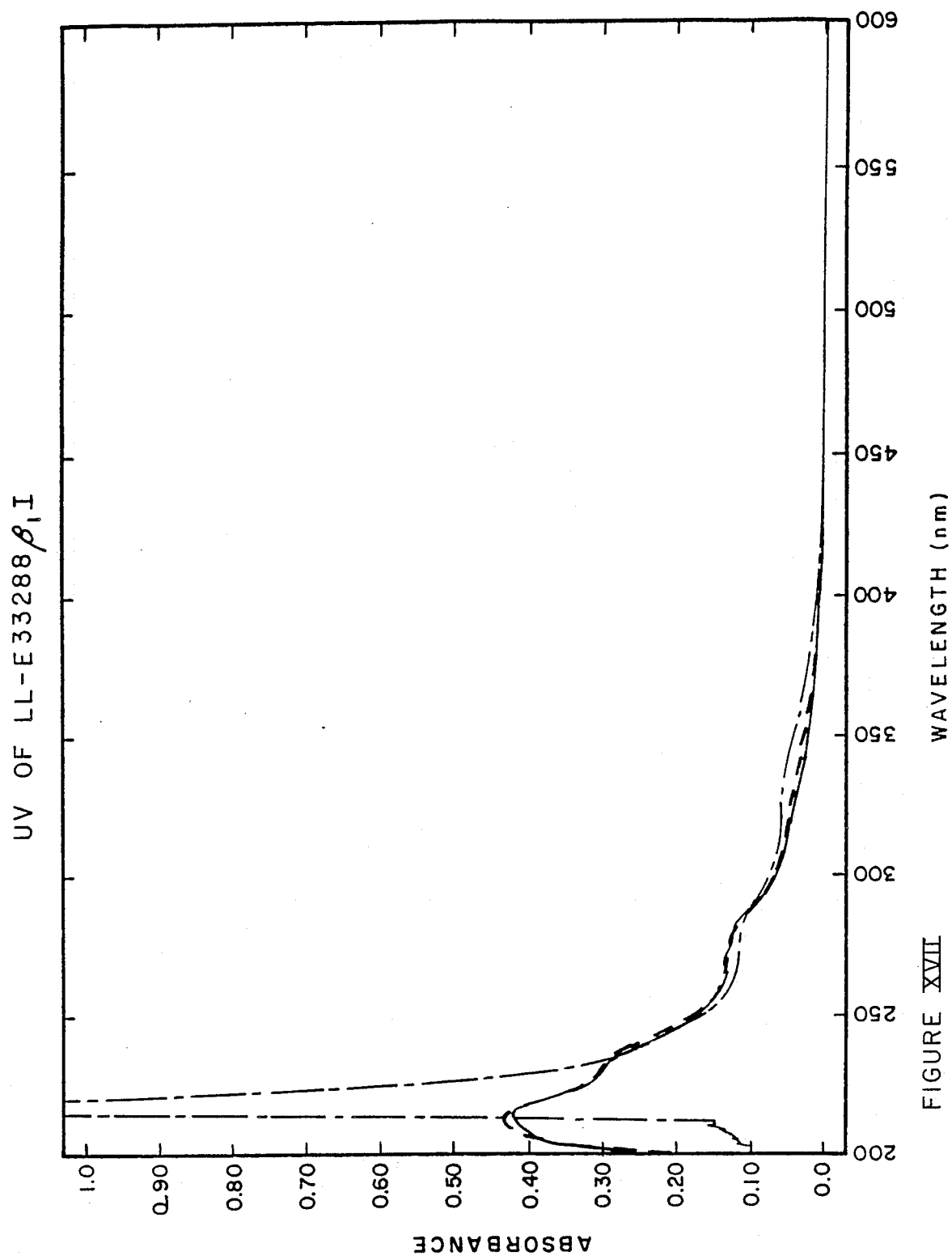

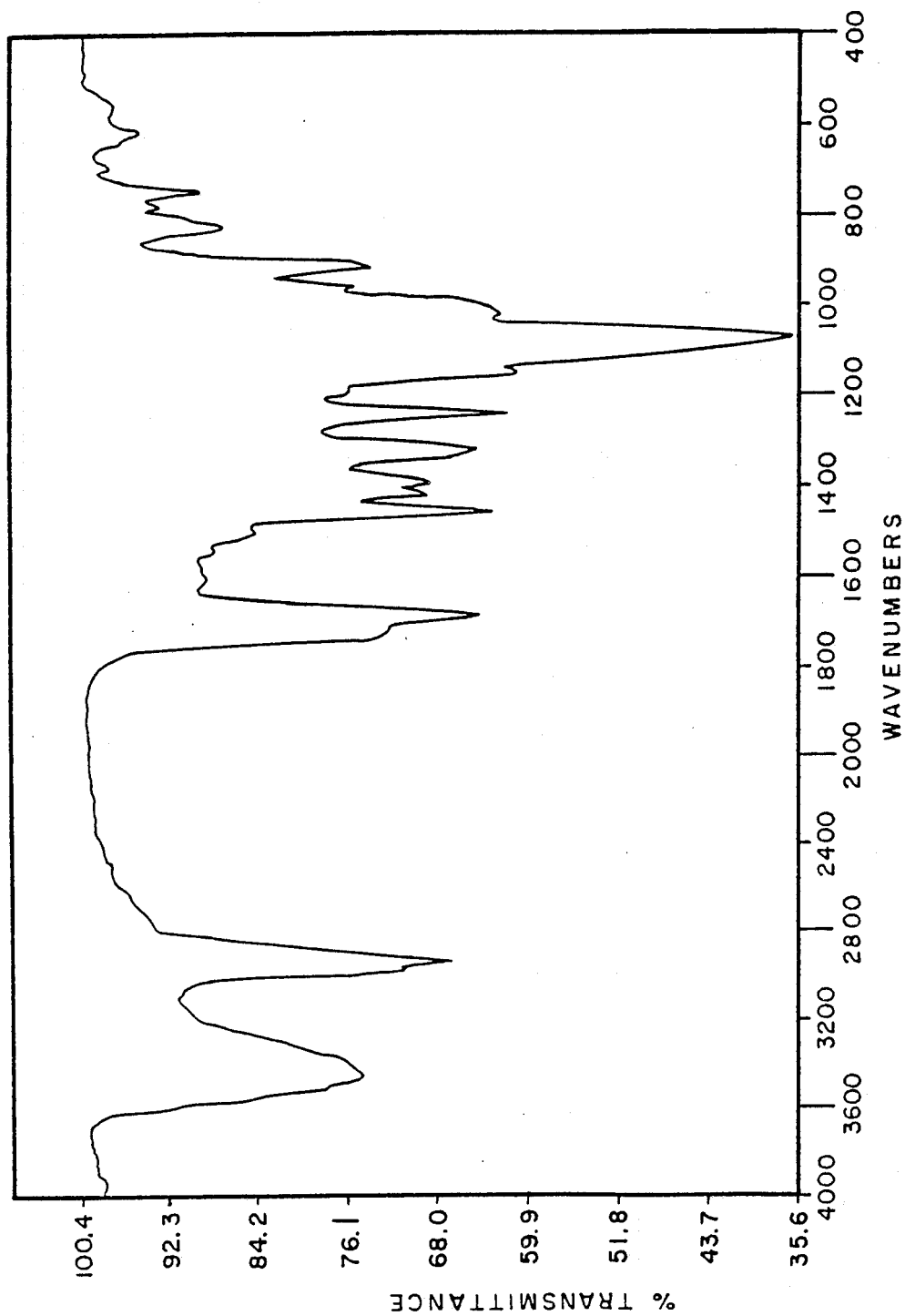
FIGURE XVIII

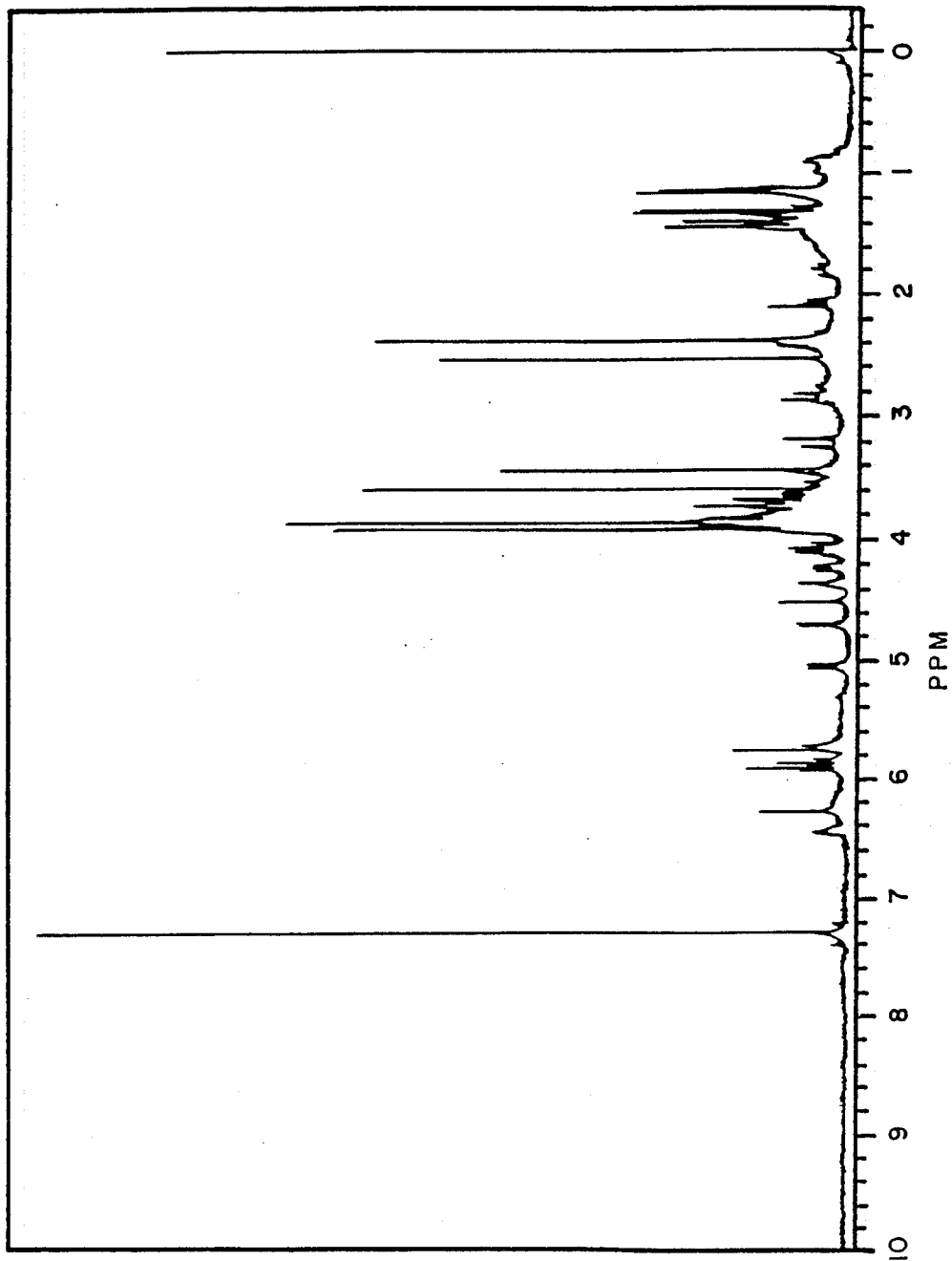
FIGURE XIX

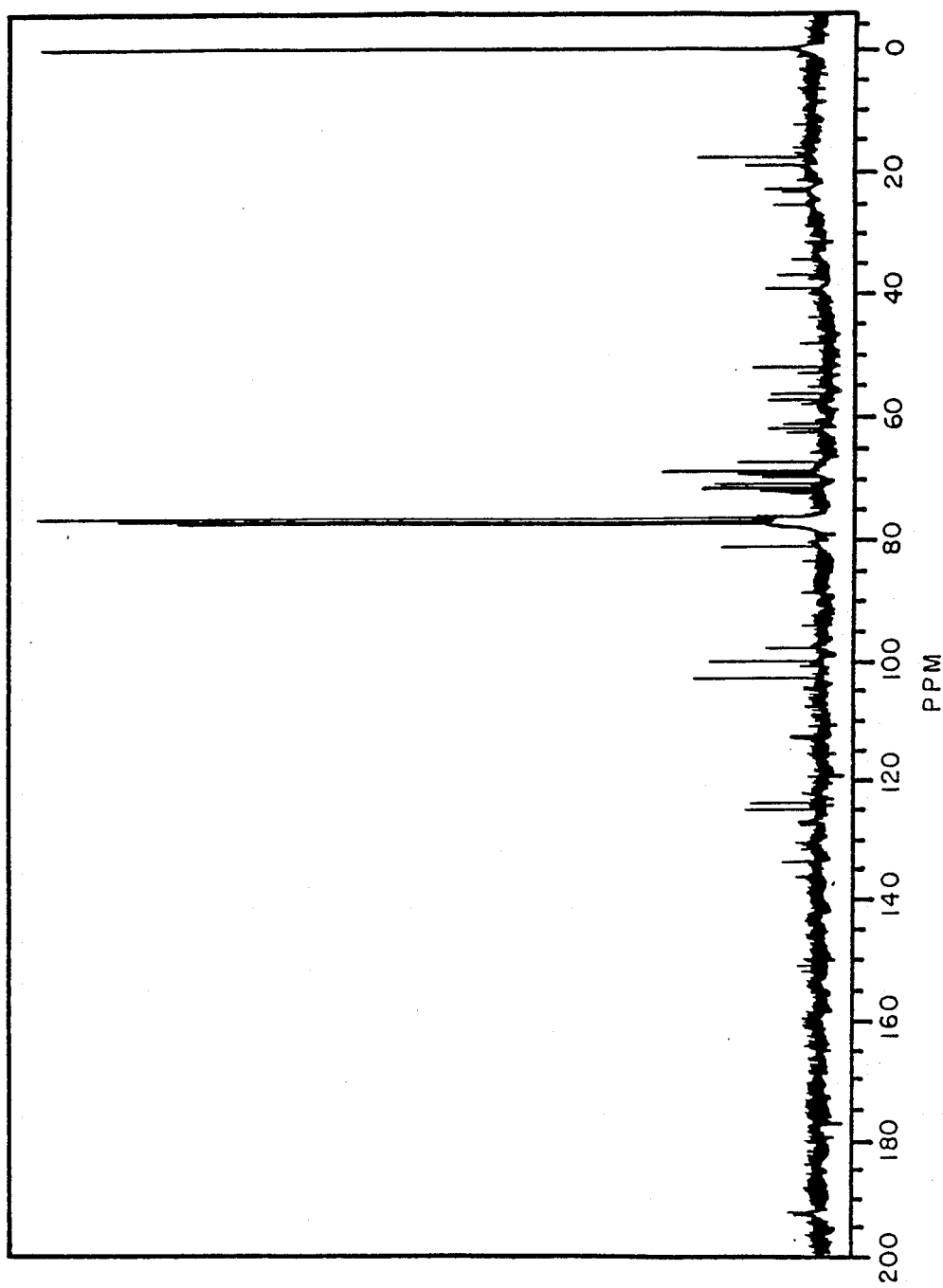

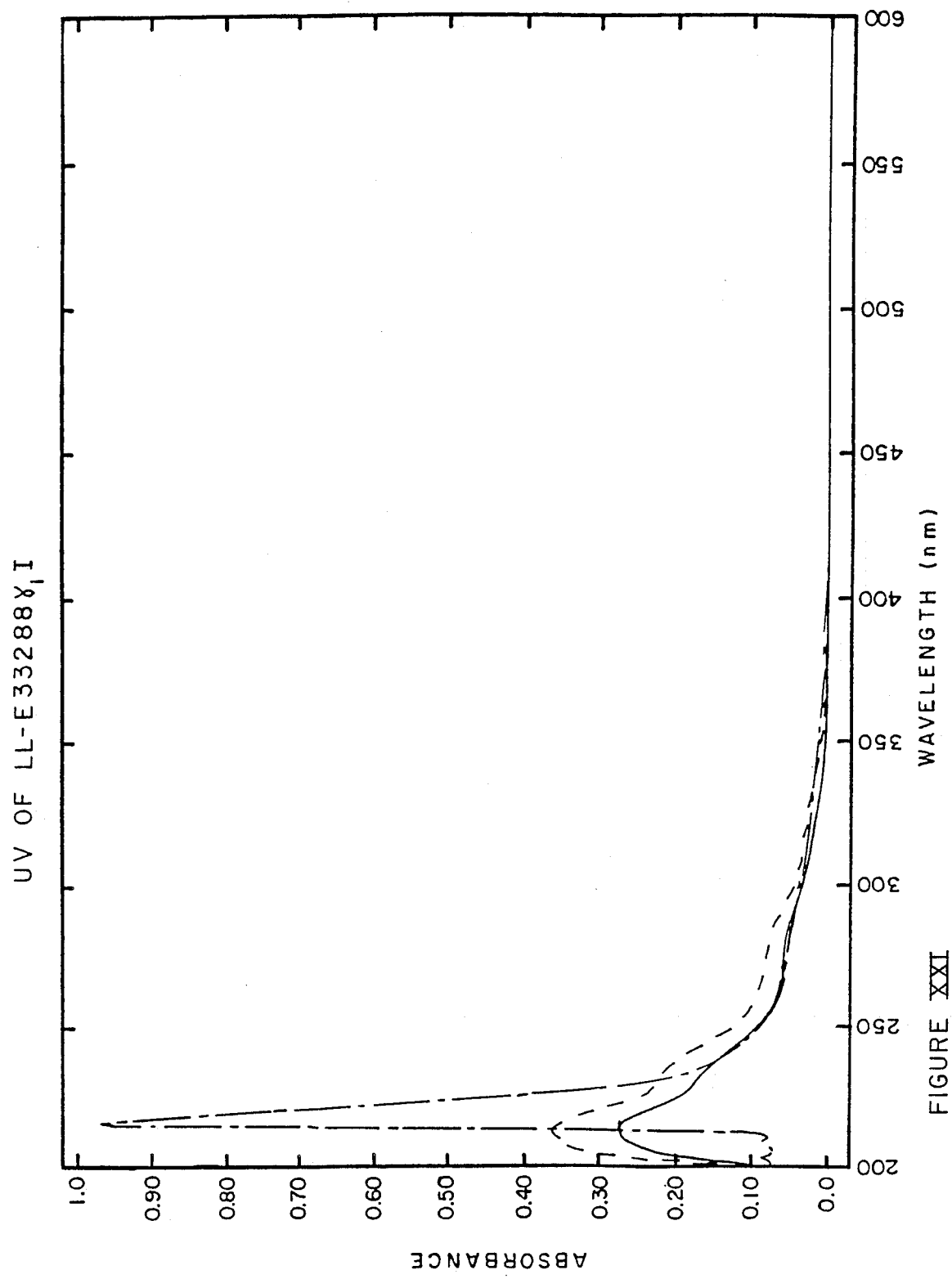
FIGURE XXI

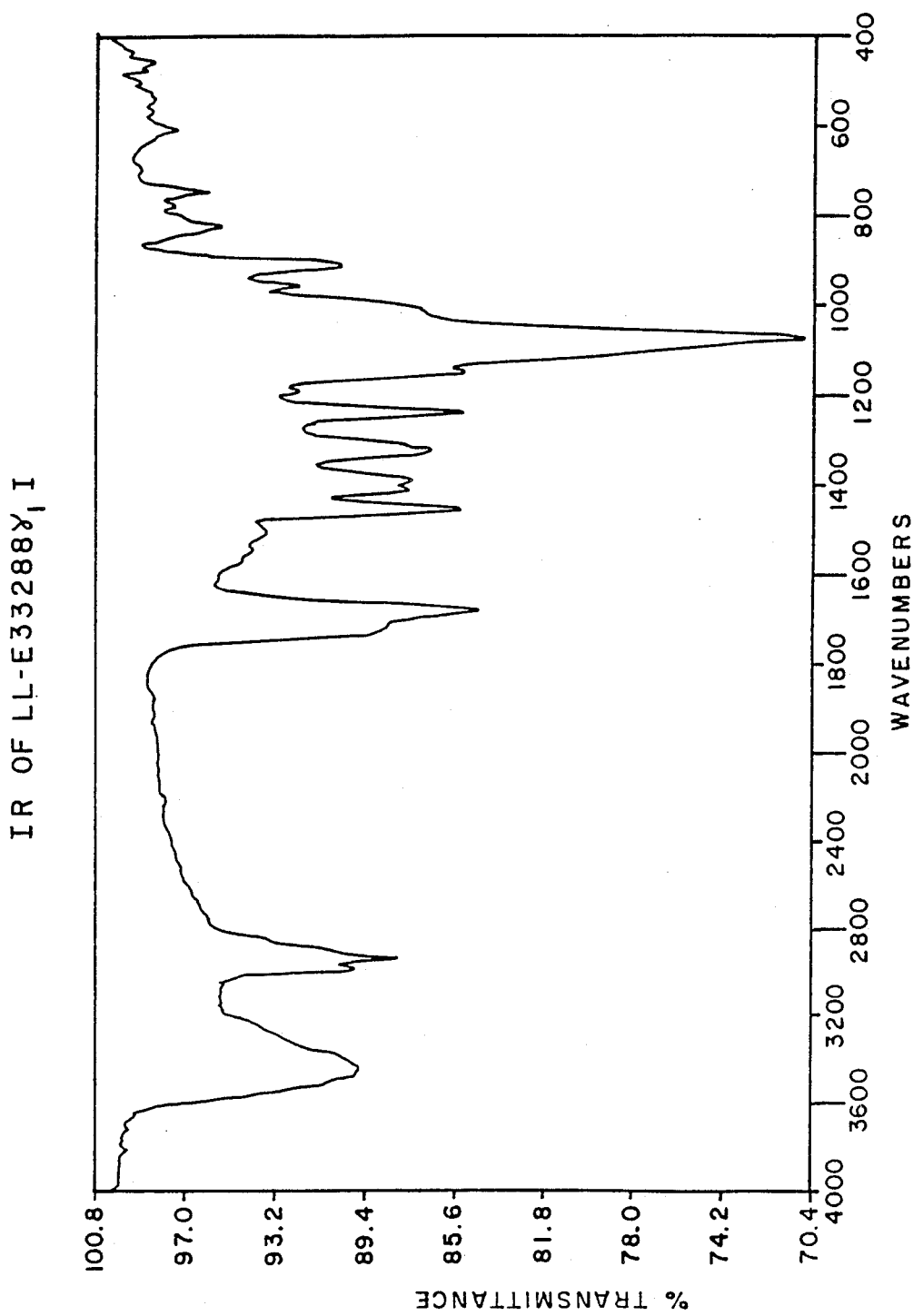
FIGURE XXII

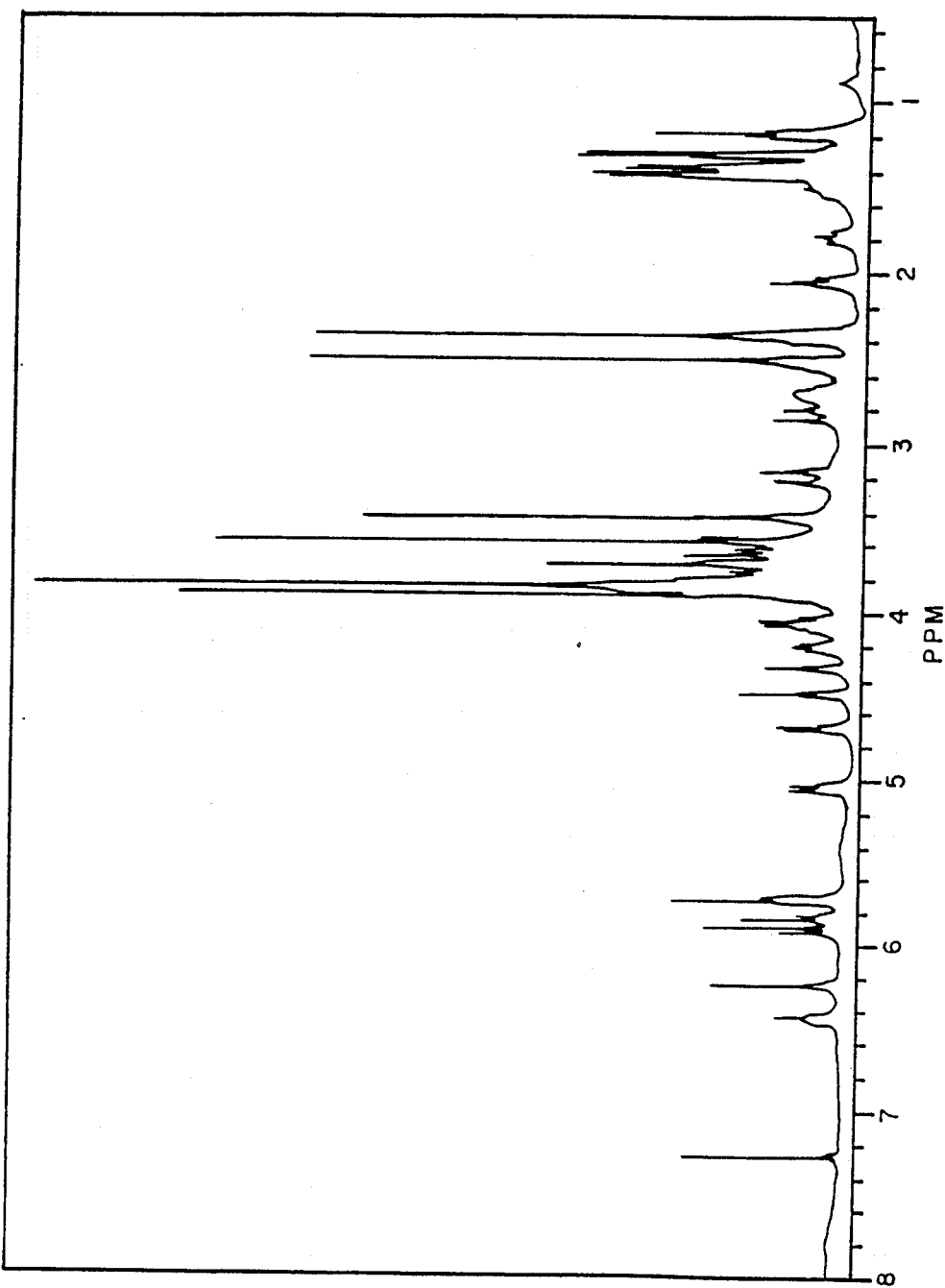
FIGURE XXIII

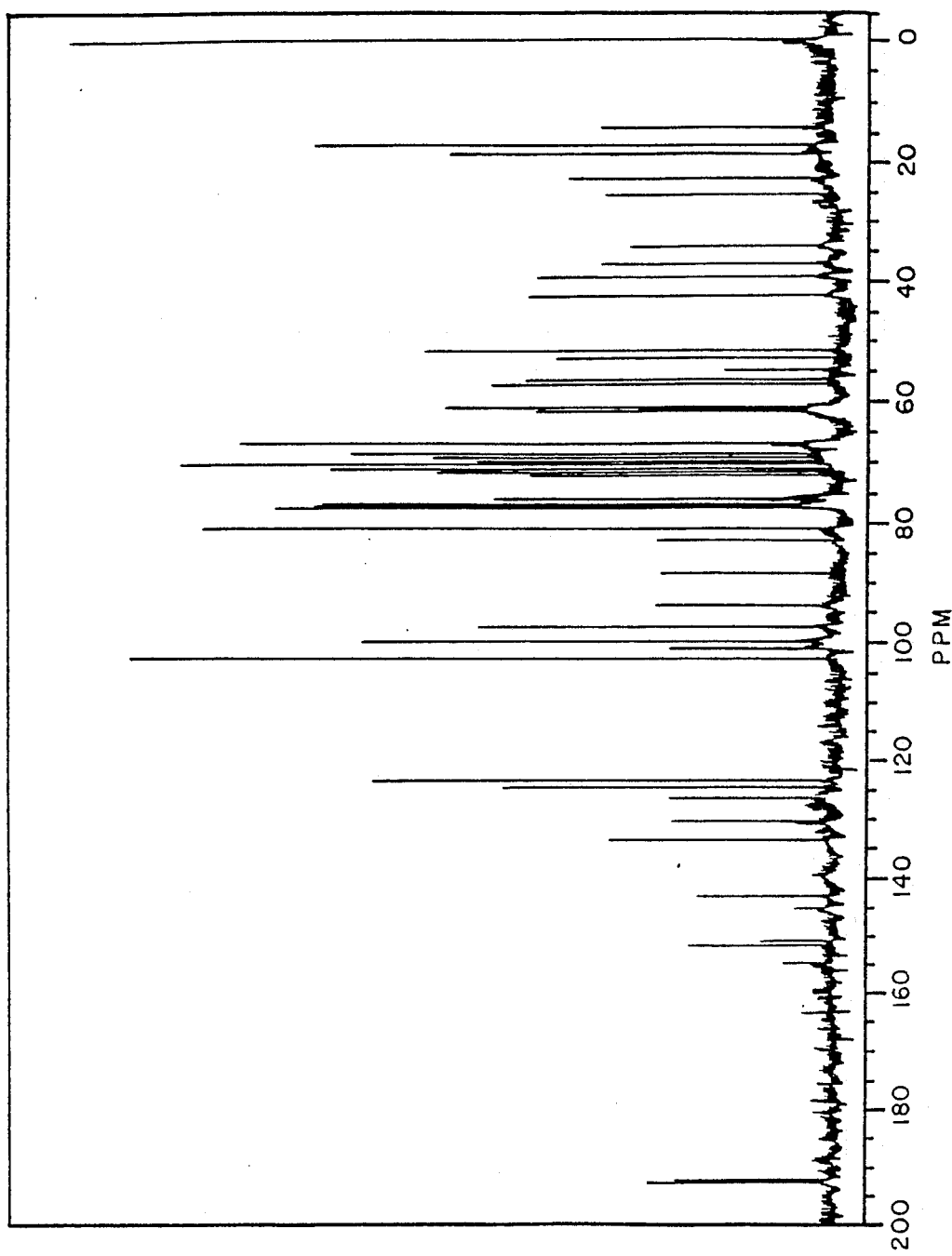
FIGURE XXIV

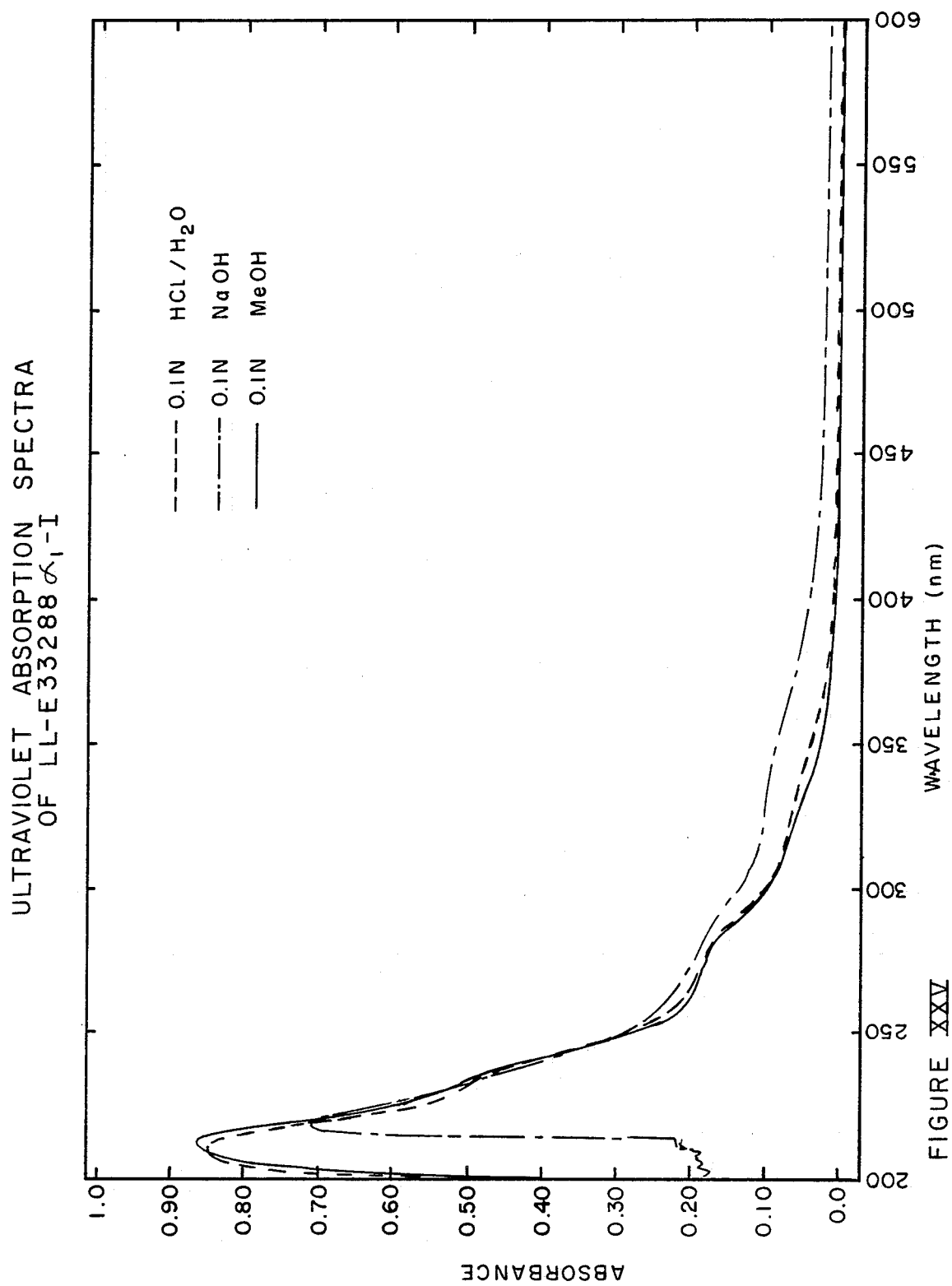
FIGURE XXV

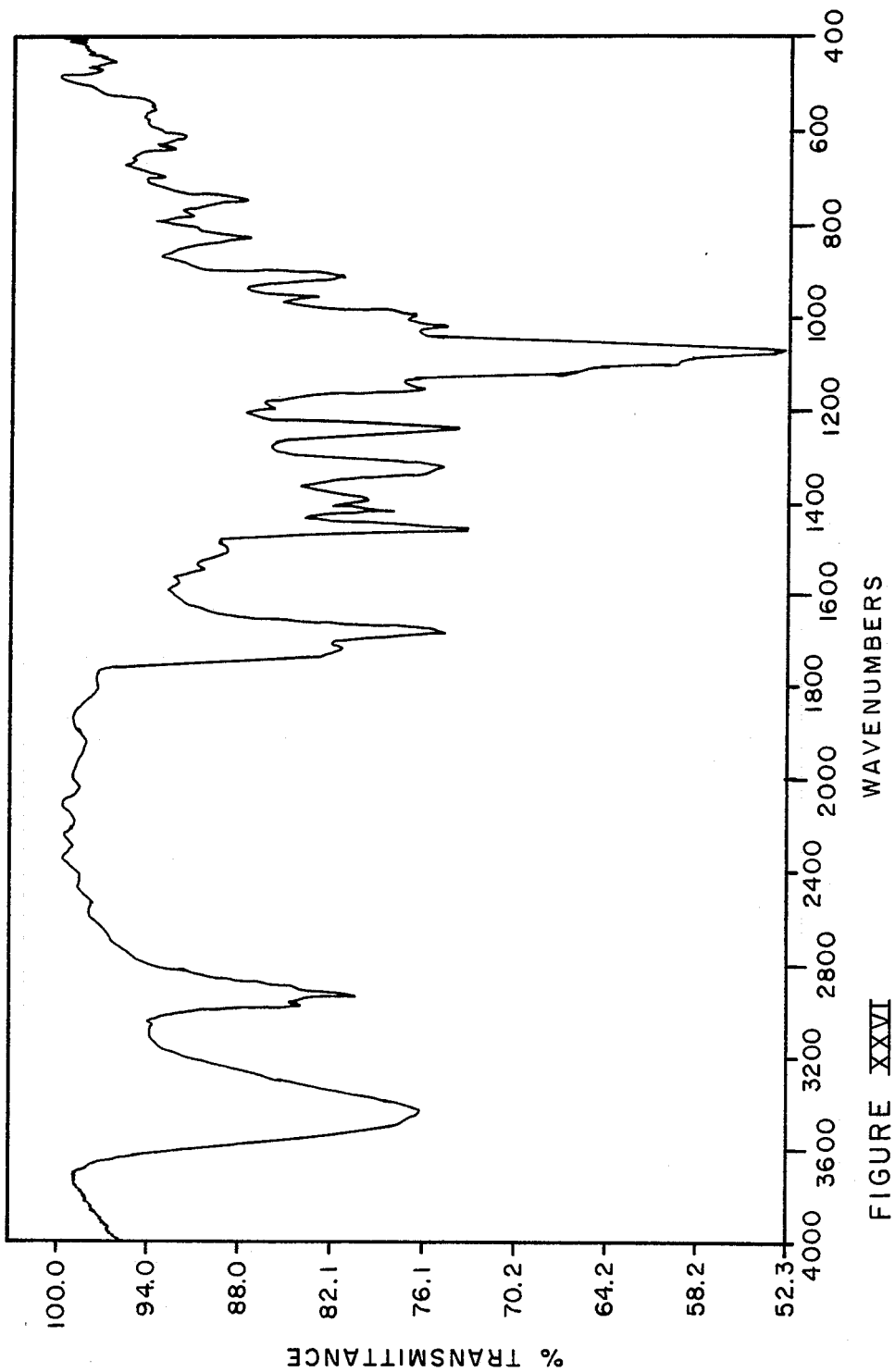
FIGURE XXVI

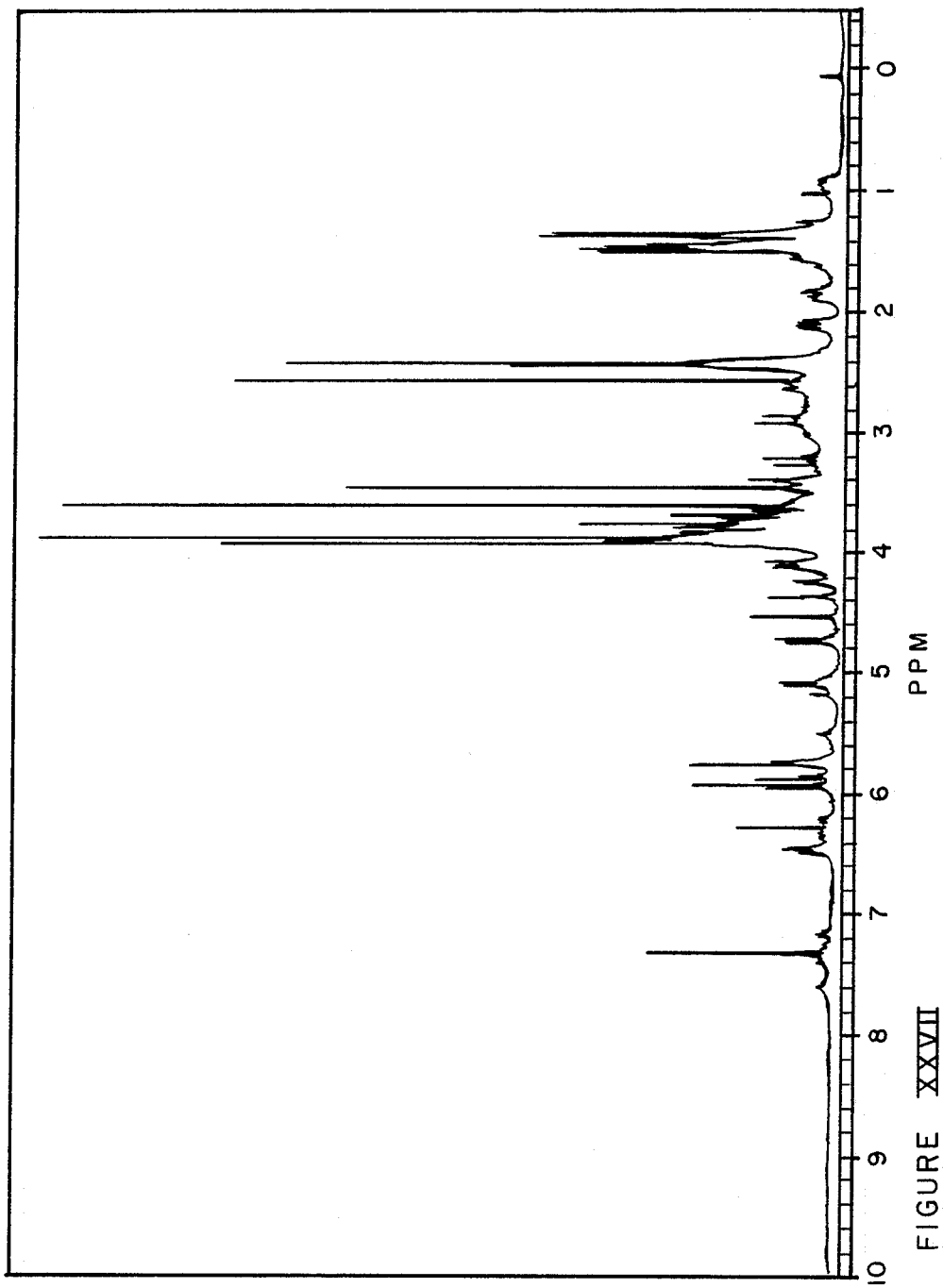

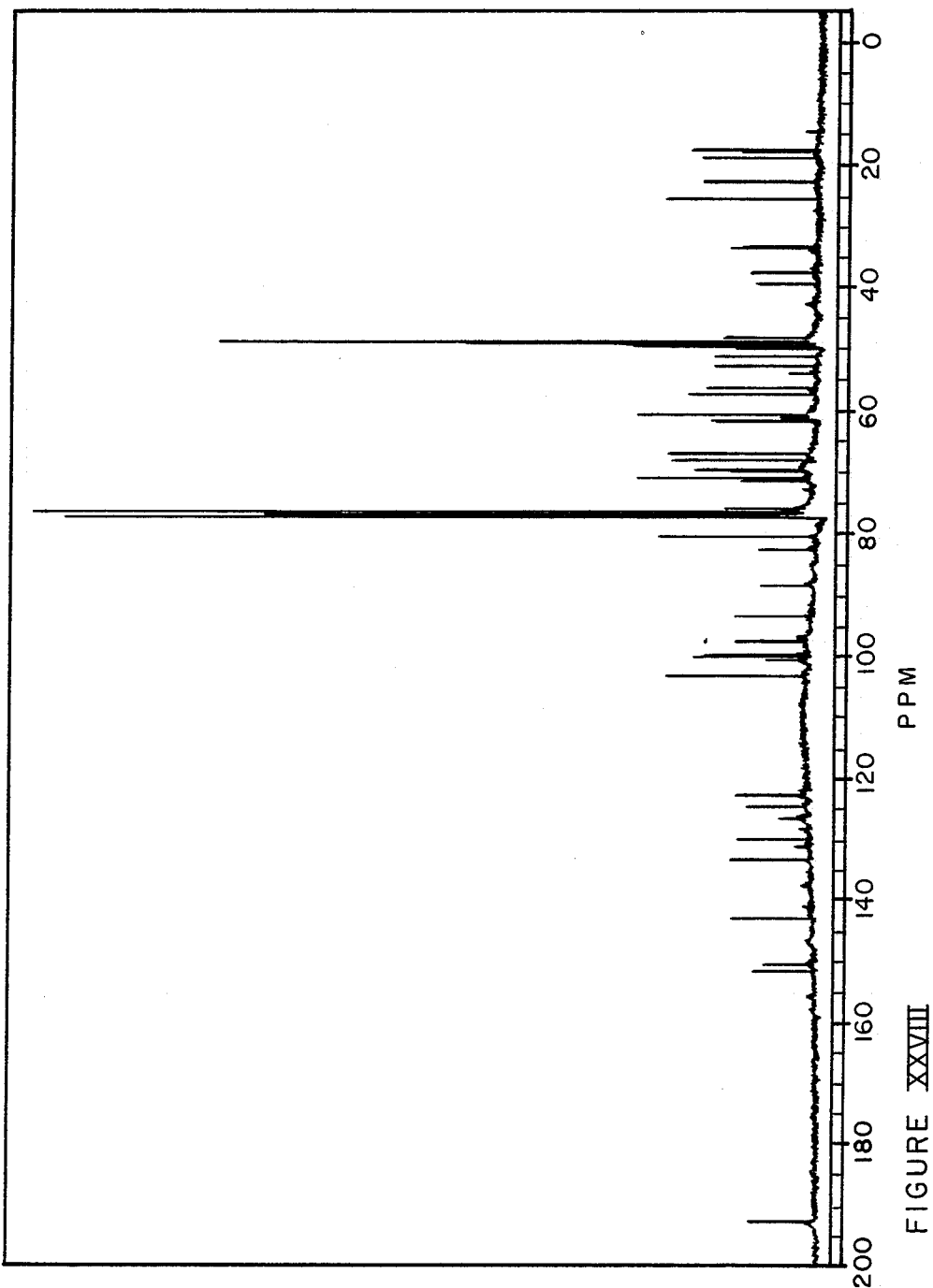

ANTITUMOR ANTIBIOTICS (LL-E33288 COMPLEX)

SUMMARY OF THE INVENTION

This application is a continuation-in-part of co-pending application Ser. No. 787,066, filed Oct. 17, 1985, which is a continuation-in-part of co-pending application Ser. No. 672,031, filed Nov. 16, 1984 and now abandoned.

This invention relates to new antibacterial and antitumor agents designated LL-E33288$\alpha_1$-Br, LL-E33288$\alpha_1$-I, LL-E33288$\alpha_2$-Br, LL-E33288$\alpha_2$-I, LL-E33288$\alpha_3$-Br, LL-E33288$\alpha_3$-I, LL-E33288$\alpha_4$-Br, LL-E33288$\beta_1$-Br, LL-E33288$\beta_1$-I, LL-E33288$\beta_2$-Br, LL-E33288$\alpha_2$-I, LL-E33288$\gamma_1$-Br, LL-E33288$\gamma_1$-I and LL-E33288$\delta_1$-I, to their production by fermentation, to methods for their recovery and concentration from crude solutions and to processes for their purification. The present invention includes within its scope the anti-bacterial and anti-tumor agents in dilute form, as crude concentrates, as a complex of various or all components, in pure form as individual components and novel strains of Micromonospora.

The LL-E33288 antibiotics of this invention are closely related compounds. The fourteen antibiotics are recovered from fermentation and are initially obtained as a mixture, hereinafter either the LL-E33288 complex, the LL-E33288 Iodo-complex or the LL-E33288 Bromo-complex. In general, the iodine containing components of the LL-E33288 antibiotics (e.g., $\alpha_1$-I, $\alpha_2$-I, $\alpha_3$-I, $\beta_1$-I, $\beta_2$-I, $\gamma_1$-I and $\delta_1$-I) are found only in fermentations using media containing inorganic or organic iodide while the bromine containing components (e.g., $\alpha_1$-Br, $\alpha_2$-Br, $\alpha_3$-Br, $\alpha_4$-Br, $\beta_1$-Br, $\beta_2$-Br and $\gamma_1$-Br) are found only in fermentations using media containing inorganic or organic bromide. While the ratio of components in the LL-E33288 complex will vary, depending upon the fermentation of both the bromine and the iodine containing antibiotics, LL-E33288$\beta_1$ and LL-E33288$\gamma_1$ are generally the major components, together accounting for approximately 90% of the complex. LL-E33288$\alpha_1$, LL-E33288$\alpha_2$, LL-E33288$\alpha_3$, LL-E33288$\alpha_4$-Br, LL-E33288$\beta_2$ and LL-E33288$\delta_1$-I are minor components, together accounting for approximately 10% of the complex.

The LL-E33288 antibiotics are active against grampositive and gram-negative bacteria. Each of the components were also found to be active in a modification of the Biochemical Induction Assay [Elespuru, R. and Yarmolinsky, M., Environmental Mutagenesis, 1, 65–78 1979)], a test which specifically measures the ability of an agent to directly or indirectly initiate DNA damage. In this assay, both LL-E33288$\beta_1$-Br and LL-E332871$\gamma_1$-Br were active at concentrations lower than $1 \times 10^{-6}$ mcg/ml.

BRIEF DESCRIPTION OF THE DRAWINGS

FIG. I is the ultraviolet absorption spectra of LL-E33288$\beta_1$-Br;

FIG. II is the infrared absorption spectrum of LL-E33288$\beta_1$-Br;

FIG. III is the proton magnetic resonance spectrum of LL-E33288$\beta_1$-Br;

FIG. IV is the carbon 13 magnetic resonance spectrum of LL-E33288$\beta_1$-Br;

FIG. V is the ultraviolet absorption spectra of LL-E33288$\gamma_1$-Br;

FIG. VI is the infrared absorption spectrum of LL-E33288$\gamma_1$-Br;

FIG. VII is the proton magnetic resonance spectrum of LL-E33288$\gamma_1$-Br;

FIG. VIII is the carbon 13 magnetic resonance spectrum of LL-E33288$\gamma_1$-Br;

FIG. IX is the ultraviolet absorption spectra of LL-E33288$\alpha_2$-I;

FIG. X is the infrared absorption spectrum of LL-E33288$\alpha_2$-I;

FIG. XI is the proton magnetic resonance spectrum of LL-E33288$\alpha_2$-I;

FIG. XII is the carbon 13 magnetic resonance spectrum of LL-E33288$\alpha_2$-I;

FIG. XIII is the ultraviolet absorption spectra of LL-E33288$\alpha_3$-I;

FIG. XIV is the infrared absorption spectrum of LL-E33288$\alpha_3$-I;

FIG. XV is the proton magnetic resonance spectrum of LL-E33288$\alpha_3$-I;

FIG. XVI is the carbon 13 magnetic resonance spectrum of LL-E33288$\alpha_3$-I;

FIG. XVII is the ultraviolet spectra of LL-E33288$\beta_1$-I;

FIG. XVIII is the infrared absorption spectrum of LL-E33288$\beta_1$-I;

FIG. XIX is the proton magnetic resonance spectrum of LL-E33288$\beta_1$-I;

FIG. XX is the carbon 13 magnetic resonance spectrum of LL-E33288$\beta_1$-I;

FIG. XXI is the ultraviolet absorption spectra of LL-E33288$\gamma_1$-I;

FIG. XXII is the infrared absorption spectrum of LL-E33288$\gamma_1$-I;

FIG. XXIII is the proton magnetic resonance spectrum of LL-E33288$\gamma_1$-I;

FIG. XXIV is the carbon 13 magnetic resonance spectrum of LL-E33288$\gamma_1$-I;

FIG. XXV is the ultraviolet absorption spectra of LL-E33288$\delta_1$-I;

FIG. XXVI is the infrared absorption spectrum of LL-E33288$\delta_1$-I;

FIG. XXVII is the proton magnetic resonance spectrum of LL-E33288$\delta_1$-I; and FIG. XXVIII is the carbon 13 magnetic resonance spectrum of LL-E33288$\delta_1$-I.

DETAILED DESCRIPTION OF THE INVENTION

The physico-chemical characteristics of LL-E33288$\beta_1$-Br and LL-E33288$\gamma_1$-Br are described below:

LL-E33288$\beta_1$-Br (1) Approximate elemental analysis: C 48.6; H 5.6; N 2.9; S 9.1; and Br 5.5. (It has been determined by electron spectroscopy for chemical analysis (ESCA) that only the following elements are present: C, H, N, O, S and Br);

(2) Melting point: 146°–150° C. (dec.);

(3) Specific rotation: $[\alpha]_D^{26} = -49° \pm 10°$ (0.1% ethanol;

(4) Ultraviolet absorption spectra: as shown in FIG. I (methanol; acidic methanol; basic methanol);

(5) Infrared absorption spectrum: as shown in FIG. II (KBr disc);

(6) Proton magnetic resonance spectrum: as shown in FIG. III (300 MHz, CDCl$_3$);

(7) Carbon-13 magnetic resonance spectrum: as shown in FIG. IV (75.43 MHz, CDCl$_3$, ppm from TMS), significant peaks as listed below:

| | | | |
|---|---|---|---|
| 17.60(q); | 17.64(q); | 18.9(q); | 19.7(q); |
| 22.3(q); | 22.8(q); | 23.5(q); | 34.3(t); |
| 36.9(t); | 39.2 (t/d); | 47.8(d); | 51.7(q); |
| 52.7(q); | 54.6 (t/d); | 56.3(q); | 57.2(q); |
| 57.8(d); | 61.0 (q/d); | 61.7(d); | 62.4(t); |
| 66.9(d); | 68.4(d); | 69.1(d); | 69.7(d); |
| 70.2(d); | 71.1(d); | 71.9(d); | 72.1(s/t); |
| 76.1(d); | 81.0(d); | 83.3(s); | 88.2(s); |
| 97.4(d); | 99.7(d); | 100.8(s); | 102.5(d); |
| 115.1(s); | 123.4(d); | 124.4(d); | 126.5(d); |
| 130.2(s); | 130.8(s); | 144.6(s); | 149.3(s); |
| 149.5(s); | 191.7(s); | 192.4(s). | |

(8) Molecular weight: 1333/1335 respectively for $^{79}$Br/$^{81}$Br as determined by FAB-MS; and (9) Molecular formula: C$_{56}$H$_{76}$N$_3$O$_{21}$S$_4$Br, exact masses at 1258.3699 ($^{79}$Br) and 1260.3726($^{81}$Br) was determined by high resolution FAB-MS and calculated to be C$_{55}$H$_{76}$N$_3$O$_{21}$S$_2$Br (M+H-CS$_2$).

LL-E33288$\gamma_1$-Br (1) Ultraviolet absorption spectra: as shown in FIG. V (methanol; acidic methanol; basic methanol);

(2) Infrared absorption spectrum: as shown in FIG. VI (KBr disc):

(3) Proton magnetic resonance spectrum: as shown in FIG. VII (300 MHz, CDCl$_3$);

(4) Carbon 13 magnetic resonance spectrum: as shown in FIG. VIII (75.43 MHZ, CDCl$_3$, ppm from TMS), significant peaks as listed below:

| | | | |
|---|---|---|---|
| 14.4 | 17.6 | 17.9 | 19.0 |
| 19.7 | — | 22.8 | — |
| — | 34.0 | 37.6 | 39.5 |
| 42.1 | — | 51.6 | 52.7 |
| 54.1 | 56.3 | 57.3 | — |
| 59.3 | 61.1 | 61.8 | 61.9 |
| 67.2 | 68.18 | 68.23 | 69.7 |
| 70.1 | 70.8 | 71.1 | 71.7 |
| 71.8 | 76.1 | — | 81.0 |
| 82.9 | 88.4 | — | 97.8 |
| 100.0 | 100.2 | 101.3 | 103.0 |
| 115.3 | 123.0 | 124.9 | 126.9 |
| 130.4 | 131.1 | 131.8 | 138.0 |
| 144.7 | — | 149.5 | 149.6 |
| 155.6 | 192.5 | 192.9 | |

(5) Molecular formula: C$_{55}$H$_{74}$N$_3$O$_{21}$S$_4$Br by comparing its UV, IR, $^1$HPMR, and $^{13}$CNMR data to those of LL-E33288$\gamma_1$-I; and (6) Molecular weight: 1319/1321 respectively for $^{79}$Br/$^{81}$Br, calculated from its molecular formula.

The physico-chemical characteristics of LL-E33288$\alpha_1$-I, LL-E33288$\alpha_2$-I; LL-E33288$\alpha_3$-I, and LL-E33288$\beta_1$-I, LL-E33288$\gamma_1$-I and LL-E33288$\delta_1$-I are described below:

LL-E33288$\alpha_1$-I (1) Molecular weight: 1145, determined by FAB-MS.

LL-E33288$\alpha_2$-I (1) Contains and only contains the following elements by electron spectroscopy for chemical analysis (ESCA): C, H, N, O, S, I;

(2) Molecular weight: 1207 (M-CS$_2$ at 1131 was observed by FAB-MS);

(3) Ultraviolet absorption spectra: as shown in FIG. IX (Methanol, acidic methanol, basic methanol);

(4) Infrared absorption spectrum: as shown in FIG. X (KBr disc);

(5) Proton magnetic resonance spectrum: as shown in FIG. XI (300 MHz, CDCl$_3$);

(6) Carbon-13 magnetic resonance spectrum: as shown in FIG. XII (75.43 MHz, CDCl$_3$, ppm from TMS), significant peaks as listed below:

| | | | |
|---|---|---|---|
| 17.7 | 56.3 | 71.8 | 122.7 |
| 18.8 | 60.7 | 73.7 | 125.1 |
| 22.7 | 61.4 | 79.0 | 126.3 |
| 24.7 | 60.7 | 82.6 | 127.1 |
| 33.1 | 67.7 | 87.4 | 133.1 |
| 37.4 | 67.9 | 85.4 | 137.0 |
| 39.6 | 69.6 | 98.0 | 137.1 |
| 41.4 | 69.7 | 100.4 | 149.2 |
| 51.3 | 70.3 | 100.1 | 151.5 |
| 53.3 | 71.0 | 100.8 | 192.8 |
| 53.8 | 73.4 | 98.2 | 193.2 |

(7) Molecular formula: C$_{48}$H$_{62}$N$_3$O$_{17}$S$_4$I: by comparing its UV, IR, $^1$HNMR and $^{13}$CNMR data to those of LL-E33288$\gamma_1$-I LL-E33288$\alpha_3$-I (1) Ultraviolet absorption spectra: as shown in FIG. XIII (methanol; acidic methanol, basic methanol);

(2) Infrared absorption spectrum: as shown in FIG. XIV (KBr disc);

(3) Proton Magnetic resonance spectrum: as shown in FIG. XV (300 MHz, CDCl$_3$);

(4) Carbon-13 magnetic resonance spectrum: as shown in FIG. XVI (75.43 MHz, CDCl$_3$, ppm from TMS), significant peaks as listed below:

| | | |
|---|---|---|
| 17.5(q) | 69.5(d) | 103.1(d) |
| 18.0(q) | 70.0(d) | 123.4(d) |
| 19.0(q) | 70.1(d) | 124.7(d) |
| 22.7(q) | 70.8(d) | 127.3(d) |
| 25.3(q) | 70.9(d) | 131.1 |
| 37.4(t) | 72.1(s) | 130.4(s) |
| 39.2(t) | 71.3(d) | 133.5(s) |
| 51.5(d) | 74.5(d) | 136.8(s) |
| 53.3(q) | 80.8(d) | 143.0(s) |
| 53.7(t) | 83.1(s) | 145.8 |
| 57.2(q) | 87.6(s) | 150.5(s) |
| 61.0(q) | 93.7(s) | 151.6(s) |
| 61.8(q) | 98.6(s) | 154.7(s) |
| 67.1(d) | 100.1(d) | 192.4(s) |
| 67.3(d) | 101.0(s) | 192.6(s) |
| 68.0(d) | 103.4(d) | |

(5) Molecular formula: C$_{47}$H$_{59}$N$_2$O$_{19}$S$_4$I by comparing its UV, IR, $^1$HNMR and $^{13}$CNMR data to those of LL-E33288$\gamma_1$-I; and (6) Molecular weight: 1210, calculated from molecular formula.

LL-E33288$\beta_1$-I (1) Ultraviolet absorption spectra: as shown in FIG. XVII (methanol; acidic methanol; basic methanol);

(2) Infrared absorption spectrum: as shown in FIG. XVIII (KBr disc);

(3) Proton magnetic resonance spectrum: as shown in FIG. XIX (300 MHz, CDCl$_3$);

(4) Carbon 13 magnetic resonance spectrum: as shown in FIG. XX (75.43 MHz, CDCl$_3$, ppm from TMS), significant peaks as listed below:

| | | | |
|---|---|---|---|
| — | 17.5 | 17.6 | 18.9 |
| — | 22.4 | 22.8 | 23.4 |
| 25.4 | 34.3 | 36.9 | 39.2 |

| | | | |
|---|---|---|---|
| — | 47.9 | 51.6 | 52.8 |
| 54.8 | 56.3 | 57.2 | 57.9 |
| 60.9 | — | 61.6 | 62.2 |
| 67.0 | 68.4 | 68.4 | 69.1 |
| 69.6 | 70.4 | 71.1 | 71.8 |
| 72.2 | 76.2 | — | 80.8 |
| 83.3 | 88.1 | 93.6 | 97.4 |
| 99.6 | 99.6 | — | 102.6 |
| 112.4 | 123.4 | 124.4 | 126.4 |
| — | — | 133.4 | — |
| — | — | — | — |
| — | 192.2 | 192.6 | — |

(5) Molecular formula: $C_{56}H_{76}N_3O_{21}S_4I$ by comparing its UV, IR, $^1$HPMR and $^{13}$CNMR data to those of LL-E33288$\gamma_1$-I; and (6) Molecular weight: 1381, calculated from molecular formula.

LL-E33288$\gamma_1$-I (1) Contains and only contains the following element by electron spectroscopy for chemical analysis (ESCA): C,H,N,O,S,I;

(2) Approximate elemental analysis: C 48.8; H 5.4; N 2.8; S 9.0; I 9.2;

(3) Molecular weight: 1367, determined by FAB-MS;

(4) Molecular formula: $C_{55}H_{74}N_3O_{21}S_4I$, exact mass for M+H was determined by high resolution FAB-MS to be 1368. 3397 for $C_{55}H_{75}N_3O_{21}S_4I$;

(5) Ultraviolet absorption spectra: as shown in FIG. XXI (methanol; acidic methanol; basic methanol);

(6) Infrared absorption spectrum: as shown in FIG. XXII (KBr disc);

(7) Proton magnetic resonance spectrum: as shown in FIG. XXIII (300 MHz, CDCl$_3$); and (8) Carbon 13 magnetic resonance spectrum: as shown in FIG. XXIV (75.43 MHz, CDCl$_3$, ppm for TMS) significant peaks as listed below:

| | | | |
|---|---|---|---|
| 14.5(q) | 17.6(q) | 17.6(q) | 18.9(q) |
| — | — | 22.8(q) | — |
| 25.4(q) | 34.1(t) | 37.0(t) | 39.1(t) |
| 42.3(t/s) | — | 51.5(d) | 52.8(q) |
| 54.8(t) | 56.3(q) | 57.2(q) | — |
| 60.4(d) | 60.9(q) | 61.3(d) | 61.7(q) |
| 67.0(d) | 68.4(d) | 68.5(d) | 69.2(d) |
| 69.7(d) | 70.5 | 71.1(d) | 71.8(d) |
| 72.1(s) | 75.7(d) | 75.8(d) | 80.9(d) |
| 82.8(s) | 88.1(s) | 93.5(s) | 97.3(d) |
| 99.6(d) | 99.7(d) | 100.8(s) | 102.6(d) |
| — | 123.4(d) | 124.4(d) | 126.2(d) |
| 103.2(s) | 131.0(s) | 133.4(s) | 139.1(s) |
| 143.0(s) | 145.1 | 150.6(s) | 151.5(s) |
| 154.5 | 192.0(s) | 192.5(s) | |

LL-E33288$\delta_1$-I (1) Ultraviolet absorption spectra: as shown in FIG. XXV (methanol, acidic methanol, basic methanol);

(2) Infrared absorption spectrum: as shown in FIG. XXVI (KBr disc);

(3) Proton magnetic resonance spectrum: as shown in FIG. XXVII (300 MHz, CDCl$_3$); and (4) Carbon 13 magnetic resonance spectrum: as shown in FIG. XXVIII (75.43 MHz, CDCl$_3$, ppm for TMS), significant peaks as listed below:

| | | |
|---|---|---|
| 17.2 | 60.4 | 99.6 |
| 17.6 | 66.8 | 103.0 |
| 18.5 | 67.7 | 122.7 |
| 22.4 | 69.5 | 124.7 |
| 25.0 | 69.8 | 126.6 |
| 33.0 | 70.6 | 130.7 |
| 37.3 | 70.7 | 130.1 |
| 39.0 | 71.1 | 133.2 |
| 33.5 | 71.3 | 137.7 |
| 51.0 | 76.0 | 142.8 |
| 52.4 | 80.4 | 150.3 |
| 53.6 | 82.5 | 151.5 |
| 56.1 | 88.1 | 155.5 |
| 57.0 | 93.4 | 192.7 |
| 61.0 | 97.5 | 192.8 |
| 60.6 | 100.9 | |
| 61.4 | 99.8 | |

The LL-E33288 components are most conveniently separated and identified by high-performance liquid chromatography (HPLC) and by thin-layer chromatography (TLC). It is difficult, although not impossible, to separate the corresponding iodinated and brominated components by HPLC; however, they cannot be distinguished by TLC.

The preferred analytical separation of the LL-E33288-Br components by HPLC uses the following conditions:

Column: "Sepralyte $C_{18}$ 5 m," 4.6 mm×25 cm (Analytichem International);

Solvent: Acetonitrile: 0.2M aqueous ammonium acetate (60:40);

Flow rate: 1.5 ml/minute

Detector: Dual wavelength UV at 254 nm and 280 nm;

Sensitivity: 0–0.02 A.U.F.S.

Table IA gives the approximate retention times and volumes of LL-E33288$\beta_1$-Br, LL-E33288$\beta_2$-Br, and LL-E33288$\gamma_1$-Br under these conditions.

TABLE IA

| LL-E33288 Components | Retention Time (minutes) | Retention Volume (ml) |
|---|---|---|
| $\beta_1$-Br | 5.7 | 8.6 |
| $\beta_2$-Br | 7.1 | 10.7 |
| $\gamma_1$-Br | 4.3 | 6.5 |

The preferred analytical HPLC separation of the iodine containing LL-E33288 components uses the following conditions:

Column: NOVA-PAK $C_{16}$ Radial-PAK cartridge with RCM-100 Radial Compression Module (Millipore, Waters Chromatography Division);

Solvent: Acetonitrile: 0.2M aqueous ammonium acetate (50:50);

Flow Rate: 1.2 ml/minute;

Detector: Dual wavelength UV at 254 nm and 280 nm;

Sensitivity: 0–0.02 A.U.F.S.

Table IB gives the approximate retention times and volumes of LL-E33288$\alpha_1$-I, LL-E33288$\alpha_2$-I, LL-E33288$\alpha_3$-I, LL-E33288$\beta_1$-I, LL-E33288$\beta_2$-I LL-E33288$\gamma_1$-I and LL-E33288$\delta_1$-I under these conditions.

TABLE IB

| LL-E33288 Components | Retention Time (minutes) | Retention Volume (ml) |
|---|---|---|
| $\alpha_1$-I | 11.9 | 14.3 |
| $\alpha_2$-I | 9.1 | 10.9 |
| $\alpha_3$-I | 1.5 | 1.8 |
| $\beta_1$-I | 4.4 | 5.3 |
| $\beta_2$-I | 5.0 | 6.0 |
| $\gamma_1$-I | 3.6 | 4.3 |

TABLE IB-continued

| LL-E33288 Components | Retention Time (minutes) | Retention Volume (ml) |
|---|---|---|
| $\delta_1$-I | 2.6 | 3.1 |

The LL-E33288 components are separated and identified by the following TLC system:

Adsorbant: Silica gel 60 $F_{254}$ pre-coated aluminum sheets, 0.2 mm layer thickness, EM Reagents;

Detection: Visualized by quenching effect under short wavelength UV lamp (254 nm), and bioautography using *Bacillus subtilis* or the modified biochemical induction assay;

Solvent Systems:

I, ethyl acetate saturated with 0.1M aqueous potassium dihydrogen phosphate;

II, 3% isopropyl alcohol in ethyl acetate saturated with 0.1M aqueous potassium dihydrogen phosphate;

III, ethyl acetate:methanol (95.5).

Table II gives the approximate $R_f$ values of LL-E33288 components in these three systems:

TABLE II

| LL-E33288 Components | $R_f$ Value | | |
|---|---|---|---|
| | Solvent System I | Solvent System II | Solvent System III |
| $\alpha_1$-Br, $\alpha_1$-I | 0.67 | 0.80 | 0.79 |
| $\alpha_2$-Br, $\alpha_2$-I | 0.61 | 0.75 | 0.73 |
| $\alpha_3$-Br, $\alpha_3$-I | 0.55 | 0.69 | 0.61 |
| $\alpha_4$-Br | 0.49 | 0.64 | 0.54 |
| $\beta_2$-Br, $\beta_2$-I | 0.32 | 0.41 | 0.45 |
| $\beta_1$-Br, $\beta_1$-I | 0.24 | 0.35 | 0.36 |
| $\gamma_1$-Br, $\gamma_1$-I | 0.18 | 0.28 | 0.27 |
| $\delta_1$-I | 0.11 | 0.19 | |

The new antibacterial and anti-tumor agents designated LL-E33288$\alpha_1$-Br, LL-E33288$\alpha_2$-Br, LL-E33288$\alpha_3$-Br, LL-E33288$\alpha_4$-Br, LL-E33288$\beta_1$-Br, LL-E33288$\beta_2$-Br, LL-E33288$\gamma_1$-Br, LL-E33288$\alpha_1$-I, LL-E33288$\alpha_2$-I, LL-E33288$\alpha_3$-I, LL-E33288$\beta_1$-I, LL-E33288$\beta_2$-I, LL-E33288$\gamma_1$-I and LL-E33288$\delta_1$-I are formed during the cultivation under controlled conditions of a new strain of *Micromonosoora echinospora* ssp. *calichensis*. This microorganism is maintained in the culture collection of the Medical Research Division, American Cyanamid Company, Pearl River, New York as culture number LL-E33288. A viable culture of this new microorganism has been deposited with the Culture Collection Laboratory, Northern Regional Research Center, U.S. Department of Agriculture, Peoria, Ill., on Aug. 9, 1984, and has been added to its permanent collection. It has been assigned by such depository the strain designation NRRL-15839. Access to such culture, under strain designation NRRL-15839, during pendency of the instant application shall be available to one determined by the Commissioner of Patents and Trademarks to be entitled thereto under 37 C.F.R. §1.14 and 35 U.S.C. §122, and all restrictions on availability to the public of such culture will be irrevocably removed upon grant of a patent on the instant application.

Culture LL-E33288 was isolated from a caliche clay soil sample collected in Texas.

The generic assignment of the strain NRRL-15839 to the genus-Micromonospora was confirmed morphologically and chemically. The strain produces monospores either singly or in masses on the vegetative hyphae. No aerial hyphae were observed. Electron microscopic examination showed that the spores were warty. Whole cell analysis showed that the strain contained the meso isomer of diaminopimelic acid (DAP). The 3-OH derivative of DAP was present in large (major) amounts. Additionally the strain showed the presence of xylose plus traces of arabinose in its whole cell sugar hydrolysates (whole cell sugar pattern of Type D).

From macromorphological and physiological studies it was concluded that NRRL-15839 can be considered subspecies of *M. echinospora* (it is closest to *M. echinospora* ssp. *pallida*). Data on the morphology of NRRL-15839 are given in Tables A and B. Physiological data are given in Tables C and D.

TABLE A

| Macromorphology Of NRRL-15839 (Colors Are NBS-ISCC) | | | |
|---|---|---|---|
| ISP Agar Medium | Spores | Vegetative Mycelium | Soluble Pigments |
| Yeast-Malt (ISP 2) | — | Dark orange-yellow (72) | — |
| Oatmeal (ISP 3) | — | Colorless → pale orange-yellow (73) | — |
| Inorganic Salts-Starch (ISP 4) | Slight border of black spores | Dark orange-yellow (72) to lt. yellow-brown (76) | Lt. brownish |
| Glycerol-Asparagine (ISP 5) | — | Pale orange-yellow (73) → colorless | — |

TABLE B

| Macromorphology of NRRL-15839 on Various Agar Media Used for Actinomycete Growth (28° C., 2 weeks) | |
|---|---|
| Agar Medium | NRRL-15839 |
| Pablum | Beige vegetative hyphae Slight black spores No soluble pigment |
| Yeast Czapeks | Beige vegetative hyphae No spores No soluble pigment |
| Czapek's | Beige vegetative hyphae Slight black spores No soluble pigment |
| Yeast Dextrose | Tan vegetative hyphae Moderate black sp. Slight dark pigment |
| Nutrient | Colorless to tan vegetative hyphae Slight black spores No soluble pigment |
| Nutrient-Glycerol | Colorless to light beige vegetative hyphae No black spores No soluble pigment |
| Bennett's Dextrin | Colorless to beige vegetative hyphae Slight black spores Slight rosy-brown pigment |
| Glucose-Asparagine | Colorless to light orange-beige vegetative hyphae No spores No soluble pigment |

TABLE C

| Carbohydrate Utilization of NRRL-15839 | |
|---|---|
| Arabinose | + |
| Cellulose | — |
| Fructose | + |
| Glucose | + |
| Inositol | — |
| Mannitol | — |
| Raffinose | ± |
| Rhamnose | + |

TABLE C-continued

| Carbohydrate Utilization of NRRL-15839 | |
|---|---|
| Sucrose | + |
| Xylose | + |

TABLE D

| Physiological Reactions of NRRL-15839 | |
|---|---|
| Hydrolysis of | |
| Casein | + |
| Xanthine | − |
| Hypoxanthine | − |
| Tyrosine | + |
| Adenine | − |
| Gelatin | + |
| Potato Starch | + |
| Esculin | + |
| Production of | |
| Nitrate Reductase | + |
| Phospatase | W |
| Urease | − |
| Growth on | |
| Salicin | − |
| 5% NaCl | − |
| Lysozyme Broth | − |
| Decarboxylation of | |
| Acetate | + |
| Benzoate | − |
| Citrate | − |
| Lactate | − |
| Malate | − |
| Mucate | − |
| Oxalate | − |
| Propionate | + |
| Pyruvate | + |
| Succinate | − |
| Tartrate | − |
| Acid from | |
| Adonitol | − |
| Arabinose | + |
| Cellobiose | + |
| Dextrin | + |
| Dulcitol | − |
| Erythritol | − |
| Fructose | + |
| Galactose | V |
| Glucose | + |
| Glycerol | − |
| Inositol | − |
| Lactose | − |
| Maltose | + |
| Mannitol | − |
| Mannose | + |
| α-Methyl D Glucoside | − |
| Melibiose | − |
| Raffinose | + |
| Rhamnose | + |
| Salicin | + |
| Sorbitol | − |
| Sucrose | + |
| Trehalose | + |
| Xylose | + |
| β-Methyl D-xyloside | − |
| Growth at | |
| 10° | − |
| 42° | + |
| 45° | + |

+ = positive;
− = negative;
V = variable;
W = weak.

Derivation of Mutant LL-E33288-R66, NRRL-15975

In an effort to improve fermentation yields, the original culture LL-E33288 (NRRL-15839) was plated and 50 single colonies were isolated. These were designated NS1 to NS50 (NS=natural selection).

Fermentation of these isolates showed that those with moderate sporulation were generally better producers of LL-E33288 complex. Selected as representative of this group was isolate NS6.

Using isolate NS6 as the starting culture, spore suspensions were prepared and exposed to various mutagens. Single colonies were isolated from a nitrosoguanidine treatment, but none proved to be significantly improved producers of the LL-E33288 complex. From a subsequent series of exposures to ultraviolet irradiation, single colonies were obtained from which isolate UV 610 was selected as a high yielding mutant. Isolate UV 610 was then streaked and sub-isolates 1 to 7 were obtained. Sub-isolate UV 610(3) was selected for further work.

Because of the highly potent antibacterial and antineoplastic nature of the LL-E33288 complex, it is possible that once a limited concentration of the antibiotic is biosynthesized in the fermentation it may become toxic/inhibitory to the producing culture. Thus, an effort was made to obtain isolates which are resistant to the LL-E33288 antibiotic complex.

Vegetative growth from isolate UV 610(3) was prepared as employed for fermentation and used to inoculate a flask of medium consisting of peptone, dextrose, molasses and water. The medium was supplemented with LL-E33288$\beta_1$-Br at a concentration of 8 μg/ml. A number of platings were done from this flask and a resistant population was obtained on the seventh day. A total of 97 colonies (R1 to R97) were isolated. Isolate R66 was selected as a potentially improved producer of LL-E33288$\beta_1$-Br.

This history is represented schematically below.

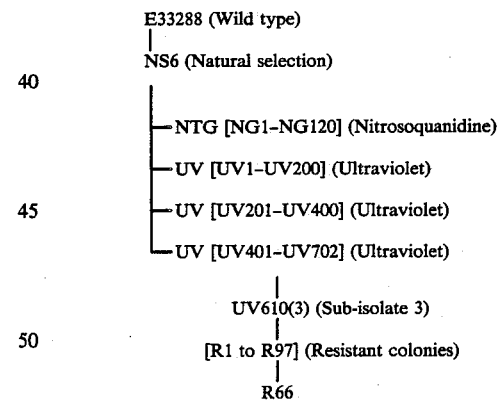

The mutant R66 is maintained in the culture collection of the Medical Research Division, American Cyanamid Company, Pearl River, N.Y. as culture number LL-E33288 R66. A viable culture of this new microorganism has been deposited with the Culture Collection Laboratory, Northern Regional Research Center, U.S. Department of Agriculture, Peoria, Ill. on June 6, 1985, and has been added to its permanent collection. It has been assigned by such depository the strain designation NRRL-15975. Access to such culture, under strain designation NRRL-15975, during pendency of the instant application shall be available to one determined by the Commissioner of Patents and Trademarks to be entitled thereto under C.F.R. §4 and 35 U.S.C. §122, and all restrictions on availability to the public of such culture will be irrevocably removed upon grant of a patent on the instant application.

Morphologically, NRRL-15975 forms fewer spores than NRRL-15839. A comparison of NRRL-15975 with NRRL-15839 is given in Table DD.

Chemically, both NRRL-15839 and NRRL-15975 show the same whole cell sugar patterns (Type D: xylose and traces of arabinose). The whole cell diaminopimelic acid analysis reveals that 15975 does not form the meso isomer but only the 3-hydroxy derivative (NRRL-15839 contains both compounds). This does not change the chemo-taxonomic assignment.

Physiological tests show that NRRL-15839 and NRRL-15975 differ in only two physiological reaction (See Table DD). NRRL-15975 is negative for nitrate reductase and positive for utilization of lactate NRRL-15839 was weakly positive for both, but is now negative after having been maintained on slants for a few months. Thus these characters should be considered variable for this taxon.

TABLE DD

Morphological Comparison of NRRL-15839 and NRRL-15975

| Agar Medium | | NRRL-15839 | NRRL-15975 |
| --- | --- | --- | --- |
| Bennett's- | V | Beige-tan | Beige tan |
| Dextrin | Sp | Black, copious | None |
| | SS | None | None |
| Czapek's | V | Orange tan, flat | Orange tan |
| | Sp | Black, traces | None |
| | SS | None | None |
| Yeast Extract- | V | Orange tan, flat | Orange tan, convoluted |
| Czapek's | | | |
| | Sp | Black, traces | None |
| | SS | None | Slight yellowish |
| Potato- | V | Very poor growth | Very poor growth |
| Dextrose | Sp | None | None |
| | SS | None | None |
| Nutrient | V | Tan | Tan |
| glycerol | Sp | Black, sparse | Black, sparse |
| | SS | None | Slight brownish |
| Nutrient | V | Tan | Tan |
| | Sp | Black, fair | None |
| | SS | None | None |

V = vegetative hyphae
Sp = spores
SS = soluble pigment

It has now been discovered that all of the aforementioned LL-E33288 components produced by NRRL-15839 and 15975 are also produced by a newly derived mutant named LL-E33288-UV 784, in much higher yields.

Derivation of Mutant LL-E33288-UV 784

Vegetative growth from isolate UV 610(3) (see following diagram) was prepared as employed for fermentation and used to inoculate a flask of medium consisting of peptone, dextrose, molasses and water. The medium was supplemented with LL-E33288$\beta_1$-Br at a concentration of about 8 μg/ml. A number of platings were done from this flask and a resistant population was obtained on the seventh day. A total of 97 colonies (R1 to R97) were isolated. Isolate R66 became NRRL-15975. Isolate R80 is essentially similar to R66 in its biosynthetic potential.

Isolate R80 was then used as the starting culture from which a spore suspension was prepared and exposed to relatively high concentrations of the LL-E33288 complex, the purpose being to obtain isolates resistant to the LL-E33288 antibiotics and thereby improve production yields.

One survivor, labeled $T_2$ did produce greater yields of LL-E33288$\beta_1$-Br and LL-E33288$\gamma_1$-I in flask fermentations. A spore suspension of $T_2$ was prepared and exposed to UV-irradiation. A total of 131 colonies were then isolated (UV 703 to UV 834), fermented and assayed. From this group, isolate UV 784 was selected for its activity in flask fermentations. Isolate UV 784, when fermented in the iodine containing medium, produced approximately double the yield of R66 (NRRL-15975).

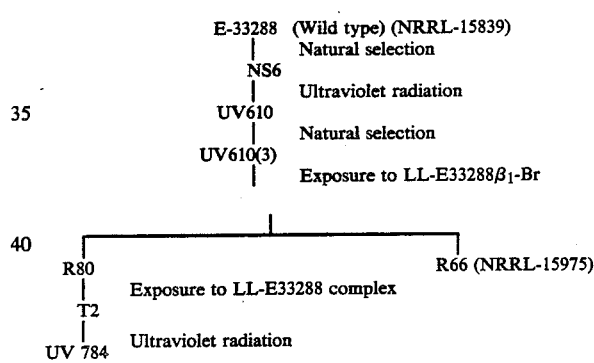

Diagram of UV 784 Derivation

The mutant LL-E33288 UV 784 is maintained by that number in the culture collection of the Medical Research Division, American Cyanamid Company, Pearl River, New York. A viable culture of this microorganism has been deposited with the Culture Collection Laboratory, Northern Regional Research Center, U.S. Department of Agriculture, Peoria, Ill. on Dec. 3, 1986, and has been added to its permanent collection. Access to said culture, under strain designation NRRL-18149, during pendency of the instant application shall be available to one determined by the Commissioner of Patents and Trademarks to be entitled thereto under C.F.R. §1.14 and 35 U.S.C. §122, and all restrictions on availability to the public of such culture will be irrevocably removed upon grant of a U.S. Patent on the instant application.

Proposed structures of some of the LL-E33288 antibiotics are disclosed below.

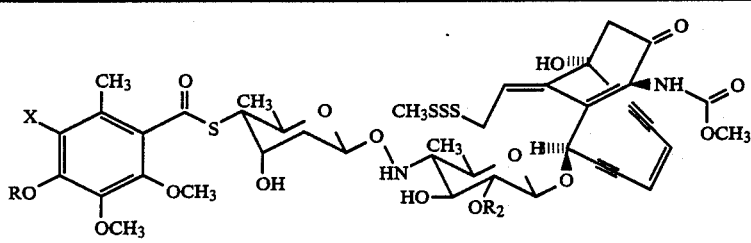

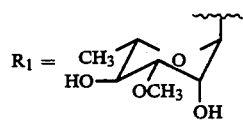 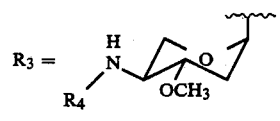

| E33288 | X | R | R₂ | R₄ |
|---|---|---|---|---|
| $\alpha_2^I$ | I | H | $R_3$ | $C_2H_5$ |
| $\alpha_3^I$ | I | $R_1$ | H | |
| $\beta_1^I$ | I | $R_1$ | $R_3$ | $(CH_3)_2CH$ |
| $\gamma_1^I$ | I | $R_1$ | $R_3$ | $C_2H_5$ |
| $\delta_1^I$ | I | $R_1$ | $R_3$ | $CH_3$ |
| $\beta_1^{Br}$ | Br | $R_1$ | $R_3$ | $(CH_3)_2CH$ |
| $\gamma_1^{Br}$ | Br | $R_1$ | $R_3$ | $C_2H_5$ |
| $\alpha_2^{Br}$ | Br | H | $R_3$ | $C_2H_5$ |
| $\alpha_3^{Br}$ | Br | $R_1$ | H | |

It is to be understood that for the production of these new antibacterial and anti-tumor agents the present invention is not limited to this particular organisms or to organisms fully answering the above growth microscopic characteristics which were given for illustrative purposes only. In fact, it is desired and intended to include the use of mutants produced from these organisms by various means such as exposure to X-radiation, ultraviolet radiation, N'-methyl-N'-nitro-N-nitrosoguanidine, actinophages and the like.

The in vitro antibacterial activity of LL-E33288 components was determined against a spectrum of gram-positive and gram-negative bacteria by a standard agar dilution method. Mueller-Hinton agar containing two-fold decreasing concentrations of the antibiotics was poured into petri plates. The agar surfaces were inoculated with 1 to 5×10⁴ colony forming units of bacteria by means of a Steers replicating device. The lowest concentration of LL-E33288 component that inhibited growth of a bacterial strain after about 18 hours of incubation at approximately 35° C. was recorded as the minimal inhibitory concentration (MIC) for that strain. The results are summarized in Table III.

TABLE III

In vitro Antibacterial Activity of LL-E33288 Components

| Organism | | Minimal Inhibitory Concentration, mcg/ml | | | |
|---|---|---|---|---|---|
| | | Beta₁-Br | Beta₁-I | Gamma₁-Br | Gamma₁-I |
| Escherichia coli | CMC 84-11 | 0.25 | 0.50 | 0.50 | 0.25 |
| Escherichia coli | No. 311-(MP) | 0.12 | 0.25 | 0.25 | 0.25 |
| Escherichia coli | ATCC 25922 | 0.12 | 0.25 | 0.25 | 0.25 |
| Klebsiella pneumoniae | CMC 84-5 | 0.25 | 0.50 | 0.50 | 0.25 |
| Klebsiella pneumoniae | AD (MP) | 0.12 | 0.50 | 0.50 | 0.25 |
| Enterobacter cloacae | CMC 84-4 | 0.50 | 0.50 | 0.50 | 0.50 |
| Enterobacter aerogenes | IO 83-44 | 0.25 | 0.25 | 0.50 | 0.50 |
| Serratia marcescens | CMC 83-27 | 0.12 | 0.25 | 0.50 | 0.25 |
| Serratia marcescens | F35 (MP) | 0.12 | 0.50 | 0.25 | 0.12 |
| Morganella morganii | 10 83-18 | 0.50 | 1.00 | 0.50 | 0.25 |
| Providencia stuartii | CMC 83-82 | 0.25 | 0.50 | 1.00 | 0.25 |
| Citrobacter diversus | K 82-84 | 0.12 | 0.50 | 0.50 | 0.25 |
| Citrobacter freundii | IO 83-13 | 0.12 | 0.25 | 0.25 | 0.12 |
| Acinetobacter sp. | CMC 83-89 | 0.06 | 0.25 | 0.25 | 0.12 |
| Acinetobacter sp. | IO 83-49 | 0.12 | 0.25 | 0.25 | 0.06 |
| Pseudomonas aeruginosa | 12-4-4 (MP) | 0.5 | 0.50 | 1.00 | 0.25 |
| Pseudomonas aeruginosa | ATCC 27853 | 0.25 | 0.25 | 0.50 | 0.12 |
| Staphylococcus aureus | Smith | ≦0.0025 | ≦0.000031 | ≦0.000031 | ≦0.000031 |
| Staphylococcus aureus | SSC 82-31 | ≦0.00025 | ≦0.000031 | ≦0.000031 | ≦0.000031 |
| Staphylococcus aureus | ATCC 25923 | ≦0.00025 | ≦0.000031 | ≦0.000031 | ≦0.000031 |
| Staphylococcus aureus | SSC 82-20 | ≦0.00025 | ≦0.000031 | ≦0.000031 | ≦0.000031 |
| Staphylococcus aureus | SSC 82-26 | ≦0.00025 | ≦0.000031 | ≦0.000031 | ≦0.000031 |
| Staphylococcus aureus | SSC 82-24 | ≦0.00025 | ≦0.000031 | ≦0.000031 | ≦0.000031 |
| Staphylococcus aureus | SSC 82-57 | ≦0.00025 | ≦0.000031 | ≦0.000031 | ≦0.000031 |
| Staphylococcus epidermidis | CMC-83-133 | ≦0.00025 | ≦0.000031 | ≦0.000031 | ≦0.000031 |
| Staphylococcus epidermidis | ATCC 12228 | ≦0.00025 | ≦0.000031 | ≦0.000031 | ≦0.000031 |
| Enterococcus sp. | CMC 83-53 | 0.0038 | 0.031 | 0.062 | 0.0078 |
| Streptococcus faecalis | ATCC 29212 | ≦0.00025 | 0.00012 | ≦0.000031 | 0.00012 |
| Micrococcus luteus | PCI 1001 | ≦0.00025 | ≦0.000031 | ≦0.000031 | ≦0.000031 |

TABLE III-continued

| In vitro Antibacterial Activity of LL-E33288 Components | | | | | |
|---|---|---|---|---|---|
| | | Minimal Inhibitory Concentration, mcg/ml | | | |
| Organism | | $Beta_1$-Br | $Beta_1$-I | $Gamma_1$-Br | $Gamma_1$-I |
| Bacillus subtilis | ATCC | ≦0.00025 | ≦0.000031 | ≦0.000031 | ≦0.000031 |

Certain in vivo testing systems and protocols have been developed by the National Cancer Institute for testing compounds to determine their suitability as antineoplastic agents. These have been reported in "Cancer Chemotherapy Reports", Part III, Vol. 3, No. 2 (1972), Geran, et al. These protocols have established standardized screening tests which are generally followed in the field of testing for anti-tumor agents. Of these systems, lymphocytic leukemia P388, melanotic melanoma B16, L1210 leukemia and colon 26 adenocarcinoma are particularly significant to the present invention. These neoplasms are utilized for testing as transplantable tumors in mice. Generally, significant anti-tumor activity, shown in these protocols by a percentage increase of mean survival times of the treated animals (T) over the control animals (C), is indicative of similar results in human leukemias and solid tumors.

Lymphocytic Leukemia P388 Test

The animals used were $BDF_1$ mice, all of one sex, weighing a minimum of 17 g and all within a 3 g weight range. There were 5 or 6 mice per test group. The tumor transplant was by intraperitoneal injection of 0.5 ml of dilute ascitic fluid containing $10^6$ cells of lymphocytic leukemia P388. LL-E33288 antibiotics were tested in the P388 system both as the individual $\beta_1$-Br and $\gamma_1$-Br components and as a complex of all components (Bromo-complex). The test compounds were administered intraperitoneally at a volume of 0.5 ml in 0.2% Klucel in normal saline on days 1, 5 and 9 (relative to tumor inoculation) at the indicated doses. The mice were weighed and the survivors recorded on a regular basis for 30 days. The median survival time and the ratio of survival time for treated (T)/control (C) animals were calculated. The positive control compound was Cisplatin given as an intraperitoneal injection in 0.5 ml of 0.2% Klucel on days 1, 5 and 9 at the indicated doses. The results appear in Table IV.

If T/C X 100 (%) is 125 or over, the tested compound is considered to have significant anti-tumor activity.

TABLE IV

| Lymphocytic Leukemia P388 Test | | | |
|---|---|---|---|
| Compound | Dose (mg/kb) | Median Survival (Days) | T/C × 100 (%) |
| LL-E33288 (Bromo-complex) | 3.2 | 16.5 | 156 |
| | 1.6 | 17.5 | 165 |
| | 0.8 | 18.5 | 175 |
| | 0.4 | 19.0 | 179 |
| | 0.2 | 16.5 | 156 |
| Control | — | 10.6 | — |
| Positive Control | 1.0 | 21.5 | 203 |
| | 0.25 | 15.0 | 142 |
| | 0.06 | 14.5 | 137 |
| LL-E33288$\beta_1$-Br | 0.4 | 13.0 | 105 |
| | 0.2 | 18.0 | 145 |
| | 0.1 | 19.0 | 153 |
| | 0.05 | 17.5 | 141 |
| | 0.025 | 18.0 | 145 |
| | 0.012 | 14.0 | 113 |
| Control | — | 12.4 | — |
| Positive Control | 1.0 | 25.5 | 206 |
| | 0.4 | 19.0 | 153 |

TABLE IV-continued

| Lymphocytic Leukemia P388 Test | | | |
|---|---|---|---|
| Compound | Dose (mg/kb) | Median Survival (Days) | T/C × 100 (%) |
| | 0.06 | 15.0 | 121 |
| LL-E33288$\beta_1$-Br | 0.2 | 14.0 | 113 |
| | 0.1 | 21.0 | 169 |
| | 0.05 | 19.5 | 157 |
| | 0.025 | 18.0 | 145 |
| | 0.012 | 14.5 | 117 |
| Control | — | 12.4 | — |
| Positive Control | 1.0 | 25.5 | 206 |
| | 0.4 | 19.0 | 153 |
| | 0.06 | 15.0 | 121 |

Melanotic Melanoma B16

The animals used were $BDF_1$ mice, all of the same sex, weighing a minimum of 17 g and all within a 3 g weight range. There are normally 6 animals per test group. A 1 g portion of melanotic melanoma $B_{16}$ tumor was homogenized in 10 ml of cold balanced salt solution and a 0.5 ml aliquot of the homogenate was implanted intraperitoneally into each of the test mice. LL-E33288 antibiotics were tested in the $B_{16}$ system both as the individual $\beta_1$-Br and $\gamma_1$-Br components and as a complex of all components (Bromo-complex). The test compounds were administered intraperitoneally on days 1 through 9 (relative to tumor inoculation) at various doses. The mice were weighed and survivors recorded on a regular basis for 60 days. The median survival time and the ratio of survival time for treated (T)/control (C) animals was calculated. The positive control compounds were Cisplatin or Adriamycin. The results of this test appear in Table V. If T/C X 100 (%) is 125 or over, the tested compound is considered to have significant anti-tumor activity.

TABLE V

| Malanotic Melanoma $B_{16}$ Test | | | |
|---|---|---|---|
| Compound | Dose (mg/kb) | Median Survival (Days) | T/C × 100 (%) |
| LL-E33288 (Bromo-complex) | 0.8 | 30.0 | 188 |
| | 0.4 | 29.5 | 184 |
| | 0.2 | 27.0 | 169 |
| | 0.1 | 24.0 | 150 |
| Control | — | 16.0 | — |
| Cisplatin | 0.4 | 25.0 | 156 |
| | 0.2 | 25.0 | 156 |
| | 0.1 | 23.0 | 144 |
| | 0.05 | 21.5 | 134 |
| LL-E33288$\beta_1$-Br | 0.05 | 32.0 | 168 |
| | 0.025 | 33.5 | 176 |
| | 0.0125 | 32.0 | 168 |
| Control | — | 19.0 | — |
| Adriamycin | 0.8 | >60 | >316 |
| | 0.4 | >60 | >316 |
| LL-E332887$\beta_1$-Br | 0.05 | 33.5 | 176 |
| | 0.025 | 30.0 | 159 |
| | 0.0125 | 37.0 | 195 |
| Control | — | 19.0 | — |
| Adriamycin | 0.8 | >60 | >316 |
| | 0.4 | >60 | >316 |

Lymphocytic Leukemia L1210 Test

The animals used were BDF$_1$ mice, all of one sex, weighing a minimum of 17 g and all within a 3 g weight range. There were 6 mice in each test group and 18 in control groups. The tumor transplant was by intraperitoneal injection of 0.5 ml of lymphocytic leukemia L1210 at a concentration of 10$^5$ cells per mouse. LL-E33288 antibiotics were tested in the L1210 system both as the individual $\beta_1$-Br component and as a complex of all components (Bromo-complex). The test compounds were administered on days 1, 5 and 9 or days 1 through 9 (relative to tumor inoculation) at various doses. The mice were weighed and survivors recorded on a regular basis for 30 days. The median survival time and the ratio of survival time for treated (T)/control (C) animals were calculated. The positive control compound was 1,4-dihydroxy-5,8-bis{[2-(2-hydroxyethylamino)ethyl]amino}anthraquinone dihydrochloride or Cisplatin given intraperitoneally at the indicated dose. The results appear in Table VI. If T/C × 100 (%) is 125 or over, the tested compound is considered to have significant anti-tumor activity.

TABLE VI

Lymphocytic Leukemia L1210 Test

| Compound | Dose (mg/kb) | Median Survival (Days) | T/C × 100 (%) |
|---|---|---|---|
| LL-E33288 | 1.5 | 29.0 | 174 |
| (Bromo-complex) | 0.8 | 28.5 | 171 |
| | 0.4 | 22.5 | 135 |
| | 0.2 | 22.5 | 135 |
| Control | — | 16.7 | — |
| Anthraquinone | 1.6 | 30.0 | 180 |
| | 0.8 | 30.0 | 180 |
| | 0.4 | 30.0 | 180 |
| LL-E33288$\beta_1$-Br | 0.2 | 11.3 | 136 |
| | 0.1 | 11.4 | 137 |
| | 0.05 | 11.0 | 133 |
| | 0.025 | 11.3 | 136 |
| Control | — | 8.3 | — |
| Cisplatin | 5.0 | 7.5 | 90 |
| | 2.5 | 12.0 | 145 |
| | 1.25 | 11.0 | 133 |

Colon 26 Adenocarcinoma Test

The animals used were CD$_2$F$_1$ female mice weighing a minimum of 17 g and all within a 3 g weight range. There were 5 or 6 mice per test group with three groups of 5 or 6 animals used as untreated controls for each test. The tumor implant was by intraperitoneal (or subcutaneous) injection of 0.5 ml of a 2% Colon 26 tumor brei in Eagle's MEM medium containing antibiotics. LL-E33288 antibiotics were tested in the Colon 26 system as a complex (Bromocomplex) of all components. The test compounds were administered intraperitoneally on days 1, 5 and 9 (relative to tumor implant doses). The mice were weighed and deaths recorded on a regular basis for 30 days. The median survival times for treated (T)/control (C) animals were calculated. The positive control compound was Cisplatin. The results appear in Table VII. If T/C × 100 (%) is 130 or over, the tested compound is considered to have significant anti-tumor activity.

TABLE VII

Colon 26 Adenocarcinoma Test

| Compound | Dose (mg/kb) | Median Survival (Days) | T/C × 100 (%) |
|---|---|---|---|
| LL-E33288 | 1.5 | 39.5 | 212 |
| (Bromo-complex) | 0.8 | 32.5 | 175 |
| | 0.4 | 34.0 | 183 |
| | 0.2 | 25.5 | 137 |
| Control | — | 18.6 | — |
| Positive Control | 1.0 | 29.0 | 156 |
| | 0.5 | 38.5 | 207 |
| | 0.25 | 37.5 | 202 |

M5076 Sarcoma

The M5076 reticular cell Sarcoma is propagated as subcutaneous implants in C57B2/6 female mice. In the assays for anti-tumor activity, BDF$_1$ mice of either sex were inoculated intraperitoneally with 0.5 ml of a 10% tumor brei. LL-E33288 antibiotics were tested in the M5076 system as a complex (Bromo-complex) of all components. Test compounds were administered intraperitoneally on days 1, 5, 9, 13 and 17 relative to tumor inoculation on day zero. The median survival time in days were determined for each drug dose used on day 60 and the ratio of survival time for treated (T)/control (C) animals were calculated.

The results of this test appear in Table VIII compared to the results obtained with Cisplatin. If T/C × 100 (%) is 125 or over, the tested compound is considered to have significant anti-tumor activity.

TABLE VIII

M5076 Sarcoma

| Compound | Dose (mg/kb) | Median Survival (Days) | T/C × 100 (%) |
|---|---|---|---|
| LL-E33288 | 1.5 | 50.0 | 175 |
| (Bromo-complex) | 0.8 | 50.0 | 175 |
| | 0.4 | 39.5 | 139 |
| Control | — | 28.5 | — |
| Cisplatin | 1.0 | 30.0 | 105 |
| | 0.5 | 44.5 | 156 |
| | 0.25 | 45.0 | 158 |

In the same manner, the following iodo-components were tested for antineoplastic activity.

TABLE IX

Colon 26 Adenocarcinoma Test

| Compound | Dose (mg/kb) | Median Survival (Days) | T/C × 100 (%) |
|---|---|---|---|
| LL-E33288$\gamma_1$-I | 0.005 | >25.5 | >196 |
| (Test 1) | 0.0025 | 22.0 | 169 |
| | 0.00125 | 18.5 | 142 |
| | 0.0006 | 18.0 | 138 |
| | 0.0003 | 15.5 | 119 |
| | 0.00015 | 15.0 | 115 |
| Control | — | 13.0 | — |
| Positive Control Novantrone ®* | 1.6 | 22.5 | 173 |
| LL-E33288$\gamma_1$-I | 0.01 | 11.0 | 100 |
| (Test 2) | 0.005 | 18.0 | 164 |
| | 0.0025 | 22.5 | 205 |
| | 0.00125 | 18.5 | 168 |
| | 0.0006 | 16.0 | 145 |
| | 0.0003 | 14.0 | 127 |
| | 0.00015 | 14.0 | 127 |
| Control | — | 11.0 | 1 |
| Positive Control | 1.6 | 19.0 | 173 |

TABLE IX-continued

Colon 26 Adenocarcinoma Test

| Compound | Dose (mg/kb) | Median Survival (Days) | T/C × 100 (%) |
|---|---|---|---|
| Novantrone ®* | 0.8 | 16.0 | 145 |

*1,4-dihydroxy-5,8-bis{[2-(2-hydroxyethylamino)ethyl]-amino}anthraquinone-2HCl

TABLE X

Melanotic Melanoma $B_{16}$ Test

| Compound | Dose (mg/kb) | Median Survival (Days) | T/C × 100 (%) |
|---|---|---|---|
| LL-E33288$\gamma_1$-I | 0.0025 | 26.5 | 156 |
|  | 0.00125 | 27.0 | 159 |
|  | 0.0006 | 42.5 | 250 |
|  | 0.0003 | 35.5 | 209 |
|  | 0.00015 | 33.5 | 197 |
|  | 0.00007 | 30.5 | 179 |
| Control | — | 17.0 | — |
| Adriamycin | 0.8 | 48.0 | 282 |
|  | 0.4 | 40.0 | 235 |
|  | 0.2 | 34.5 | 203 |

TABLE XI

Lymphocytic Leukemia L1210 Test

| Compound | Dose (mg/kb) | Median Survival (Days) | T/C × 100 (%) |
|---|---|---|---|
| LL-E33288$\gamma_1$-I | 0.01 | 8.0 | 89 |
|  | 0.005 | 14.0 | 156 |
|  | 0.0025 | 11.0 | 122 |
|  | 0.0012 | 10.5 | 117 |
|  | 0.0006 | 10.0 | 111 |
| Control | — | 9 | — |
| Positive Control | 3.2 | 15.0 | 167 |
| Novatrone ® | 1.6 | 11.5 | 128 |
|  | 0.8 | 12.0 | 133 |
|  | 0.4 | 11.0 | 122 |

TABLE XII

Colon 26 Adenocarcinoma Test

| Compound | Dose (mg/kb) | Median Survival (Days) | T/C × 100 (%) |
|---|---|---|---|
| LL-E33288$\gamma_1$-I | 0.01 | 11.0 | 59 |
|  | 0.005 | 25.5 | 138 |
|  | 0.0025 | 27.0 | 146 |
|  | 0.00125 | 22.5 | 122 |
|  | 0.0006 | 23.5 | 127 |
|  | 0.0003 | 20.0 | 108 |
|  | 0.00015 | 17.5 | 95 |
|  | 0.00007 | 17.0 | 92 |
| Control | — | 18.5 | — |
| Positive Control | 2.0 | 15.5 | 84 |
| Cisplatin | 1.0 | 27.5 | 149 |
|  | 0.5 | 23.5 | 127 |

General Fermentation Conditions

Cultivation of *Micromonospora echinospora* NRRL-15839 or NRRL-15975 may be carried out in a wide variety of liquid culture media. Media which are useful for the production of these novel antibacterial and antitumor agents include an assimilable source of carbon, such as starch, sugar, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. and sources of either bromine (sodium bromide) or iodine (potassium iodide). Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone may be added as needed.

General Procedure for the Isolation and Separation of the Antibiotics - LL-E33288

The LL-E33288 antibiotics are recovered from the fermentation broth by extracting the whole mash with an organic solvent such as ethyl acetate or dichloromethane. The antibiotic complex, contained in the organic extract, is further purified by selective precipitation from lower hydrocarbons. The crude LL-E33288 antibiotic complex thus obtained is further purified and separated into the individual components by a series of column chromatographies using silica gel, Sephadex ® LH-20 (Pharmacia Fine Chemicals) and $C_{18}$ bonded silica.

The invention will be described in greater detail in conjunction with the following non-limiting specific examples.

EXAMPLE 1

Inoculum Preparation

A typical medium used to grow the primary inoculum was prepared according to the following formula:

| Beef extract | about 0.3% |
|---|---|
| Tryptone | about 0.5% |
| Dextrose | about 0.5% |
| Dextrin | about 2.4% |
| Calcium carbonate | about 0.4% |
| Yeast extract | about 0.5% |
| Water qs to | 100% |

This medium was adjusted to pH 7.0 and then sterilized. A 100 ml portion of this sterile medium, in a flask, was inoculated with frozen mycelia of the culture NRRL-15839. The inoculated medium was placed on a rotary shaker and agitated vigorously for 48 hours at 32° C. This incubated medium was then used to inoculate 10 liters of the above sterile medium in a 14 liter fermentor. This medium was incubated, with agitation, at 32° C. for 48 hours, providing secondary inoculum. This secondary inoculum was then used to inoculate 300 liters of the above sterile medium in a tank and incubated for 48 hours at 30° C. while agitated by an impeller driven at 180–200 rpm, providing the tertiary or seed inoculum.

EXAMPLE 2

Tank Fermentation

A fermentation medium was prepared according to the following formulation:

| Dextrose | about 0.5% |
|---|---|
| Sucrose | about 1.5% |
| Peptone, bacteriological grade | about 0.2% |
| Dibasic potassium phosphate | about 0.01% |
| Molasses | about 0.5% |
| Calcium carbonate | about 0.5% |
| Source of bromine* | trace amounts |

-continued

| Water qs to | 100% |

*If the E-33288 Iodo complex were to be produced, trace amounts of an iodine source should be used.

A 2800 liter portion of the above medium was sterilized and then inoculated with 300 liters of tertiary (seed) inoculum prepared as described in Example 1. Aeration was supplied at the rate of 0.53 liters of sterile air per liter of mash per minute and agitation was supplied by an impeller driven at 110 rpm. The temperature was maintained at about 28° C. and the fermentation was terminated after about 97 hours, at which time the mash was harvested.

The fermentation was monitored for production of the LL-E33288 antibiotics by antibacterial activity, biochemical induction assay, TLC and HPLC analyses The whole harvest mash was adjusted to pH 6 and then extracted with ½ mash volume ethyl acetate. The ethyl acetate extract was concentrated to a syrup which was washed twice with hexane and filtered through diatomaceous earth. The diatomaceous earth cake was thoroughly mixed with ethyl acetate and filtered. The filtrate was concentrated to 3 liters, dried over excess anhydrous sodium sulfate and then precipitated by the addition of hexane giving about 26.7 g of crude LL-E33288 complex.

EXAMPLE 3

Separation of LL-E33288$\alpha_1$-Br, $\alpha_2$-Br, $\alpha_3$-Br and $\alpha_4$-Br from LL-E33288$\beta_1$-Br, $\beta_2$-Br and $\gamma_1$-Br Approximately 26.7 g of crude LL-E33288 complex (Bromo-complex) from Example 2 was divided evenly into three portions and chromatographed on three separate 2.4×110 cm silica gel columns (Silica Woelm ®, 32–63 m, Woelm Pharma) packed and equilibrated with ethyl acetate saturated with 0.1 M aqueous potassium dihydrogen phosphate. The columns were first eluted with the same solvent at a flow rate of 3 ml/minute for 18 hours, collecting 18 ml fractions. The eluent was changed to ethyl acetate:methanol (95:5) and elution continued for 8 hours. Finally the columns were eluted with ethyl acetate:methanol (90:10) for 10 hours. The fractions were assayed by the modified biochemical induction assay (BIA). The positive fractions were analyzed by TLC using silica gel 60 pre-coated sheets and developed with the solvent system 3% isopropanol in ethyl acetate saturated with 0.1 M aqueous potassium dihydrogen phosphate and detected by bioautography using the modified BIA.

Fractions containing LL-E33288$\alpha_1$-Br, $\alpha_2$-Br, $\alpha_3$-Br and $\alpha_4$-Br (LL-E33288$\alpha$-Br complex) from the three columns were pooled, concentrated to dryness and the residue was dissolved in ethyl acetate and washed with a small amount of water. The ethyl acetate solution was dried over anhydrous sodium sulfate and precipitated as before to yield about 4.2 g of crude LLE-33288$\alpha$-Br complex.

Fractions containing LL-E33288$\beta_2$-Br, $\beta_1$-Br and $\gamma_1$-Br (LL-E33288$\beta$-Br complex containing $\gamma_1$-Br from the three columns were pooled and worked up as above to yield about 2.0 g of crude LL-E33288$\beta$-Br complex containing $\gamma_1$-Br.

EXAMPLE 4

Isolation of LL-E33288$\beta_1$-Br and LL-E33288$\gamma_1$-Br

An approximately 1.9 g sample of the LL-E33288$\beta$-Br complex containing $\gamma_1$-Br from Example 3 was chromatographed on a 25×10 cm Sephadex ® LH-20 column equilibrated with methanol:water (90:10 at a flow rate of 1.2 ml/minute, collecting 15 ml fractions. The fractions were assayed in the BIA and those active were analyzed by TLC as before. Fractions 21–26 containing most of the LL-E33288$\beta_1$-Br, $\beta_2$-Br and $\gamma_1$-Br, were pooled and concentrated to remove methanol and the resulting aqueous mixture was lyophilized to yield about 435 mg of partially purified complex containing approximately 10% of LL-E33288$\beta_1$-Br, 1% of LL-E33288$\beta_2$-Br and 4% of LL-E33288$\gamma_1$-Br.

The above partially purified LL-E33288$\beta$-Br complex containing $\gamma_1$-Br was divided evenly and chromatographed on two 1.5×100 cm silica gel columns (Kiesel Gel 60, 40–63 $\mu$m, EM Products for chromatography) packed and equilibrated with ethyl acetate:methanol (98.2) at a flow rate of 1 ml/minute, collecting 12 ml fractions. The fractions were assayed and analyzed by TLC as before and those containing primarily LL-E33288$\beta_1$-Br were pooled, concentrated and precipitated from hexane to yield about 26 mg of 80% pure LL-E33288$\beta_1$-Br. Those fractions containing LL-E33288$\gamma_1$-Br (chromatographing just after LL-E33288$\beta_1$-Br) were pooled and worked up to yield about 4.5 mg of 30% pure LL-E33288$\gamma_1$-Br. A few fractions containing LL-E33288$\beta_2$-Br (chromatographing just before LL-E33288$\beta_1$-Br), were pooled and worked up to yield a trace amount of LL-E33288$\beta_2$-Br.

EXAMPLE 5

Final Purification of LL-E33288$\beta_1$-Br

Approximately 26 mg of 80% pure LL-E33288$\beta_1$-Br from Example 4 was combined with other LL-E33288$\beta_1$-Br samples of similar purity derived from other fermentations conducted under identical conditions. A total of about 38 mg of this combined $\beta_1$-Br was further purified by reverse phase preparative TLC using Whatman PLKC$_{18}$F, 100 m pre-coated TLC plates, developed with methanol 0.1 M ammonium acetate buffer at pH 4.0 (90:10). The band containing LL-E33288$\beta_1$-Br, chromatographing at R$_f$=0.66 and visualized by quenching effect under short wavelength UV lamp (254 nm), was excised and the antibiotic was washed off the adsorbant with 10% isopropyl alcohol in ethyl acetate saturated with 0.1 M aqueous potassium dihydrogen phosphate. The solution was concentrated and the residue was dissolved in ethyl acetate and washed with a small amount of water. The organic solution containing LL-E33288$\beta_1$-Br was worked up as before to yield about 24.5 mg of 90% pure LL-E33288$\beta_1$-Br. This sample was further purified by preparative TLC on silica gel (Silica) Gel GF pre-coated plates, 1000 m, Analtech) developed with 3% isopropyl alcohol in ethyl acetate saturated with 0.1 M aqueous potassium dihydrogen phosphate. The major quenching band under short wavelength UV lamp (254 nm), chromatographing at R$_f$=0.7, was excised and the antibiotic was washed off the adsorbant with dichloromethane:methanol (80:20). The organic solution containing LL-E33288$\beta_1$-Br was worked up as before to yield about 18.8 mg of substantially pure LL-E33288$\beta_1$-Br.

EXAMPLE 6

Final Purification of LL-E33288$\beta_1$-Br

Approximately 4.5 mg of 30% pure LL-E33288$\gamma_1$-Br from Example 4 was combined with other LL-E33288$\gamma_1$-Br samples of similar purity derived from other fermentations conducted under identical conditions. A total of 18 mg of this combined sample was further purified by preparative TLC on silica gel (Silica Gel GF pre-coated tapered plates, Analtech) developed with 2% isopropyl alcohol in ethyl acetate saturated with 0.1M aqueous potassium dihydrogen phosphate. The major quenching band under short wavelength UV lamp 9254 nm), chromatographing at $R_f$=0.5, was excised and worked up as before to yield about 4.3 mg of substantially pure LL-E33288$\gamma_1$-Br.

A preferred fermentation medium for production of LL-E33288 Bromo-complex is as follows:

| Ingredient | Percent |
| --- | --- |
| Sucrose | 2.0 |
| Ferrous Sulfate Heptahydrate | 0.01 |
| Magnesium Sulfate Heptahydrate | 0.02 |
| Calcium Carbonate | 0.5 |
| Peptone | 0.2 |
| Molasses | 0.5 |
| Sodium Bromide | 0.05 |
| Water qa to | 100 |

However, the addition of iodine as potassium iodide, to the fermentation medium provided substantial improvements by:

(1) markedly enhancing vegetative growth in the fermentation;
(2) increasing zones of inhibition in bioassays versus *Escherichia coli* #300 and *Bacillus subtilis* #308;
(3) providing substantial activity at the $R_f$ of LL-E33288$\beta_1$-I and $\gamma_1$-I on the bioautography of TLC plates; and
(4) enhancement of other components as detected by TLC.

The following two media are preferred for the production of LL-E33288 Iodo-complex:

| Ingredient | Percent Media A | Media B |
| --- | --- | --- |
| Sucrose | 2.0 | 2.0 |
| Ferrous Sulfate Heptahydrate | 0.01 | 0.01 |
| Magnesium Sulfate Heptahydrate | 0.02 | 0.02 |
| Calcium Carbonate* | 0.5 | 0.25 |
| Peptone** | 0.2 | 0.2 |
| Molasses | 0.5 | 0.5 |
| Potassium iodide | 0.05 | 0.01 |
| Water qs to | 100 | 100 |

*Mississippi lime.
**Best results were obtained with MARCOR ® bacteriological peptone, but other peptones are usable, including also polypeptides from meat and casein hydrolysates.

EXAMPLE 7

A mycelial-spore suspension was prepared by scraping the surface of a slant of culture NRRL-15839 to which 5 ml of sterile distilled water had been added. This suspension was then used to inoculate 100 ml of sterile seed medium of the following formula:

| | |
| --- | --- |
| Yeast Extract | 0.5% |
| Beef Extract | 0.3% |
| Tryptose | 0.5% |
| Starch | 2.4% |
| Dextrose | 0.5% |
| Calcium Carbonate | 0.4% |
| Water qs to | 100.0% | in a 500 ml flask. This seed flask was incubated at 28° C. on a rotary shaker at 200 rpm for 3–4 days, producing Stage I inoculum.

The Stage I inoculum was used to inoculate a Stage II inoculum of the same sterile medium, which was incubated under the same conditions for 2 days.

The Stage II inoculum was then used to inoculate 100 ml of sterile fermentation medium of the formula:

| | |
| --- | --- |
| Sucrose | 2.0% |
| Ferrous Sulfate Heptahydrate | 0.01% |
| Magnesium Sulfate Heptahydrate | 0.02% |
| Calcium Carbonate | 0.5% |
| Peptone (MARCOR ®) | 0.2% |
| Molasses | 0.5% |
| Potassium Iodide | 0.05% |
| Water qs to | 100.0% |

This medium was incubated at 28° C. on a shaker at 200 rpm for 5 days at which time the mash was harvested.

A concentration of 4 to 20 µg/ml of potassium iodide appears to be optimal, but concentrations of 2 mg/ml do not appear to depress yields.

NRRL-15839 can be induced to produce LL-E33288$\beta_1$-I when potassium iodide is present in the medium, but only at very low levels (0.2–0.3 µg/ml as against 1.5–3.5 µg/ml for the better producing NRRL-15975.

Yields of $\beta_1$-I and $\gamma_1$-I in an iodine medium are 2 to 8 times greater than yields of corresponding brominated compounds $\beta_1$-Br and $\gamma_1$-Br in a bromine medium using NRRL-15975.

EXAMPLE 8

Separation of LL-E33288$\alpha_1$-I, $\alpha_2$-I and $\alpha_3$-I from LL-E33288$\beta_1$-I, $\beta_2$-I, $\gamma_1$-I and $\delta_1$-I Approximately 41.3 g of crude LL-E33288 complex derived from the processing 7500 liters of a fermentation using NRRL-15975 and medium containing inorganic iodide was divided evenly into two portions and chromatographed on two separate 2.5×110 cm silica gel column (Silica Woelm, 32–63 um) packed and equilibrated with ethyl acetate. The columns were first eluted with ethyl acetate at a flow rate of 4 ml/minute for 4 hours, collecting 20 ml fractions. The eluent was changed to a concave gradient from ethyl acetate saturated with 0.1M aqueous potassium dihydrogen phosphate to 10% isopropyl alcohol in ethyl acetate saturated with 0.1M aqueous potassium dihydrogen phosphate over 24 hours. The columns were finally eluted with 10% isopropyl alcohol in ethyl acetate saturated with 0.1M aqueous potassium dihydrogen phosphate over night. The fractions were assayed in the BIA and those active were analyzed by TLC as described in Example 3.

Fractions (86–107) containing LL-E33288$\alpha_3$-I from the two columns were pooled and worked up as before to yield about 2.1 g of crude LL-E33288$\alpha_3$-I.

Fractions (182–253) containing LL-E33288$\beta_1$-I and $\alpha_2$-I from the two columns were pooled and worked up to yield about 4.2 g of a crude mixture of LL-E33288$\alpha_1$-I and $\alpha_2$-I.

Fractions (254–272) containing LL-E33288$\beta_2$-I and $\beta_1$-I from the two columns were pooled and worked up to yield about 1.2 g of a crude mixture of LL-E33288$\beta_2$-I and $\beta_1$-I.

Fractions (273–302) containing LL-E33288$\gamma_1$-I from the two columns were pooled and worked up to yield about 1.9 g of 30% pure LL-E33288$\gamma_1$-I.

Fractions (303–340) containing LL-E33288$\beta_1$-I from the two columns were pooled and worked up to yield about 1.3 g of partially purified LL-E33288$\beta_1$-I.

EXAMPLE 9

Purification of LL-E33288$\gamma_1$-I

Approximately 900 mg of the 30% pure LL-E33288$\gamma_1$-I from Example 8 was chromatographed on a 2.5×120 cm sephadex LH-20 column equilibrated with ethyl acetate:dichloromethane:ethanol (2:2:1) at a flow rate of 1 ml/minute, collecting 12 ml fractions. The fractions were assayed and analyzed by TLC as before and those containing LL-E33288$\gamma_1$-I (fractions 24–33) were pooled and worked up to yield 428 mg of 64% pure LL-E33288$\gamma_1$-I.

A 22 mg sample of the above was chromatographed on a 0.8×24 cm Sepralyte $C_{18}$ (35–60 um, Analytichem) column equilibrated with acetonitrile: 0.2M aqueous ammonium acetate (55.45) at a flow rate of 2 ml/minute, collecting 12 ml fractions. The fractions were assayed and analyzed by TLC as before and those containing pure LL-E33288$\gamma_1$-I were pooled and worked up to yield 7.7 mg of pure LL-E33288$\gamma_1$-I.

EXAMPLE 10

Purification of LL-E33288$\beta_1$-I and $\beta_2$-I

Approximately 600 mg of the crude mixture of LL-E33288$\beta_2$-I and $\beta_1$-I from Example 8 was chromatographed on a 2.5×120 cm Sephadex LH-20 column equilibrated with ethyl acetate:dichloromethane:ethanol (2:2:1) at a flow rate of 1 ml/minute, collecting 12 ml fractions. The fractions were assayed and analyzed by TLC as before and those containing LL-E33288$\beta_2$-I and LL-E33288$\beta_1$-I (fractions 23–31) were pooled and worked up to yield 81 mg of a partially purified mixture of LL-E33288$\beta_2$-I and $\beta_1$-I.

The sample above was chromatographed on a 1.5×90 cm Sephadex LH-20 column equilibrated with hexane:dichloromethane:ethanol (3:1:1) at a flow rate of 0.8 ml/minute, collecting 12 ml fractions. The fractions were assayed and analyzed by TLC as before and those containing LL-E33288$\beta_2$-I (fractions 17–30) and LL-E33288$\beta_1$-I (fractions 31–38) were pooled separately and worked up to yield 31 mg of partially purified LL-E33288$\beta_2$-I and 20 mg of 80% pure LL-E33288$\beta_1$-I.

In order to produce the LL-E33288 complex of antibiotics, the derived mutant LL-E33288-UV 784, NRRL-18149 is aerobically fermented under conditions described in the examples to follow.

The isolation and separation of the LL-E33288 components is also described in detail in the discussion and examples to follow.

High Performance Liquid Chromatograph Quantitation of the LL-E33288 Antibiotics In both the tank fermentations and the strain improvement work, the amount of LL-E33288 antibiotics present in the fermentation broths are quantitated by high performance liquid chromatography (HPLC). For each analysis, 10 ml of the whole mash is extracted with 10 ml of ethyl acetate by vortexing the mixture for 3 minutes. The mixture is then centrifuged and 5 ml of the organic phase is concentrated to dryness. The residue is redissolved in 500 µl of acetonitrile, filtered and analyzed using the following conditions:

Column: Waters NOVA-PAK® C18 Radial-PAK cartridge, 5 mm×10 cm

Mobile Phase: 0.2M aqueous ammonium acetate:acetonitrile (50:50)

Flow Rate: 1.2 ml per minute

Detection: $UV_{254}$ nm and $UV_{366}$ nm, both at 0.02 A.U.F.S.

The approximate retention times and volumes of LL-E33288$\alpha_2$-I, $\alpha_3$-I, $\beta_1$-I, $\gamma_1$-I and $\delta_1$-I under these conditions are given in Table EE.

TABLE EE

| LL-E33288 Components | Retention Time (minutes) | Retention Volume (ml) |
|---|---|---|
| $\alpha_2$-I | 9.1 | 10.9 |
| $\alpha_3$-I | 1.5 | 1.8 |
| $\beta_1$-I | 4.4 | 5.3 |
| $\gamma_1$-I | 3.6 | 4.3 |
| $\delta_1$-I | 2.6 | 3.1 |

General Procedure for the Isolation and Separation of the LL-E33288 Antibiotics form the Fermentation of NRRL-18149

The LL-E33288 antibiotics are recovered from the fermentation broth by extracting the whole mash with ethyl acetate or a mixture of acetone and ethyl acetate. The antibiotic complex, contained in the organic extract, is further purified by selective precipitation from lower hydrocarbons. The crude LL-E33288 antibiotic complex thus obtained is further purified and separated into the individual components by a series of column chromatographies using silica gel, Sephadex® LH-20 (hydroxy propylated dextran, Pharmacia Fine Chemicals) and $C_{18}$ bonded silica.

EXAMPLE 11

Small Scale Preparation of LL-E33288 Complex from LL-E33288-UV 784, NRRL-18149

A suspension containing spores and mycelia was prepared from a slant of *Micromonospora echinospora* ssp. *calichensis*, LL-E33288-UV 784 (NRRL-18149) by adding 5–8 ml of water and scraping the surface of the slant. This suspension was used to inoculate 50 ml of a sterile medium of the following composition:

| | |
|---|---|
| Yeast extract | 0.5% |
| Beef extract | 0.3% |
| Tryptose | 0.5% |
| Dextrin | 2.4% |
| Dextrose | 0.5% |
| Calcium carbonate | 0.4% |
| Water qs | 100% |

The above medium, in a 250 ml Erlenmeyer flask, was incubated at 28° C. on a rotary shaker at 200 rpm for 3–4 days thus providing stage I inoculum.

Stage I inoculum was used to inoculate 50 ml of the same sterile medium in a 250 ml baffled flask and incubated at 28° C. on a rotary shaker at 250 rpm for 2 days, thus providing stage II inoculum.

Stage II inoculum was used to inoculate 100 ml of sterile fermentation medium of the following composition:

| Sucrose | 2.0% |
|---|---|
| Ferrous sulfate heptahydrate | 0.01% |
| Magnesium sulfate heptahydrate | 0.02% |
| Calcium carbonate | 0.25% |
| Peptone | 0.4% |
| Molasses | 0.25% |
| Potassium iodide* | 0.01% |
| Water qs | 100% |

*Potassium bromide may be substituted to produce the bromo analogs.

The above medium in 500 ml baffled flasks was incubated at 28°–30° C. on a rotary shaker at 250 rpm for 6 days at which time the fermentation was harvested.

EXAMPLE 12

Large Scale Fermentation of LL-E33288 Complex Using LL-E33288-UV 784

A three stage inoculum was prepared using a culture of LL-E33288-UV 784 (NRRL-18149). The inoculum media were of the following formulation:

| Ingredient | per/liter |
|---|---|
| Calcium carbonate | 4 g |
| Hodag ® FD 82* | 1 ml |
| Dextrin | 24 g |
| Glucose | 5 g |
| Yeast extract | 5 g |
| Tryptone | 5 g |
| Beef extract | 3 g |
| Water qs | |

*Hodag ® FD 82 is a silicone antifoam agent.

The first stage consisted of 100 ml of the above sterile medium in a 500 ml flask incubated at 32° C. and 200 rpm for 2 days. This first stage was used to inoculate a second stage consisting of 10 liters of the above sterile medium which was grown for 2 days at 32° C. and 450 rpm in a small fermenter with a sterile air flow of one volume of air per volume of mash per minute (VVM). This second stage was used to inoculate a third stage consisting of 300 liters of the above sterile medium which was grown for 2 days at 32° C., 200–250 rpm and a sterile air flow of 0.67 VVM in a tank fermenter.

A 150 liter portion of this stage III inoculum was used to inoculate a sterile 1500 liter fermentation medium of the following composition:

| Ingredient | per/liter |
|---|---|
| Sucrose | 20.0 g |
| Ferrous sulfate heptahydrate | 0.1 g |
| Magnesium sulfate heptahydrate | 0.2 g |
| Peptone | 5.0 g |
| Molasses | 5.0 g |
| Potassium iodide* | 0.5 g |
| Calcium carbonate | 5.0 g |
| Hodag ® FD 82 | 5.0 ml |
| Water qs | |

*Potassium bromide may be substituted to produce the bromo analogs.

The fermentation was carried out at 30° C., a sterile air flow of 0.75 VVM, a back pressure of 8 psig and agitation by an impeller driven at 120 rpm for 5–6 days at which time the mash was harvested.

EXAMPLE 13

Isolation of Crude LL-E33288$\alpha_3$-I, LL-E33288$\beta_1$-I, LL-E33288$\gamma_1$-I and LL-E33288$\delta_1$-I from a Fermentation of LL-E33288-UV-784 (NRRL-18149)

A 1500 liter portion of whole harvest mash containing 12.4 g of LL-E33288$\gamma_1$-I and 10.5 g of LL-E33288$\delta_1$-I, which had been conducted essentially as described in Example 12, was mixed thoroughly with 1500 liters of ethyl acetate for 3 hours, then filter aid was added and the mixture filtered. The organic phase was separated, concentrated to 100 liters, adjusted to pH 6–7 with 2N sodium hydroxide and any aqueous phase discarded. The organic phase was further concentrated to 20 liters and any aqueous phase and interfacial fats removed. The organic phase was finally concentrated to a golden yellow syrup which was poured slowly into 7–8 times its volume of rapidly stirred hexane. The hexane insoluble gum, containing the LL-E33288 antibiotics, was collected, redissolved in 3 liters of ethyl acetate and dried over anhydrous sodium sulfate. The dried ethyl acetate solution was concentrated to a small volume and precipitated by the addition of ether and hexane, giving 53 g of crude LL-E33288 complex, containing 4.9 g of $\gamma_1$-I, 2.8 g of $\delta_1$-I and small amounts of $\alpha_3$-I and $\beta_1$-I.

EXAMPLE 14

Separation of LL-E33288$\beta_1$-I, $\gamma_1$-I, $\delta_1$-I and $\alpha_3$-I

A 7.2 g portion of crude LL-E33288 complex from Example 13 was chromatographed on two Sepralyte C-18 (35–65 m) columns (2.5×23 cm), eluting with acetonitrile: 0.2M aqueous ammonium acetate (45:55) at 12 ml/minute, collecting sixty 24 ml fractions from each column. Each fraction was analyzed by TLC (EM silica gel 60F$_{254}$ pre-coated aluminum sheets, 3% isopropanol in ethyl acetate saturated with 0.1M KH$_2$PO$_4$ elution, detected with UV$_{254nm}$ quenching and bioautography via the BIA) and those containing $\gamma_1$-I were pooled and concentrated on a rotary evaporator to remove acetonitrile. The aqueous mixture was extracted twice with equal volumes of ethyl acetate and the ethyl acetate solution dried over anhydrous sodium sulfate, concentrated and precipitated by addition of hexane to yield 504 mg of partially purified LL-E33288$\gamma_1$-I (60% pure) containing $\beta_1$-I.

Fractions containing $\alpha_3$-I and $\delta_1$-I eluting off the column ahead of $\gamma_1$-I, were pooled separately and worked up to yield 812 mg of partially purified $\alpha_3$-I (12% pure) and 1336 mg (22% $\delta_1$-I, 20% $\gamma_1$-I) of a partially purified mixture of $\delta_1$-I and $\gamma_1$-I.

EXAMPLE 15

Purification of LL-E33288$\gamma_1$-I

A 309 mg portion of partially purified $\gamma_1$-I (66% pure) was chromatographed on a Sephadex ® LH-20 (hydroxy propylated dextran) column (1.5×90 cm) equilibrated with hexane:dichloromethane:ethanol (2:1:1). The column was eluted with the same solvent system at 1.5 ml/minute and twenty-five 20 ml fractions were collected and analyzed as before. Fractions containing pure $\gamma_1$-I were pooled and concentrated as before to a light yellow residue. This residue was redissolved in ethyl acetate and precipitated by the addition of hexane to yield 194 mg of pure LL-E33288$\gamma_1$-I.

EXAMPLE 16

Purification of LL-E33288$\beta_1$-I

A 1.05 g portion of partially purified $\gamma_1$-I containing $\beta_1$-I (61% $\gamma_1$-I, 10% $\beta_1$-I) was chromatographed on a Woelm silica (32–63μ) column (1.5×45 cm) packed and equilibrated with ethyl acetate. The column was eluted with ethyl acetate at 3.6 ml/minute for one hour, then the eluent was changed to ethyl acetate:methanol (97:3) and the elution was continued for 2 hours. Fractions of 18 ml were collected during the entire elution. Each fraction was analyzed as before and those containing $\beta_1$-I were pooled and worked up to yield 56 mg of 86% pure LL-E33288$\beta_1$-I.

Fractions containing $\gamma_1$-I were also worked up to yield 385 mg of 74% pure LL-E33288$\gamma_1$-I.

EXAMPLE 17

Purification of LL-E33288$\delta_1$-I

A partially purified mixture of $\delta_1$-I and $\gamma_1$-I (1.8 g, containing 648 mg of $\gamma_1$-I and 540 mg of $\delta_1$-I) was chromatographed on a Woelm silica (32–63μ) column (1.5×45 cm) packed and equilibrated with ethyl acetate. The column was eluted with ethyl acetate at 3 ml/minute for one hour, then the eluent was changed to ethyl acetate:methanol (97:3) and the elution was continued for 2 hours. Fractions of 15 ml were collected during the entire elution. Each fraction was analyzed as before and those containing pure $\delta_1$-I were pooled and worked up to yield 367 mg of pure LL-E33288$\delta_1$-I.

Fractions containing $\gamma_1$-I were also worked up to yield 574 mg of 65% pure LL-E33288$\gamma_1$-I.

EXAMPLE 18

Purification of LL-E33288$\alpha_3$-I

A partially purified sample of $\alpha_3$-I (1.8 g, containing 310 mg of $\alpha_3$-I) was chromatographed on a Sephadex ® LH-20 column (1.5×90 cm) equilibrated with hexane:-dichloromethane:ethanol (2:1:1). The column was eluted with the same solvent system at 4 ml/minute and forty-five 20 ml fractions were collected and analyzed as before. Fractions containing pure $\alpha_3$-I were pooled and concentrated as before to a light yellow residue which was redissolved in ethyl acetate and precipitated by the addition of hexane to yield 289 mg of pure LL-E33288$\alpha_3$-I.

EXAMPLE 19

Preparation of LL-E33288$\alpha_2$-I from LL-E33288$\gamma_1$-I

A 300 mg portion of partially purified $\gamma_1$-I (60% pure) was dissolved in 60 ml of 2% hydrogen chloride in methanol and the solution was allowed to remain at room temperature for 6 hours. The reaction mixture was then neutralized by the addition of a saturated methanol solution of potassium carbonate. The precipitated potassium chloride was filtered off and the solution was concentrated to dryness. The ethyl acetate soluble portion of the residue was concentrated and precipitated from hexane to yield 135 mg of crude LL-E33288$\alpha_2$-I.

This crude $\alpha_2$-I was purified by chromatography on a Bio-Sil ® (20–40μ) column (1.5×20 cm) eluting with dichloromethane:methanol (96:4) to give 34 mg of analytically pure LL-E33288$\alpha_2$-I. The small amounts of LL-E33288$\alpha_2$-I isolated previously from the fermentation of NRRL-15839 was identified with the LL-E33288$\alpha_2$-I prepared as described in this example by TLC and HPLC analyses.

What is claimed is:

1. A LL-E33288$\alpha$-Br complex prepared by extracting LL-E33288$\alpha_1$-Br, LL-E33288$\alpha_2$-Br, LL-E33288$\alpha_3$-Br, LL-E33288$\alpha_4$-Br, LL-E33288$\beta_1$-Br, LL-E33288$\beta_2$-Br and LL-E33288$\gamma_1$-Br from the fermentation broth of *Micromonospora echinospora* NRRL-15839, NRRL-15975 or NRRL-18149 with an organic solvent and
   purifying the extracted mixture by selective precipitation from lower hydrocarbons,
   separating LL-E33288$\alpha_1$-Br, LL-E33288$\alpha_2$-Br, LL-E33288$\alpha_3$-Br and LL-E33288$\alpha_4$-Br from LL-E33288$\beta_1$-Br, LL-E33288$\beta_2$-Br and LL-E33288$\gamma_1$-Br by a series of column chromatography and
   assaying and analyzing the LL-E33288$\alpha$-Br complex by thin layer chromatography.

2. A compound LL-E33288$\alpha_2$-Br, having the following $R_f$ values in the indicated solvent systems on TLC on silica gel sheets:
   (a) ethyl acetate saturated with 0.1M aqueous potassium dihydrogen phosphate, $R_f$=0.61;
   (b) 3% isopropanol in ethyl acetate saturated with 0.1M aqueous potassium dihydrogen phosphate, $R_f$=0.75; and
   (c) ethyl acetate:methanol (95:5), $R_f$=0.73;
   and having the following structure:

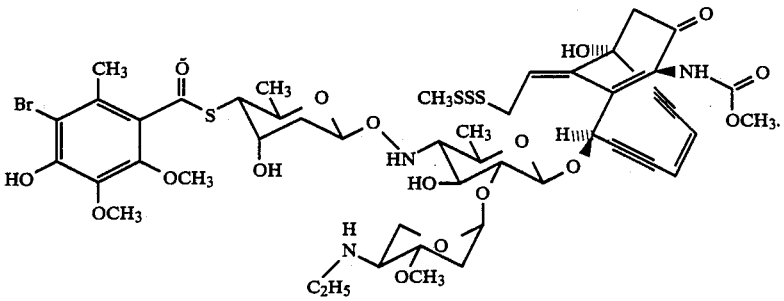

3. A compound LL-E33288$\alpha_3$-Br having the following $R_f$ values in the indicated solvent systems on TLC on silica gel sheets:
   (a) ethyl acetate saturated with 0.1M aqueous potassium dihydrogen phosphate, $R_f$=0.55;
   (b) 3% isopropanol in ethyl acetate saturated with 0.1M aqueous potassium dihydrogen phosphate, $R_f$=0.69; and
   (c) ethyl acetate:methanol (95:5), $R_f$=0.61;
   and having the following structure:

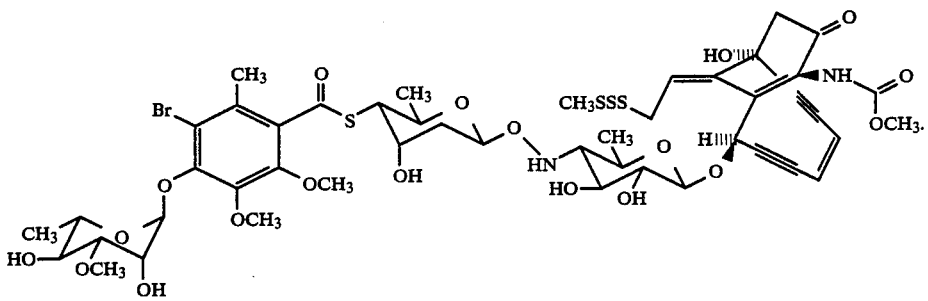

4. A compound LL-E33288$\beta_1$-Br,
(a) having an approximate elemental analysis: C 48.6; H 5.6; N 2.9; S 9.1 and Br 5.5;
(b) having a melting point: 146°-150° C. (dec.);
(c) having a specific rotation: $[\alpha]_D^{26} = -49° \pm 10°$ (0.1%, ethanol);
(d) having ultraviolet absorption spectra as shown in FIG. I of the drawings;
(e) having an infrared absorption spectrum as shown in FIG. II of the drawings;
(f) having a proton magnetic resonance spectrum as shown in FIG. III of the drawings;
(g) having a carbon-13 magnetic resonance spectrum as shown in FIG. IV of the drawings with significant peaks at:

| | | | |
|---|---|---|---|
| 17.60(q) | 17.64(q) | 18.9(q) | 19.7(q) |
| 22.4(q) | 22.8(q) | 23.5(q) | 34.3(t) |
| 36.9(t) | 39.2(t/d) | 47.8(d) | 51.7(q) |
| 52.7(q) | 54.6(d) | 56.3(q) | 57.2(q) |
| 57.8(d) | 61.0(q/d) | 61.7(d) | 62.4(t) |
| 66.9(d) | 68.4(d) | 69.1(d) | 69.7(d) |
| 70.2(d) | 71.1(d) | 71.9(d) | 72.1(s) |
| 76.1(d) | 81.0(d) | 83.3(s) | 88.2(s) |
| 97.4(d) | 99.7(d) | 100.8(s) | 102.5(d) |
| 115.1(s) | 123.4(d) | 124.4(d) | 126.5(d) |
| 130.2(s) | 130.8(s) | 144.6(s) | 149.3(s) |
| 149.5(s) | 191.7(s) | 192.4(s) | and |

(h) having the following $R_f$ values in the indicated solvent systems on TLC on silica gel sheets:
  (i) ethyl acetate saturated with 0.1M aqueous potassium dihydrogen phosphate, $R_f=0.24$;
  (ii) 3% isopropanol in ethyl acetate saturated with 0.1M aqueous potassium dihydrogen phosphate, $R_f=0.35$;
  (iii) ethyl acetate:methanol (95:5), $R_f=0.36$.
(i) having a molecular weight: 1333/1335, respectively for $^{79}$Br/$^{81}$Br;
(j) having a molecular formula: $C_{56}H_{76}N_3O_{21}S_4Br$;
(k) and having the structure 5. A compound LL-E33288$\beta_2$-Br, having the following $R_f$ values in the indicated solvent systems on TLC on silica gel sheets:
(a) ethyl acetate saturated with 0.1M aqueous potassium dihydrogen phosphate, $R_f=0.32$;
(b) 3% isopropanol in ethyl acetate saturated with 0.1M aqueous potassium dihydrogen phosphate, $R_f=0.41$; and
(c) ethyl acetate:methanol (95:5), $R_f=0.45$ prepared by extracting LL-E33288$\alpha_1$-Br, LL-E33288$\alpha_2$-Br, LL-E33288$\alpha_3$-Br, LL-E33288$\alpha_4$-Br, LL-E33288$\beta_1$-Br, LL-E33288$\beta_2$-Br and LL-E33288$\gamma_1$-Br from the fermentation broth of *Micromonospora echinospora* NRRL-15839, NRRL-15975 or NRRL-18149 with an organic solvent and
purifying the extracted mixture by selective precipitation from lower hydrocarbons,
separating LL-E33288$\beta_1$-Br, LL-E33288$\beta_2$-Br and LL-E33288$\gamma_1$-Br from LL-E33288$\alpha_1$-Br, LL-E33288$\alpha_2$-Br, LL-E33288$\alpha_3$-Br, and LL-E33288$\alpha_4$-Br by a series of column chromatography,
assaying, analyzing and working up the LL-E33288$\beta$-Br complex containing LL-E33288$\gamma_1$-Br and
separating LL-E33288$\beta_2$-Br from the LL-E33288$\beta$-Br complex containing LL-E33288$\gamma_1$-Br by column chromatography.

6. A compound LL-E33288$\gamma_1$-Br
(a) having ultraviolet absorption spectra as shown in FIG. V of the drawings;
(b) having an infrared absorption spectrum as shown in FIG. VI of the drawings;
(c) having a proton magnetic resonance spectrum as shown in FIG. VII of the drawings; and
(d) having the following $R_f$ values in the indicated solvent systems on TLC on silica gel sheets:

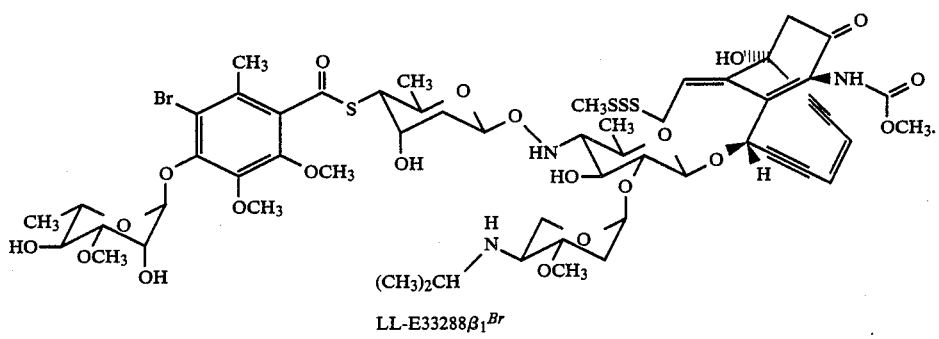

LL-E33288$\beta_1^{Br}$ (i) ethyl acetate saturated with 0.1M aqueous potassium dihydrogen phosphate, $R_f=0.18$;
(ii) 3% isopropanol in ethyl acetate saturated with 0.1M aqueous potassium dihydrogen phosphate, $R_f=0.28$;
(iii) ethyl acetate:methanol (95:5), $R_f=0.27$, (e) having a carbon-13 magnetic resonance spectrum as shown in FIG. VIII of the drawings with significant peaks at:

| | | | |
|---|---|---|---|
| 14.4 | 17.6 | 17.9 | 19.0 |
| 19.7 | — | 22.8 | — |
| — | 34.0 | 37.6 | 39.5 |
| 42.1 | — | 51.6 | 52.7 |
| 54.1 | 56.3 | 57.3 | — |
| 59.3 | 61.1 | 61.8 | 61.9 |
| 67.2 | 68.18 | 68.23 | 69.7 |
| 70.1 | 70.8 | 71.1 | 71.7 |
| 71.8 | 76.1 | — | 81.0 |
| 82.9 | 88.4 | — | 97.8 |
| 100.0 | 100.2 | 101.3 | 103.0 |
| 115.3 | 123.0 | 124.9 | 126.9 |
| 130.4 | 131.1 | 131.8 | 138.0 |
| 144.7 | — | 149.5 | 149.6 |
| 155.6 | 192.5 | 192.9 | |

(f) having a molecular formula: $C_{55}H_{74}N_3O_{21}S_4Br$;
(g) having a molecular weight: 1319/1321, respectively for $^{79}Br/^{81}Br$;
(h) and having the structure NRRL-15839, NRRL-15975 and NRRL-18149 with an organic solvent,
purifying the extracted mixture by selective precipitation from lower hydrocarbons,
separating LL-E33288$\alpha_1$-I from a complex including LL-E33288$\alpha_2$-I, LL-E33288$\alpha_3$-I, LL-E33288$\beta_1$-I, LL-E33288$\beta_2$-I, LL-E33288$\gamma_1$-I and LL-E33288$\delta_1$-I by a series of column chromatography.

8. A compound LL-E33288$\alpha_2$-I
(a) having the following $R_f$ values in the indicated solvent systems on TLC on silica gel sheets:
(i) ethyl acetate saturated with 0.1M aqueous potassium dihydrogen phosphate, $R_f=0.61$;
(ii) 3% isopropanol in ethyl acetate saturated with 0.1M aqueous potassium dihydrogen phosphate, $R_f=0.75$; and
(iii) ethyl acetate:methanol (95:5), $R_f=0.73$;
(b) containing only the following elements: C, H, N, O, S and I;
(c) having a molecular weight: 1207;
(d) having ultraviolet absorption spectra as shown in FIG. IX of the drawings;
(e) having an infrared absorption spectrum as shown in FIG. X of the drawings;
(f) having a proton magnetic resonance spectrum as shown in FIG. XI of the drawings;
(g) having a carbon-13 magnetic resonance spectrum as shown in FIG. XII of the drawings with significant peaks at:

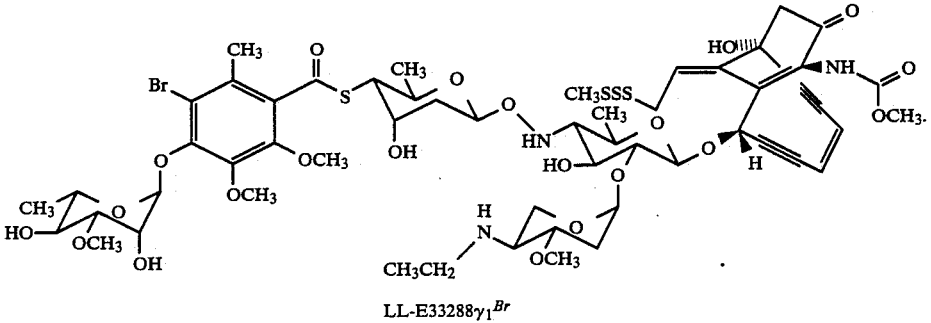

LL-E33288$\gamma_1^{Br}$

7. A compound LL-E33288$\alpha_1$-I
(a) having the following $R_f$ values in the indicated solvent systems on TLC on silica gel sheets:
(i) ethyl acetate saturated with 0.1 M aqueous potassium dihydrogen phosphate, $R_f=0.67$;
(ii) 3% isopropanol in ethyl acetate saturated with 0.1M aqueous potassium dihydrogen phosphate, $R_f=0.80$; and
(iii) ethyl acetate:methanol (95:5), $R_f=0.80$;
(b) having a molecular weight: 1145 prepared by extracting LL-E33288$\alpha_1$-I, LL-E33288$\alpha_2$-1, LL-E33288$\alpha_3$-I, LL-E33288$\beta_1$-I, LL-E33288$\beta_2$-I, LL-E33288$\gamma_1$-I and LL-E33288$\delta_1$-I from the fermentation broth of Micromonospora echinospora cant peaks at:

| | | | |
|---|---|---|---|
| 17.7 | 56.3 | 71.8 | 122.7 |
| 18.8 | 60.7 | 73.7 | 125.1 |
| 22.7 | 61.4 | 79.0 | 126.3 |
| 24.7 | 60.7 | 82.6 | 127.1 |
| 33.1 | 67.7 | 87.4 | 133.1 |
| 37.4 | 67.9 | 85.4 | 137.0 |
| 39.6 | 69.6 | 98.0 | 137.1 |
| 41.4 | 69.7 | 100.4 | 149.2 |
| 51.3 | 70.3 | 100.1 | 151.5 |
| 53.3 | 71.0 | 100.8 | 192.8 |
| 53.8 | 73.4 | 98.2 | 193.2 |

(h) having a molecular formula: $C_{48}H_{62}N_3O_{17}S_4I_9$;
(i) and having the structure

LL-E33288α₂ᴵ

9. A compound LL-E33288α₃3-I
(a) having the following $R_f$ values in the indicated solvent systems on TLC on silica gel sheets:
  (i) ethyl acetate saturated with 0.1M aqueous potassium dihydrogen phosphate, $R_f$=0.55;
  (ii) 3% isopropanol in ethyl acetate saturated with 0.1M aqueous potassium dihydrogen phosphate, $R_f$=0.69; and
  (iii) ethyl acetate:methanol (95:5), $R_f$=0.61;
(b) having a molecular weight: 1210;
(c) having ultraviolet absorption spectra as shown in FIG. XIII of the drawings;
(d) having an infrared absorption spectrum as shown in FIG. XIV of the drawings;
(e) having a proton magnetic resonance spectrum as shown in FIG. XV of the drawings;
(f) having a carbon-13 magnetic resonance spectrum as shown in FIG. XVI of the drawings with significant peaks at:

| | | |
|---|---|---|
| 17.5(q) | 69.5(d) | 103.1(d) |
| 18.0(q) | 70.0(d) | 123.4(d) |
| 19.0(q) | 70.1(d) | 124.7(d) |
| 22.7(q) | 70.8(d) | 127.3(d) |
| 25.3(q) | 70.9(d) | 131.1 |
| 37.4(t) | 72.1(s) | 130.4(s) |
| 39.2(t) | 71.3(d) | 133.5(s) |
| 51.5(d) | 74.5(d) | 136.8(s) |
| 53.5(q) | 80.8(d) | 143.0(s) |
| 53.7(t) | 83.1(s) | 145.8 |
| 57.2(q) | 87.6(s) | 150.5(s) |
| 61.0(q) | 93.7(s) | 151.6(s) |
| 61.8(q) | 98.6(s) | 154.7(s) |
| 67.1(d) | 100.1(d) | 192.4(s) |
| 67.3(d) | 101.0(s) | 192.6(s) |
| 68.0(d) | 103.4(d) | |

(g) having a molecular formula: $C_{47}H_{59}N_2O_{19}S_4I$;
(h) and having the structure 10. A compound LL-E33288β₁-I
(a) having the following $R_f$ values in the indicated solvent systems on TLC on silica gel sheets:
  (i) ethyl acetate saturated with 0.1M aqueous potassium dihydrogen phosphate, $R_f$=0.24;
  (ii) 3% isopropanol in ethyl acetate saturated with 0.1M aqueous potassium dihydrogen phosphate, $R_f$=0.35; and
  (iii) ethyl acetate:methanol (95:5), $R_f$=0.36;
(b) having ultraviolet absorption spectra as shown in FIG. XVII of the drawings;
(c) having an infrared absorption spectrum as shown in FIG. XVIII of the drawings;
(d) having a proton magnetic resonance spectrum as shown in FIG. XIX of the drawings;
(e) having a carbon-13 magnetic resonance spectrum as shown in FIG. XX of the drawings with significant peaks at:

| | | | |
|---|---|---|---|
| — | 17.5 | 17.6 | 18.9 |
| — | 22.4 | 22.8 | 23.4 |
| 25.4 | 34.3 | 36.9 | 39.2 |
| — | 47.9 | 51.6 | 52.8 |
| 54.8 | 56.3 | 57.2 | 57.9 |
| 60.9 | — | 61.6 | 62.2 |
| 67.0 | 68.4 | 68.4 | 69.1 |
| 69.6 | 70.4 | 71.1 | 71.8 |
| 72.2 | 76.2 | — | 80.8 |
| 83.3 | 88.1 | 93.6 | 97.4 |
| 99.6 | 99.6 | — | 102.6 |
| 112.4 | 123.4 | 124.4 | 126.4 |
| — | — | 133.4 | — |
| — | — | — | — |
| — | 192.2 | 192.6 | — |

(f) having a molecular formula: $C_{56}H_{76}N_3O_{21}S_4I$;
(g) having a molecular weight: 1381;
(h) and having the structure

LL-E33288α₃ᴵ

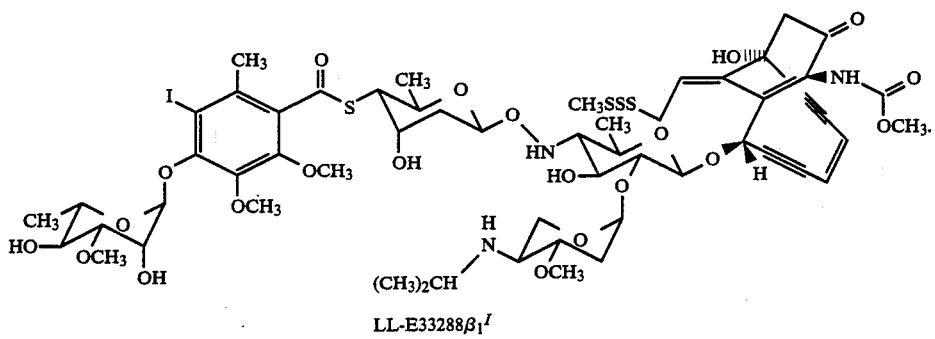

LL-E33288β₁¹

11. A compound LL-E33288β₂-I having the following $R_f$ values in the indicated solvent systems on TLC on silica gel sheets:
   (a) ethyl acetate saturated with 0.1M aqueous potassium dihydrogen phosphate, $R_f$=0.32;
   (b) 3% isopropanol in ethyl acetate saturated with 0.1M aqueous potassium dihydrogen phosphate, $R_f$=0.41; and
   (c) ethyl acetate:methanol (95:5), $R_f$=0.45 prepared by
   extracting LL-E33288α₁-I, LL-E33288α₂-I, LL-E33288α₃-I, LL-E33288β₁-I, LL-E33288β₂-I, LL-E33288γ₁-I and LL-E33288δ₁-I from the fermentation broth of *Micromonospora echinospora* NRRL-15839, NRRL-15975 and NRRL-18149 with an organic solvent,
   purifying the extracted mixture by selective precipitation from lower hydrocarbons; and
   separating LL-E33288β₂-I from LL-E33288α₁-I, LL-E33288α₂-I, LL-E33288α₃-I, LL-E33288β₁-I, LL-E33288γ₁-I and LL-E33288δ₁-I by a series of column chromatography.

12. A compound LL-E33288γ₁-I
   (a) having the following $R_f$ values in the indicated solvent system on TLC on silica gel sheets:
   (i) ethyl acetate saturated with 0.1M aqueous potassium dihydrogen phosphate, $R_f$=0.18;
   (ii) 3% isopropanol in ethyl acetate saturated with 0.1M aqueous potassium dihydrogen phosphate, $R_f$=0.28; and
   (iii) ethyl acetate: methanol (95:5), $R_f$=0.27;
   (b) containing only the following elements: C, H, N, O, S and I;
   (c) having an approximate elemental analysis: C 48.8; H 5.4; N 2.8; S 9.0; and I 9.2;
   (d) having a molecular weight: 1367;
   (e) having a molecular formula: $C_{55}H_{74}N_3O_{21}S_4I$;
   (f) having an ultraviolet absorption spectra as shown in FIG. XXI of the drawings;
   (g) having an infrared absorption spectrum as shown in FIG. XXII of the drawings;
   (h) having a proton magnetic resonance spectrum as shown in FIG. XXIII of the drawings; and
   (i) having a carbon-13 magnetic resonance spectrum as shown in FIG. XXIV of the drawings, significant peaks as listed below:

| | | | |
|---|---|---|---|
| 14.5(q) | 17.6(q) | 17.6(q) | 18.9(q) |
| — | — | 22.8(q) | — |
| 25.4(q) | 34.1(t) | 37.0(t) | 39.1(t) |
| 42.3(t/s) | — | 51.5(d) | 52.8(q) |
| 54.8(t) | 56.3(q) | 57.2(q) | — |
| 60.4(d) | 60.9(q) | 61.3(t) | 61.7(q) |
| 67.0(d) | 68.4(d) | 68.5(d) | 69.2(d) |
| 69.7(d) | 70.5 | 71.1(d) | 71.8(d) |
| 72.1(s) | 75.7(d) | 75.8(d) | 80.9(d) |
| 82.8(s) | 88.1(s) | 93.5(s) | 97.3(s) |
| 99.6(d) | 99.7(d) | 100.8(s) | 102.6(d) |
| — | 123.4(d) | 124.4(d) | 126.2(d) |
| 103.2(s) | 131.0(s) | 133.4(s) | 139.1(s) |
| 143.0(s) | 145.1 | 150.6(s) | 151.5(s) |
| 154.5 | 192.0(s) | 192.5(s) | |

(j) and having the structure

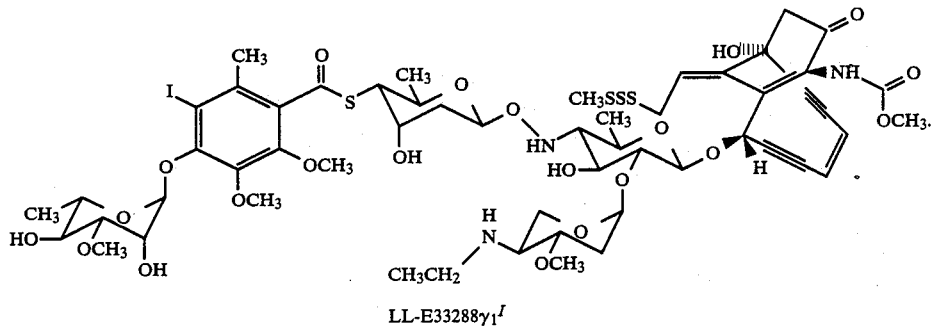

LL-E33288γ₁¹

13. A compound LL-E33288δ₁-I
   (a) having the following $R_f$ values in the indicated solvent system on TLC on silica gel sheets:
   (i) ethyl acetate saturated with 0.1M aqueous potassium dihydrogen phosphate, $R_f$=0.11; and
   (ii) 3% isopropanol in ethyl acetate saturated with 0.1M aqueous potassium dihydrogen phosphate, $R_f$=0.19;
   (b) having ultraviolet absorption spectra as shown in FIG. XXV of the drawings;
   (c) having an infrared absorption spectrum as shown in FIG. XXVI of the drawings;

(d) having a proton magnetic resonance spectrum as shown in FIG. XXVII of the drawings; and
(e) having a carbon-13 magnetic resonance spectrum as shown in FIG. XXVIII of the drawings, significant peaks as listed below:

| | | |
|---|---|---|
| 17.2 | 60.4 | 99.6 |
| 17.6 | 66.8 | 103.0 |
| 18.5 | 67.7 | 122.7 |
| 22.4 | 69.5 | 124.7 |
| 25.0 | 69.8 | 126.6 |
| 33.0 | 70.6 | 130.7 |
| 37.3 | 70.7 | 130.1 |
| 39.0 | 71.1 | 133.2 |
| 33.5 | 71.3 | 137.7 |
| 51.0 | 76.0 | 142.8 |
| 52.4 | 80.4 | 150.3 |
| 53.6 | 82.5 | 151.5 |
| 56.1 | 88.1 | 155.5 |
| 57.0 | 93.4 | 192.7 |
| 61.0 | 97.5 | 192.8 |
| 60.6 | 100.9 | |
| 61.4 | 99.8 | |

(f) and having the structure

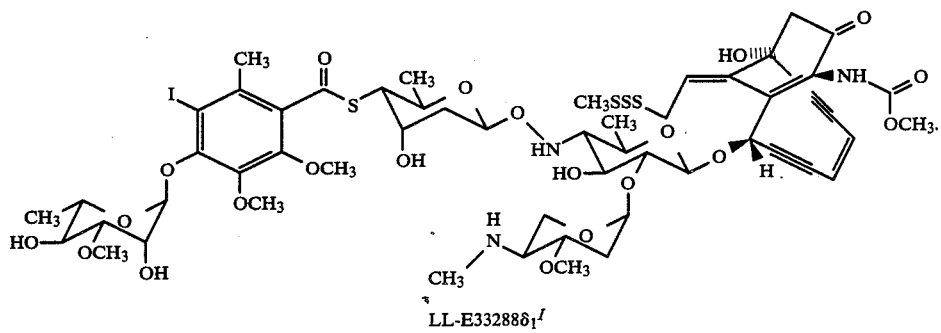

LL-E33288$\delta_1{}^I$

14. A method of treating bacterial infections in warm-blooded animals which comprises administering to said animals an antibacterially effective amount of a compound selected from the group consisting of LL-E33288$\alpha_{[1]}$-Br complex; LL-E33288$\alpha_2$-Br; LL-E33288$\alpha_2$-I; LL-E33288$\alpha_3$-Br; LL-E33288$\alpha_3$-I; LL-E33288$\beta_1$-Br; LL-E33288$\beta_1$-I; LL-E33288$\beta_2$-Br; LL-E33288$\beta_2$-I; LL-E33288$\gamma_1$-Br; LL-E33288$\gamma_1$-I; and LL-E33288$\delta_1$-I.

15. A method of treating the growth of tumors in a mammal comprising administering to said mammal an effective amount of a compound selected from the group consisting of LL-E33288$\alpha_{[1]}$-Br complex LL-E33288$\alpha_2$-Br; LL-E33288$\alpha_2$-I; LL-E33288$\alpha_3$-Br; LL-E33288$\alpha_3$-I; LL-E33288$\beta_1$-Br; LL-E33288$\beta_1$-I; LL-E32288$\beta_2$-Br; LL-E33288$\beta_2$-I; LL-E33288$\gamma_1$-Br; LL-E33288$\gamma_1$-I; and LL-E33288$\delta_1$-I.

16. A method of regressing leukemia in a mammal comprising administering to said mammal an effective amount of a compound selected from the group consisting of LL-E33288$\alpha$-Br complex; LL-E33288$\alpha_2$-Br; LL-E33288$\alpha_2$-I; LL-E33288$\alpha_3$-Br; LL-E33288$\alpha_3$-I; LL-E33288$\beta_1$-Br; LL-E33288$\beta_1$-I; LL-E33288$\beta_2$-Br; LL-E33288$\beta_2$-I; LL-E33288$\gamma_1$-Br; LL-E33288$\gamma_1$-I; and LL-E33288$\delta_1$-I.

* * * * *